United States Patent
Stanslaski et al.

(10) Patent No.: US 10,960,202 B2
(45) Date of Patent: Mar. 30, 2021

(54) ADAPTIVE DEEP BRAIN STIMULATION USING MOVEMENT DESYNCHRONIZATION

(71) Applicant: Medtronic, Inc., Minneapolis, MN (US)

(72) Inventors: Scott R. Stanslaski, Shoreview, MN (US); Timothy R. Abraham, Lino Lakes, MN (US); Thomas Adamski, Andover, MN (US); Timothy J. Denison, Minneapolis, MN (US); Robert S. Raike, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 448 days.

(21) Appl. No.: 15/714,867

(22) Filed: Sep. 25, 2017

(65) Prior Publication Data

US 2018/0085585 A1 Mar. 29, 2018

Related U.S. Application Data

(60) Provisional application No. 62/400,605, filed on Sep. 27, 2016.

(51) Int. Cl.
*A61N 1/36* (2006.01)
*A61N 1/05* (2006.01)
(Continued)

(52) U.S. Cl.
CPC ........ *A61N 1/0534* (2013.01); *A61B 5/04001* (2013.01); *A61B 5/4836* (2013.01);
(Continued)

(58) Field of Classification Search
CPC .. A61N 1/0529; A61N 1/0531; A61N 1/0534; A61N 1/0536; A61N 1/3605;
(Continued)

(56) References Cited

U.S. PATENT DOCUMENTS

| 5,593,431 A | 1/1997 | Sheldon |
| 6,463,328 B1 | 10/2002 | John |

(Continued)

FOREIGN PATENT DOCUMENTS

| WO | 2013123112 A1 | 8/2013 |
| WO | 2015109239 A1 | 7/2015 |

OTHER PUBLICATIONS

Office Action from U.S. Appl. No. 15/714,888, dated Oct. 30, 2019, 9 pp.

(Continued)

*Primary Examiner* — Eugene T Wu
(74) *Attorney, Agent, or Firm* — Shumaker & Sieffert, P.A.

(57) ABSTRACT

Techniques are disclosed for delivering electrical stimulation therapy to a patient. In one example, a medical system delivers electrical stimulation therapy to a tissue of the patient via electrodes. The medical system determines a first change of a first sensed signal of the patient to movement by the patient and a second change of a second sensed signal of the patient to the movement by the patient. Based on the first change and the second change, the medical system selects one of the first sensed signal and the second sensed signal of the patient for controlling the electrical stimulation therapy. The medical system adjusts a level of at least one parameter of the electrical stimulation therapy based on the selected one of the first sensed signal and the second sensed signal.

21 Claims, 18 Drawing Sheets

(51) Int. Cl.
*A61B 5/00* (2006.01)
*A61B 5/04* (2006.01)
*A61N 1/372* (2006.01)
*A61N 1/04* (2006.01)

(52) U.S. Cl.
CPC ............ *A61B 5/4848* (2013.01); *A61B 5/686* (2013.01); *A61B 5/6868* (2013.01); *A61N 1/36064* (2013.01); *A61N 1/36067* (2013.01); *A61N 1/36071* (2013.01); *A61N 1/36082* (2013.01); *A61N 1/36132* (2013.01); *A61N 1/36135* (2013.01); *A61N 1/36139* (2013.01); *A61N 1/37247* (2013.01); *A61B 5/0002* (2013.01); *A61N 1/0476* (2013.01); *A61N 1/36014* (2013.01); *A61N 1/36096* (2013.01)

(58) Field of Classification Search
CPC .............. A61N 1/3606; A61N 1/36067; A61N 1/36128; A61N 1/36132; A61N 1/36135; A61N 1/36139; A61N 1/36142; A61N 1/37235; A61N 1/37241; A61B 5/04012; A61B 5/04014; A61B 5/04015; A61B 5/04017; A61B 5/04018; A61B 5/0476; A61B 5/048; A61B 5/0482; A61B 5/0484; A61B 5/103; A61B 5/11; A61B 5/1101; A61B 5/1104; A61B 5/1116; A61B 5/1117; A61B 5/1118; A61B 5/40; A61B 5/4058; A61B 5/4064; A61B 5/4076; A61B 5/4082; A61B 5/4836; A61B 5/4848; A61B 5/7203; A61B 5/7207; A61B 5/721; A61B 5/7217; A61B 5/7221; A61B 5/4839
See application file for complete search history.

(56) References Cited

U.S. PATENT DOCUMENTS

| | | | |
|---|---|---|---|
| 7,324,851 B1* | 1/2008 | DiLorenzo | A61N 1/3605 607/45 |
| 8,078,281 B2 | 12/2011 | Priori et al. | |
| 8,190,251 B2 | 5/2012 | Molnar et al. | |
| 2003/0100931 A1 | 5/2003 | Mullett | |
| 2004/0111127 A1 | 6/2004 | Gliner | |
| 2007/0225674 A1 | 9/2007 | Molnar et al. | |
| 2009/0018619 A1* | 1/2009 | Skelton | A61N 1/37247 607/66 |
| 2009/0082691 A1 | 3/2009 | Denison et al. | |
| 2010/0010392 A1* | 1/2010 | Skelton | A61B 5/1116 600/595 |
| 2010/0100153 A1* | 4/2010 | Carlson | A61N 1/0529 607/45 |
| 2010/0228314 A1 | 9/2010 | Goetz | |
| 2011/0196446 A1 | 8/2011 | Wu et al. | |
| 2011/0270348 A1 | 11/2011 | Goetz | |
| 2011/0313483 A1 | 12/2011 | Hincapie Ordonez et al. | |
| 2012/0027375 A1 | 2/2012 | Yasui | |
| 2012/0150256 A1 | 6/2012 | Martens | |
| 2012/0271189 A1 | 10/2012 | Nelson et al. | |
| 2012/0271375 A1 | 10/2012 | Wu et al. | |
| 2013/0053722 A1 | 2/2013 | Carlson et al. | |
| 2013/0197605 A1 | 8/2013 | Carlson et al. | |
| 2013/0218232 A1 | 8/2013 | Giftakis et al. | |
| 2014/0163627 A1 | 6/2014 | Starr et al. | |
| 2014/0213926 A1 | 7/2014 | Vaidyanathan | |
| 2014/0221848 A1* | 8/2014 | Nagasaka | A61B 5/721 600/479 |
| 2014/0277235 A1 | 9/2014 | An et al. | |
| 2014/0350634 A1 | 11/2014 | Grill et al. | |
| 2014/0358024 A1* | 12/2014 | Nelson | A61B 5/04014 600/544 |
| 2015/0202447 A1 | 7/2015 | Afshar et al. | |
| 2015/0246233 A1 | 9/2015 | Kaemmerer | |
| 2016/0184589 A1 | 6/2016 | Li et al. | |
| 2018/0085572 A1 | 3/2018 | Stanslaski et al. | |
| 2018/0085585 A1 | 3/2018 | Stanslaski et al. | |
| 2018/0085586 A1 | 3/2018 | Stanslaski et al. | |

OTHER PUBLICATIONS

Beudel, et al., "Adaptive deep brain stimulation in Parkinson's disease," Parkinsonism and Related Disorders 22, Jan. 2016, S123-S126.
Hickey, et al., "Deep Brain Stimulation: A Paradigm Shifting Approach to Treat Parkinson's Disease," Frontiers in Neuroscience, Apr. 2016, vol. 10, Article 173, 11 pages.
Little, et al., "Adaptive Deep Brain Stimulation in Advanced Parkinson Disease," Ann Neurol 2013; Sep. 2013; 74: 449-457.
Little, et al., "Bilateral adaptive deep brain stimulation is effective in Parkinson's disease," J. Neurol Neurosurg Psychiatry; Oct. 26, 2015; 6 p.
Little, et al., "Controlling Parkinson's Disease with Adaptive Deep Brain Stimulation," J. Visualized Experiments, Jul. 16, 2014, 5 pp.
Little, et al., "What brain signals are suitable for feedback control of deep brain stimulation in Parkinson's disease?" Annals of the New York Academy of Sciences, Jul. 25, 2012; pp. 9-24.
Goetz, et al., "Movement Disorder Society-Sponsored Revision of the Unified Parkinson's Disease Ratings Scale (MDS-UPDRS): Scale Presentation and Clinimetric Testing Results," Movement Disorders, vol. 23, No. 15, Nov. 2008, pp. 2129-2170.
"MDS-UPDRS" Movement Disorder Society, Jul. 1, 2008, 32 pp.
U.S. Appl. No. 15/714,845, filed by Stanslaski, et al., filed Sep. 25, 2017.
U.S. Appl. No. 15/714,888, filed by Stanslaski, et al., filed Sep. 25, 2017.
Response to Office Action dated Oct. 30, 2019, from U.S. Appl. No. 15/714,888, filed Jan. 16, 2020, 15 pp.
Office Action from U.S. Appl. No. 15/714,845, dated Mar. 5, 2020, 10 pp.
Advisory Action from U.S. Appl. No. 15/714,888, dated May 13, 2020, 2 pp.
Final Office Action from U.S. Appl. No. 15/714,888, dated Mar. 5, 2020, 8 pp.
Response to Final Office Action dated Mar. 5, 2020, from U.S. Appl. No. 15/714,888, filed May 5, 2020, 15 pp.
Office Action from U.S. Appl. No. 15/714,888, dated Jun. 11, 2020, 9 pp.
Response to Office Action dated Mar. 5, 2020, from U.S. Appl. No. 15/714,845, filed Jun. 5, 2020, 9 pp.
Notice of Allowance from U.S. Appl. No. 15/714,845, dated Aug. 4, 2020, 5 pp.
Response to Office Action dated Jun. 11, 2020, from U.S. Appl. No. 15/714,888, filed Sep. 9, 2020, 11 pp.
U.S. Appl. No. 17/107,257, filed Nov. 30, 2020, naming inventors Stanslaski et al.

* cited by examiner

ADAPTIVE DEEP BRAIN STIMULATION USING MOVEMENT DESYNCHRONIZATION

This application claims the benefit of U.S. Provisional Application No. 62/400,605, by Stanslaski et al., entitled, "ADAPTIVE DEEP BRAIN STIMULATION USING HOMEOSTATIC WINDOW" and filed on Sep. 27, 2016, the entire content of which is incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

In general, the disclosure describes example medical devices, systems, and techniques for defining a therapeutic window Which defines boundaries for one or more parameters of electrical stimulation therapy delivered to a patient. The disclosure further describes techniques for sensing a signal of a patient and defining, based on the sensed signal, a homeostatic window. As described herein, the homeostatic window is used to control adjustment of the one or more parameters of the electrical stimulation to the patient. The disclosure further describes techniques for selecting a signal for use in defining the homeostatic window as described above by determining a response of the signal to at least one of the electrical stimulation therapy or a movement of the patient.

In one example, the techniques of the disclosure describe a method for delivering electrical stimulation therapy to a patient, the method comprising: delivering the electrical stimulation therapy to a tissue of a patient via electrodes; and adjusting a level of at least one parameter of the electrical stimulation therapy based on one of a first sensed signal of the patient and a second sensed signal of the patient, wherein the one of the first sensed signal of the patient and the second sensed signal of the patient is selected based on a first change in the first sensed signal in response to movement by the patient and a second change in the second sensed signal in response to the movement by the patient.

In another example, the techniques of the disclosure describe a medical device comprising: stimulation generation circuitry configured to deliver electrical stimulation therapy to tissue of a patient via electrodes; and processing circuitry configured to adjust a level of at least one parameter of the electrical stimulation therapy based on one of a first sensed signal of the patient and a second sensed signal of the patient, wherein the one of the first sensed signal of the patient and the second sensed signal of the patient is selected based on a first change in the first sensed signal in response to movement by the patient and a second change in the second sensed signal in response to the movement by the patient.

In another example, the techniques of the disclosure describe a medical device system comprising: means for delivering the electrical stimulation therapy to a tissue of a patient via electrodes; and means for adjusting a level of at least one parameter of the electrical stimulation therapy based on one of a first sensed signal of the patient and a second sensed signal of the patient, wherein the one of the first sensed signal of the patient and the second sensed signal of the patient is selected based on a first change in the first sensed signal in response to movement by the patient and a second change in the second sensed signal in response to the movement by the patient.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
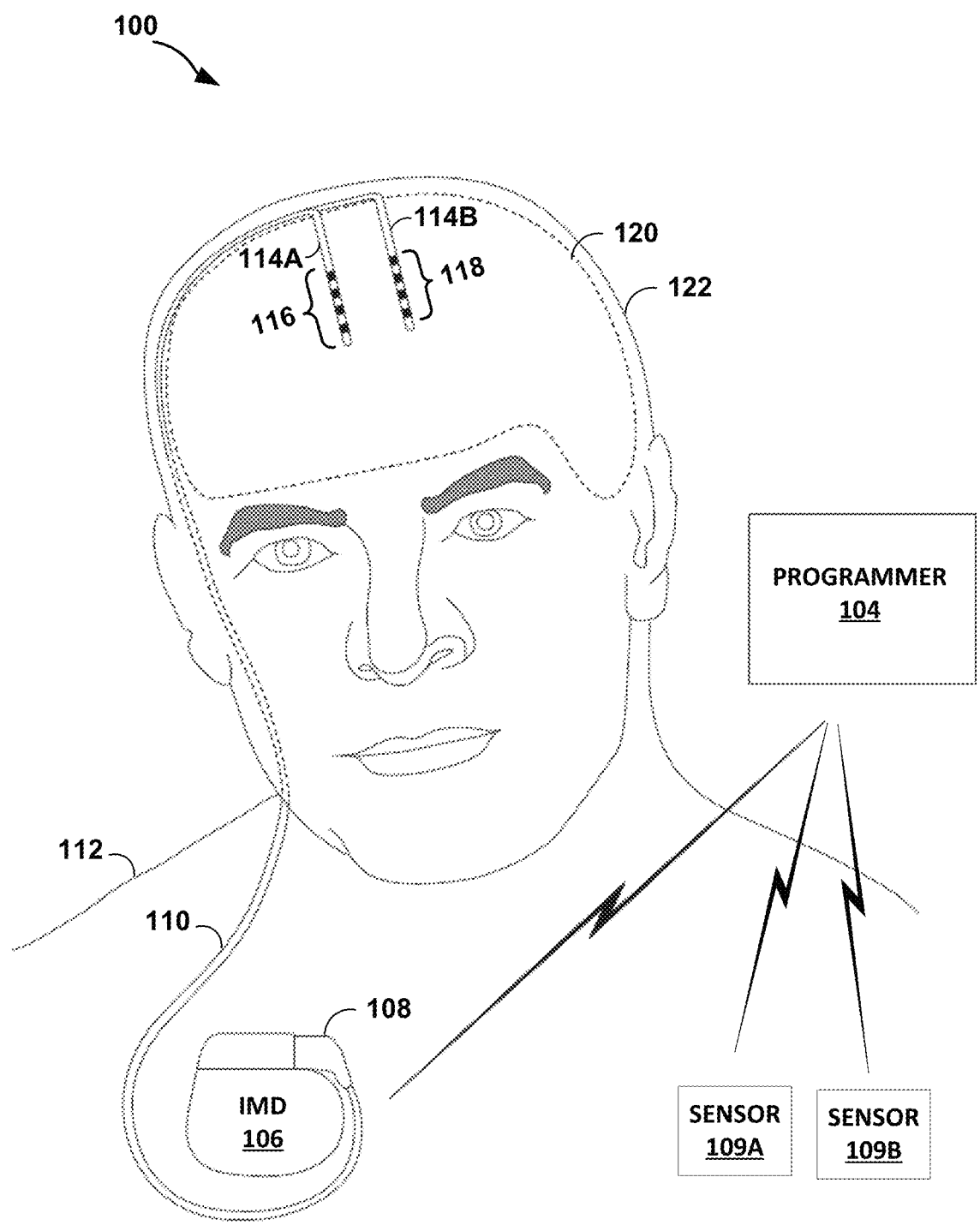
FIG. 1 is a conceptual diagram illustrating an example system that includes an implantable medical device (IMD) configured to deliver adaptive DBS to a patient according to an example of the techniques of the disclosure.

A patient may suffer from one or more symptoms treatable by electrical stimulation therapy. However, the severity of these symptoms may increase or decrease, for example, depending on various conditions such as the posture of the patient, the current activity of the patient (e.g., whether the patient is sleeping, exercising, working, or the like), the stress level of the patient, drug therapy or other therapy administered to the patient, and many other factors. Thus, a system that delivers electrical stimulation therapy at a constant magnitude may, in some circumstances, not deliver therapy that is sufficient to treat the symptoms of the patient over a range of conditions. Furthermore, in other circumstances, a constant-magnitude therapy delivery system may deliver a higher magnitude of electrical stimulation than is required to treat the symptoms of the patient, which may cause side effects in the patient and/or cause excessive power consumption by an implantable medical device (IMD).

Accordingly, in one example, a system including an IMD delivers electrical stimulation therapy having one or more parameters that may be selected and adjustable based on a homeostatic window defining lower and upper bounds for a sensed signal of the patient. In some examples, the sensed signal is a neurological signal of a patient, such as a neurological signal within the Beta frequency band or Gamma frequency band of the brain of the patient. In other examples, the sensed signal is representative of a physiological parameter of the patient sensed by one or more sensors of the system. In further examples, the system includes a therapeutic window that defines lower and upper bounds for one or more parameters of electrical stimulation delivered to the patient. While maintaining the one or more parameters of the electrical stimulation within the therapeutic window, the system may increase or decrease a magnitude of the one or more parameters of the electrical stimulation in response to changes in the sensed signal so as to maintain the sensed signal within the bounds of the homeostatic window. In this fashion, the system may use the sensed signal and the homeostatic window to control the magnitude of the one or more parameters of the electrical stimulation.

For example, while a patient is not taking medication selected to reduce one or more symptoms, a clinician determines a minimum magnitude of one or more parameters defining the electrical stimulation therapy, such as a minimum voltage amplitude or minimum current amplitude, sufficient to reduce the one or more symptoms. The clinician defines the upper bound of the homeostatic window as a magnitude of the sensed signal of the patient at this magnitude of the electrical stimulation therapy. Further, the clinician may determine a minimum magnitude of one or more parameters defining the electrical stimulation therapy, such as a minimum voltage amplitude or minimum current amplitude, sufficient to reduce or maintain reduction of one or more symptoms when the patient is taking medication selected to reduce the symptoms. The clinician defines a lower bound of the homeostatic window as the magnitude of the sensed signal of the patient at this magnitude of stimulation.

In an alternate example for setting the lower bound, while the patient is off medication, the clinician delivers electrical stimulation having one or more parameters that have a maximum magnitude (i.e., the upper bound of a therapeutic window, as described below), e.g., a maximum voltage amplitude or maximum current amplitude defined by a therapeutic window. In some examples, the clinician delivers electrical stimulation having a value for the one or more parameters slightly below the magnitude which induces side effects in the patient. Typically, delivering electrical stimulation at a magnitude slightly less than that which induces side effects causes maximal reduction of the one or more symptoms of the disease of the patient, and therefore maximal reduction of the signal. The clinician defines a lower bound of the homeostatic window as the signal of the patient at this magnitude of stimulation that is slightly less than that which induces side effects.

In a further example, the lower and upper bounds of the homeostatic window may be adjusted in response to patient input and/or one or more patient conditions. However, the values of one or more parameters defining the electrical stimulation therapy may be controlled to remain within a parameter range defined by lower and upper bounds of a therapeutic window. In one example, a patient may adjust one or more bounds of the homeostatic window to adjust delivery of electrical stimulation within a parameter range defined by the lower and upper bounds of the therapeutic window. In some examples, a patient may provide feedback to adjust one or both bounds of the homeostatic window.

In another example, the IMD may automatically adjust one or more parameters of the electrical stimulation within a parameter range defined by the lower and upper bounds of the therapeutic window, e.g., in response to the signal rising above an upper magnitude of the homeostatic window or falling below a lower magnitude of the homeostatic window. In further examples, the IMD may adjust one or both bounds of the homeostatic window based on the sensed signal. In this example, the system, via the IMD, delivers electrical stimulation to the patient, and may adjust one or more parameters defining the electrical stimulation within a parameter range defined by the lower and upper bounds of the therapeutic window based on the activity of the sensed signal within the homeostatic window. In some examples, the one or more parameters may be adjusted in a manner proportional to the magnitude of the sensed signal, e.g., directly proportional or inversely proportional.

The techniques of the disclosure may provide one or more advantages over other techniques that merely use a neurological signal, such a signal within a Beta frequency band of the brain of the patient, as a threshold in that the techniques of the disclosure may allow the signal of the patient to be maintained within a homeostatic window. This may help prevent the system from using excessive processing and reduce current drain in the system by preventing the system from continuously ramping up and down the magnitude of electrical stimulation, or from continuously oscillating the parameters of the electrical stimulation. Thus, such a system may allow for reduced power consumption and enhanced battery life. Further, in some examples, a system according to the techniques of the disclosure may reduce side effects experienced by a patient by allowing the system to remain at constant magnitudes of electrical stimulation for longer periods of time while the sensed signal is maintained within the homeostatic window. Furthermore, in some examples, a system of the present disclosure may not only deliver therapy targeted to a specific patient, but also permit adjustment of the therapy such that the therapy is tailored to a range of conditions relating to the behavior and activity of the patient. Thus, a system as described in this disclosure may provide adaptive therapy that is better suited to the changing needs and activity magnitudes of the patient than other methods of adaptive DBS.

Furthermore, in examples where the bounds of the homeostatic window are defined by a neurological signal of the brain of the patient, the correlation of the homeostatic window to the severity of symptoms in the patient may depend on which neurological signal is selected for use. For example, within a single frequency band of the neurological signal, a patient may demonstrate multiple peaks of responsiveness to electrical stimulation, each peak located at a different sub-band of the frequency band. Further, each of these sub-bands may respond differently to the electrical stimulation. For example, electrical stimulation may cause a first peak magnitude at a first sub-band to substantially diminish, while the same electrical stimulation may cause a second peak magnitude at a second sub-band to decrease only slightly. Additionally, movement of a patient may cause the neurological signal to desynchronize (e.g., diminish in magnitude in the presence of the movement). For example, movement by the patient may cause a first peak magnitude at a first sub-band to substantially diminish, i.e., decrease in magnitude substantially, while the same movement may cause a second peak magnitude at a second sub-band to decrease only slightly relative to the decrease in the first peak magnitude in the first sub-band.

In accordance with the techniques of the disclosure, techniques are disclosed for selecting a sub-band of the frequency band for use as a control signal for controlling one or more parameters defining the electrical stimulation or to define the bounds of the homeostatic window. In one example, a signal in a selected sub-band is selected for use as a control signal for controlling one or more parameters defining the electrical stimulation or to define the bounds of the homeostatic window by determining the sub-band that demonstrates the least response to electrical stimulation. In another example, a sub-band is selected for use as a control signal for controlling one or more parameters defining the electrical stimulation or to define the bounds of the homeostatic window by determining one of a plurality of sub-bands that demonstrates the least desynchronization response to movement by the patient, relative to one or more other sub-bands.

FIG. 1 is a conceptual diagram illustrating an example system 100 that includes an implantable medical device (IMD) 106 configured to deliver adaptive deep brain stimulation to a patient 112. DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient, etc. For example, one or more sensed signals of the patient may be used as a control signal such that the IMD 106 correlates the magnitude of the one or more parameters of the electrical stimulation to the magnitude of the one or more sensed signals. According to the techniques of the disclosure, system 100, via IMD 106, delivers electrical stimulation therapy having one or more parameters, such as voltage or current amplitude, adjusted in response to a signal deviating from a range defined by a homeostatic window. In one example, an upper bound of the homeostatic window is defined as the magnitude of the signal when electrical stimulation therapy, via IMD 106, is delivered to the brain 120 of patient 112 at a magnitude of one or more parameters defining the electrical stimulation therapy, such as a voltage or current amplitude, at which further increase to the magnitude of one or more parameters defining the electrical stimulation therapy does not cause a further reduction in the severity of the symptoms, when the patient is not taking medication selected to reduce the symptoms (as described in more detail below). Further, the lower bound of the homeostatic window is defined as the magnitude of the signal when electrical stimulation therapy, via IMD 106, is delivered to the brain 120 of patient 112 at a minimum magnitude of one or more parameters defining the electrical stimulation therapy, such as a minimum voltage or current amplitude, that is sufficient to reduce or maintain reduction of one or more symptoms while the patient is taking medication selected to reduce the symptoms (as described in more detail below). In some examples, the signal is a neurological signal, such as a signal within a Beta frequency band of the brain 120 of patient 112 or another signal that is considered a proportional signal, meaning that the signal increases as stimulation increases and decreases as stimulation decreases. In other examples, the signal may be an inversely proportional signal, meaning that the signal decreases as stimulation increases and increase as stimulation decreases, such as a signal within a Gamma frequency band of the brain 120 of patient 112. However, the techniques of the disclosure provide for other physiological or neurological signals to be used to define the homeostatic window for delivering therapy.

In yet further examples, the system delivers electrical stimulation therapy having the one or more parameters, such as voltage or current amplitude, adjusted in response to multiple signals, each signal deviating from a range defined by a respective homeostatic window. For example, the system may sense a first neurological signal, such as a signal within a Beta frequency band of the brain 120 of patient 112 within a first respective homeostatic window and a second neurological signal, such as a signal within a Gamma frequency band of the brain 120 of patient 112 within a second respective homeostatic window. In one example system, IMD 16 dynamically selects one of the first signal or the second signal for controlling adjustment of the one or more parameters based on a determination of which of the first signal or second signal most accurately corresponds to the severity of one or more symptoms of the patient. In another example system, IMD 106 adjusts the one or more parameters based on a ratio of the first signal to the second signal.

In some examples, the medication taken by patient 112 is a medication for controlling one or more symptoms of Parkinson's disease, such as tremor or rigidity due to Parkinson's disease. Such medications include extended release forms of dopamine agonists, regular forms of dopamine agonists, controlled release forms of carbidopa/levodopa (CD/LD), regular forms of CD/LD, entacapone, rasagiline, selegiline, and amantadine. Typically, to set the upper bound of the homeostatic window, the patient has been off medication, i.e., the upper bound is set when the patient is not taking medication selected to reduce the symptoms. The patient may be considered to be not taking the medication when the patient, prior to the time the upper bound is set, has not taken the medication for at least approximately 72 hours for extended release forms of dopamine agonists, the patient has not taken the medication for at least approximately 24 hours for regular forms of dopamine agonists and controlled release forms of CD/LD, and the patient has not taken the medication for at least approximately 12 hours for regular forms of CD/LD, entacapone, rasagiline, selegiline, and amantadine. Further, typically, to set the lower bound of the homeostatic window, at the time the lower bound is set, the patient has been on medication, e.g., taken the medication at prescribed dosages and intervals, for at least approximately 72 hours for extended release forms of dopamine agonists, the patient has been on medication, e.g., taken the medication at prescribed dosages and intervals, for at least approximately 24 hours for regular forms of dopamine agonists and controlled release forms of CD/LD, and the patient has been on medication, e.g., taken the medication at prescribed dosages and intervals, for at least approximately 12 hours for regular forms of CD/LD, entacapone, rasagiline, selegiline, and amantadine.

As described herein, "reducing" or "suppressing" the symptoms of the patient refer to alleviating, in whole or in part, the severity of one or more symptoms of the patient. In one example, a clinician makes a determination of the severity of one or more symptoms of Parkinson's disease of patient 112 with reference to the Unified Parkinson's Disease Rating Scale (UPDRS) or the Movement Disorder Society-Sponsored Revision of the Unified Parkinson's Disease Rating Scale (MDS-UPDRS). A discussion of the application of the MDS-UPDRS is provided by Movement Disorder Society-Sponsored Revision of the Unified Parkinson's Disease Rating Scale (MDS-UPDRS): Scale Presentation and Clinimetric Testing Results, C. Goetz et al, Movement Disorders, Vol. 23, No. 15, pp. 2129-2170 (2008), the content of which is incorporated herein in its entirety.

As described above, a clinician determines the upper bound of the homeostatic window while the patient is not taking medication, and while, via IMD 106, electrical stimulation therapy is delivered to the brain 120 of patient 112. In one example, a clinician determines the point at which increasing the magnitude of one or more parameters defining the electrical stimulation therapy, such as voltage amplitude or current amplitude, does not provide further reduction or suppression of one or more symptoms of the patient 112. For example, the clinician may gradually increase the magnitude of one or more parameters defining the electrical stimulation therapy and determine the point at which further increase to the magnitude of one or more parameters defining the electrical stimulation therapy does not cause a further reduction in the severity of the symptoms of Parkinson's disease, such as rigidity, in patient 112, as measured by a further reduction in the score of patient 112 under the UPDRS or MDS-UPDRS.

In another example, the clinician measures a physiological parameter of patient 112 related to one or more symptoms of the disease of patient 112 and determines the point at which further increase to the magnitude of one or more parameters defining the electrical stimulation therapy does not cause a further positive effect in the reduction of the one or more symptoms of the disease of patient 112. For example, the clinician may measure a wrist flexion of patient 112, which correlates to rigidity in patient 112, and determines the point at which further increase to the magnitude of one or more parameters defining the electrical stimulation therapy does not cause a further positive effect in the wrist flexion of patient 112. Other examples of physiological parameters may include signals from an accelerometer indicative of a tremor of patient 112. At this magnitude of the one or more parameters defining the electrical stimulation therapy, at which further increase in magnitude does not cause further reduction in severity of symptoms, the clinician measures the magnitude of the signal of the patient 112 and sets this magnitude as the upper bound of the homeostatic window. In some examples, the clinician may select an upper bound of the homeostatic window to be a predetermined amount, e.g., 5% or 10%, lower than the magnitude at which the symptoms of the patient 112 receive no further reduction in response to increased magnitude of one or more parameters defining the electrical stimulation therapy. In some examples, setting the upper bound to be lower than the measured magnitude may serve to select therapy parameter magnitude that prevents, during subsequent use, discomfort to patient 112 due to side effects of the therapy, and/or unnecessary consumption of power resources.

As also described above, a clinician determines the lower bound of the homeostatic window while the patient is taking medication, and while, via IMD 106, electrical stimulation therapy is delivered to the brain 120 of patient 112. In one example, a clinician determines the point at which decreasing the magnitude of one or more parameters defining the electrical stimulation therapy causes break-through of one or more symptoms of the patient 112. This break-through of symptoms may refer to re-emergence of at least some symptoms that were substantially suppressed up to the point of re-emergence due to the decrease in magnitude of the one or more electrical stimulation therapy parameters. For example, the clinician may gradually decrease the magnitude of one or more parameters defining the electrical stimulation therapy and determine the point at which the symptoms of Parkinson's disease in patient 112 emerge, as measured by sudden increase with respect to tremor or rigidity, in the score of patient 112 under the UPDRS or MDS-UPDRS. In another example, the clinician measures a physiological parameter of patient 112 correlated to one or more symptoms of the disease of patient 112. (e.g., wrist flexion of patient 112) and determines the point at which further decrease to the magnitude of one or more parameters defining the electrical stimulation therapy causes a sudden increase in the one or more symptoms of the disease of patient 112 (e.g., onset of lack of wrist flexion of patient 112).

At the magnitude of one or more parameters defining the electrical stimulation therapy at which further decrease to the magnitude of one or more parameters defining the electrical stimulation therapy causes a sudden increase in the one or more symptoms of the disease of patient 112, the clinician measures the magnitude of the signal of the patient 112 and sets this magnitude as the lower bound of the homeostatic window. In some examples, the clinician may select a lower bound of the homeostatic window to be a predetermined amount, e.g., 5% or 10%, higher than the magnitude at which the symptoms of the patient 112 first emerge during decrease in the magnitude of one or more electrical stimulation parameters to prevent emergence of the symptoms of the patient 112 during subsequent use.

In another example, the clinician sets the lower bound by first ensuring that the patient is off medication for the one or more symptoms. In this example, the clinician delivers electrical stimulation having a value for the one or more parameters approximately equal to the upper bound of the therapeutic window. In some examples, the clinician delivers electrical stimulation having a value for the one or more parameters slightly below the magnitude which induces side effects in the patient 112. Typically, this causes maximal reduction of the one or more symptoms of the disease of the patient 112, and therefore maximal reduction of the signal. At this magnitude of the one or more parameters, the clinician measures the magnitude of the signal of the patient 112 and sets, via external programmer 104, this magnitude as the lower bound of the homeostatic window. In some examples, the clinician may select a value for the lower bound of the homeostatic window to be a predetermined amount, e.g., 5% or 10%, lower than the magnitude at which the symptoms of the patient 112 emerge to prevent emergence of the symptoms of the patient 112 during subsequent use.

In still further examples, the clinician sets the upper bound and the lower bound as a ratio of one another. For example, the clinician may set a value for the upper bound as described above, and set a value for the lower bound as a percentage or proportion of the upper bound. In another example, the clinician may set a value for the lower bound as described above, and set a value for the upper bound as a percentage or proportion of the lower bound. In yet a further example, the clinician sets at least one of the upper bound at a maximum amplitude of the signal of patient 112 during phase amplitude coupling and the lower bound at a minimum amplitude of the signal of patient 112 during phase amplitude coupling.

In the aforementioned manner, upper and lower bounds may be set for a proportional signal. A signal is considered a proportional signal if a change in the signal magnitude will trigger system 100 to make a corresponding change in the therapy delivered by the system. An example proportional signal includes a neurological signal such as a signal within a Beta frequency band of brain 120 of patient 112. The Beta frequency band is about 13 Hertz to about 30 Hertz. For instance, system 100 may be configured such that, in response to sensing a decrease in signal magnitude for a proportional signal, a magnitude of therapy (e.g., stimulation voltage or current amplitude) may be decreased by system 100. Conversely, system 100 may be configured such that, in response to sensing an increase in signal magnitude, a magnitude of therapy may be increased by system 100. Other signals, including neurological signals such as a signal within the Gamma frequency band of brain 120 of patient 112, are inversely proportional signals. The Gamma frequency band is about 35 Hertz to about 200 Hertz. A high magnitude of such inversely proportional signals may correlate to the presence of side effects, such as dyskinesia. For these inversely proportional signals, system 100 may be configured such that, in response to sensing an increase in the sensed signal magnitude, IMD 106 may decrease a magnitude of one or more parameters of the electrical stimulation therapy, and in response to sensing a decrease in the sensed signal magnitude, IMD 106 may increase the magnitude of one or more parameters of the electrical stimulation therapy. As described herein, the magnitude of a sensed neurological signal, such as a signal within a Beta or Gamma frequency range, refers to a spectral power of the neurological signal.

For signals such as neurological signals within the Gamma frequency band that are inversely proportional, the setting of upper and lower bounds of a homeostatic window is accomplished in a manner similar to the way in which the lower and upper bounds, respectively, of a homeostatic window are set for proportional signals. This is discussed further below.

According to the techniques of the disclosure, the therapeutic window defines a parameter range for one or more parameters defining the electrical stimulation. A clinician may set an upper bound for the therapeutic window as a maximum value of one or more parameters defining the electrical stimulation. In an example of a voltage-controlled system, the clinician sets the upper bound of the therapeutic window as a maximum voltage amplitude of the electrical stimulation that the system may not exceed. In an example of a current-controlled system, the clinician sets the upper bound of the therapeutic window as a maximum current amplitude of the electrical stimulation that the system may not exceed. Typically, the upper bound of the therapeutic window is a maximum safe magnitude of the stimulation. In other words, the upper bound of the therapeutic window is a magnitude substantially below a pain threshold or a tissue injury threshold of the patient. However, in some cases, the upper bound of the therapeutic window is the highest magnitude of the stimulation that does not cause discomfort to the patient.

A clinician may set a lower bound for the therapeutic window as a minimum of one or more parameters defining the electrical stimulation. In one example, a clinician sets the lower bound for the therapeutic window as a minimum threshold magnitude of electrical stimulation that the system should continuously provide to the patient for effective therapy to substantially suppress symptoms. In an example of a voltage-controlled system, the clinician sets the lower bound of the therapeutic window as a minimum voltage amplitude of the electrical stimulation that the system should continuously provide to the patient to suppress symptoms. In an example of a current-controlled system, the clinician sets the lower bound of the therapeutic window as a minimum current amplitude of the electrical stimulation that the system should continuously provide to the patient for therapy to suppress symptoms.

Additionally, in one example of the techniques of the disclosure, the system monitors a signal of the patient. In one example, the signal is a neurological signal of a patient, such as a signal within a Beta frequency band or a Gamma frequency band of the brain of the patient. In another example, the signal is a transformation of a neurological signal of a patient that correlates to a probability that the patient will experience an event, such as a seizure or fall. In yet a further example, the signal is a signal indicative of a physiological parameter of the patient, such as a severity of a symptom of the patient, a posture of the patient, a respiratory function of the patient, or an activity level of the patient.

The system, via the delivers electrical stimulation to the patient, wherein one or more parameters defining the electrical stimulation are proportional to the magnitude of the monitored signal.

As an example wherein the signal is a signal within a Beta frequency band of brain 120 of patient 112, system 100 monitors the Beta band signal magnitude of patient 112. Upon detecting that the beta magnitude of patient 112 exceeds the upper bound of the homeostatic window, the system increases stimulation, e.g., increases stimulation voltage or current amplitude. The stimulation may be increased at a maximum ramp rate determined by the clinician, until the beta magnitude returns to a magnitude within the homeostatic window, or until the magnitude of the electrical stimulation reaches an upper limit of a therapeutic window determined by the clinician. Upon detecting that the beta magnitude of patient 112 falls below the lower bound of the homeostatic window, the system decreases stimulation, e.g., decreases stimulation voltage or current amplitude. The stimulation may be decreased at a maximum ramp rate determined by the clinician, until the beta magnitude returns to a magnitude within the homeostatic window, or until the magnitude of the electrical stimulation reaches a lower limit of a therapeutic window determined by the clinician. Upon detecting that the beta magnitude has returned to within the bounds of the homeostatic window, the system may hold the magnitude of the electrical stimulation constant. In this manner, while maintaining the one or more parameters of the electrical stimulation within the therapeutic window, the system may increase or decrease a magnitude of the one or more parameters of the electrical stimulation in response to changes in the sensed signal so as to maintain the sensed signal within the bounds of the homeostatic window. In this fashion, the system may use the sensed signal and the homeostatic window to control the magnitude of the one or more parameters of the electrical stimulation. Additional example implementations of the homeostatic window are provided in further detail below.

In some examples, the maximum ramp rate is a parameter set by the clinician. For example, a clinician may determine the tolerance of a patient 112 to a change in magnitude of the electrical stimulation over a period of time and set the maximum ramp rate to accommodate the comfort of patient 112. Further, as the rate of change of one or more parameters of electrical stimulation increases, some systems may lose resolution in the ability to detect control signals, such as the signal of patient 112. Thus, in some examples, the clinician may set the maximum ramp rate as a maximum ramp rate achievable by system 100 while still reliability detecting one or more neurological signals of patient 112. In some examples, the maximum ramp rate is at least approximately 0.1 Volts per 400 milliseconds. In some examples, the clinician titrates a plurality of ramps, such as 0.1 Volts per 400 milliseconds; 0.5 Volts per 400 milliseconds; 1 Volt per 400 milliseconds; and 2 Volts per 400 milliseconds, and selects a maximum ramp rate based on the tolerance of the patient and the reliability of the system 100.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 104 is described as delivering electrical stimulation therapy to brain 120, IMD 106 may be configured to direct electrical stimulation to other anatomical regions of patient 112. In other examples, system 100 may include an implantable drug pump in addition to, or in place of, IMD 106. Further, an IMD may provide other electrical stimulation such as spinal cord stimulation to treat a movement disorder.

According to the techniques of the disclosure, system 100 defines a homeostatic window and a therapeutic window for delivering adaptive DBS to patient 112. System 100 may adaptively deliver electrical stimulation and adjust one or more parameters defining the electrical stimulation within a parameter range defined by the lower and upper bounds of the therapeutic window based on the activity of the sensed signal within the homeostatic window. For example, system 100 may adjust the one or more parameters defining the electrical stimulation in response to the sensed signal falling below the lower bound or exceeding the upper bound of the homeostatic window, but may not adjust the one or more parameters defining the electrical stimulation such that they fall below the lower bound or exceed the upper bound of the therapeutic window.

In one example, external programmer 104 issues commands to IMD 106 causing DAD 106 to deliver electrical stimulation therapy via electrodes 116, 118 via leads 114. As described above, the therapeutic window defines an upper bound and a lower bound for one or more parameters defining the delivery of electrical stimulation therapy to patient 112. For example, the one or more parameters include a current amplitude (for a current-controlled system) or a voltage amplitude (for a voltage-controlled system), a pulse rate or frequency, and a pulse width. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. In one example, the therapeutic window defines an upper bound and a lower bound for one or more parameters, such as upper and lower bounds for a current amplitude of the electrical stimulation therapy (in current-controlled systems) or upper and lower bounds of a voltage amplitude of the electrical stimulation therapy (in voltage-controlled systems). While the examples herein are typically given with respect to adjusting a voltage amplitude or a current amplitude, the techniques herein may equally be applied to a homeostatic window and a therapeutic window using other parameters, such as, e.g., pulse rate or pulse width. Example implementations of the therapeutic window are provided in further detail below.

Additionally, in one example of the techniques of the disclosure, system 100 provides adaptive DBS. For example, system 100 may provide adaptive DBS by permitting a patient 112, e.g., via a patient programmer 104, to indirectly adjust the activation, deactivation, and magnitude of the electrical stimulation by adjusting the lower and upper bounds of the homeostatic window. For example, by adjusting one or both bounds of the homeostatic window, patient 112 may adjust the point at which the sensed signal deviates from the homeostatic window, triggering system 100 to adjust one or more parameters of the electrical stimulation within a parameter range defined by the lower and upper bounds of the therapeutic window.

In some examples, a patient may provide feedback, e.g., via programmer 104, to adjust one or both bounds of the homeostatic window. In another example, programmer 104 and/or IMD 106 may automatically adjust one or both bounds of the homeostatic window, as well as one or more parameters of the electrical stimulation within the parameter range defined by the lower and upper bounds of the therapeutic window. For example, IMD 106 may adjust the delivery of adaptive DBS by automatically adjusting one or more bounds of the homeostatic window, e.g., in response to a physiological parameter sensed by one or more sensors 109 of system 100. As a further example, programmer 104 and/or IMD 106 may automatically adjust one or more bounds of the homeostatic window based on one or more physiological or neurological signals of patient 112 sensed by IMD 106. For example, in response to deviations in the signal of the patient outside of the homeostatic window, system 100 (e.g., IMD 106 or programmer 104) may automatically adjust one or more parameters defining the electrical stimulation therapy delivered to the patient in a manner that is proportional to the magnitude of the sensed signal and within the therapeutic window defining lower and upper bounds for the one or more parameters. The adjustment to the one or more stimulation therapy parameters based on the deviation of the sensed signal may be proportional or inversely proportional to the magnitude of the signal.

Hence, in some examples, system 100, via programmer 104 or IMD 106, may adjust one or more parameters of the electrical stimulation, such as voltage or current amplitude, within the therapeutic window based on patient input that adjusts the homeostatic window, or based on one or more signals, such as sensed physiological parameters or sensed neurological signals, or a combination of two or more of the above. In particular, system 100 may adjust a parameter of the electrical stimulation, automatically and/or in response to patient input that adjusts the homeostatic window, provided the value of the electrical stimulation parameter is constrained to remain within a range specified by the upper and lower bounds of the therapeutic window. This range may be considered to include the upper and lower bounds themselves.

In some examples where system 100 adjusts multiple parameters of the electrical stimulation, system 100 may adjust at least one of a voltage amplitude or current amplitude, a stimulation frequency, a pulse width, or a selection of electrodes, and the like. In such an example, the clinician may set an order or sequence for adjustment of the parameters (e.g., adjust voltage amplitude or current amplitude, then adjust stimulation frequency, and then adjust the selection of electrodes). In other examples, system 100 may randomly select a sequence of adjustments to the multiple parameters. In either example, system 100 may adjust a value of a first parameter of the parameters of the electrical stimulation. If the signal does not exhibit a response to the adjustment of the first parameter, system 100 may adjust a value of a second parameter of the parameters of the electrical stimulation, and so on until the signal returns to within the homeostatic window.

Also, in some examples, system 100 may adjust the upper and/or lower bounds of the homeostatic window based on patient input, or based on one or more signals, such as sensed physiological parameters or sensed neurological signals, or a combination of two or more of the above. In this manner, system 100 may provide not only adaptive adjustment of one or more parameters of the electrical stimulation within the range defined by the therapeutic window, but also, in some examples, adaptive adjustment of the range of the homeostatic window itself, e.g., adjustment of the thresholds that cause system 100 to adaptively adjust the one or more parameters of the electrical stimulation, based on patient input, one or more sensed signals, or a combination of two or more of patient input. Hence, IMD 106 of system 100 may configured such that, adjustments to the upper and lower bounds of the homeostatic window, result in IMD 106 adjusting stimulation parameters within the therapeutic window. As an illustration, if a sensed physiological parameter of sensed neurological signal exceeds the upper bound or the homeostatic window or drops below the lower bound of the homeostatic window, system 100 may adjust values of one or more stimulation parameters to drive the sensed physiological parameter or sensed neurological signal back into the homeostatic window, e.g., subject to keeping the therapy parameter value within the range prescribed by the therapeutic window.

To adaptively adjust DBS based on a neurological signal, for example, two or more electrodes 116, 118 of IMD 106 may be configured to monitor a neurological signal of patient 112. In some examples, at least one of electrodes 116, 118 may be provided on a housing of IMD 106, providing a unipolar stimulation and/or sensing configuration. In one example, the neurological signal is a signal within a Beta frequency band of brain 120 of patient 112. For example, neurological signals within the Beta frequency band of patient 112 may correlate to one or more symptoms of Parkinson's disease in patient 112. Generally speaking, neurological signals within the Beta frequency of patient 112 may be approximately proportional to the severity of the symptoms of patient 112. For example, as tremor induced by Parkinson's disease increases, neurological signals within the Beta frequency of patient 112 increase. Moreover, neurological signals within the Beta frequency are considered proportional because system 100 may be configured such that an increase in signal magnitude may trigger system 100 to increase delivered stimulation therapy magnitude according to disclosed techniques. Similarly, as tremor induced by Parkinson's disease decreases, neurological signals within the Beta frequency of patient 112 decrease, and the decrease may trigger system 100 to decrease the magnitude of delivered stimulation.

In another example, the neurological signal monitored by IMD 106 may be a signal within a gamma frequency band of brain 120 of patient 112. Neurological signals within the Gamma frequency band of patient 112 may also correlate to one or more side effects in patient 112 resulting from electrical stimulation therapy. However, in contrast to neurological signals within the Beta frequency band, generally speaking, neurological signals within the Gamma frequency band of patient 112 may be approximately inversely proportional to the magnitude of stimulation magnitude that is delivered by system 100 in response to the signal. In other words, an elevated magnitude of the signal within the Gamma frequency band may indicate the presence of side effects, such as dyskinesia. For example, system 100 may be configured such that, as the magnitude of a signal within the Gamma frequency band increases, therapy magnitudes may be decreased by system 100 in response thereto, thereby reducing or eliminating side effects. Conversely, system 100 may be configured such that as the magnitude of a signal within the Gamma frequency band decreases, therapy magnitudes may be increased by system 100 according to techniques disclosed herein. Accordingly, IMD 106, in response to variations in the monitored neurological signal, e.g., such as real-time or near real-time variations, may deliver adaptive DBS to patient 112 by adjusting the magnitude of one or more parameters defining the electrical stimulation therapy, such as the voltage or current amplitude of electrical stimulation pulses. For example, IMD 106 may reduce a magnitude of a parameter, such as a current or voltage amplitude of the electrical stimulation therapy, in response to the magnitude of a monitored neurological signal within the Beta frequency band falling below the lower bound of the homeostatic window established for the Beta band signal. In this case, by falling below the lower bound of the homeostatic window, the Beta band signal indicates that symptoms are reduced, such that stimulation parameter magnitude likewise is reduced by IMD 106. Alternatively, IMD 106 may increase a magnitude of a stimulation parameter, such as a current or voltage amplitude of the electrical stimulation therapy, in response to the magnitude of the monitored signal within the Beta frequency band exceeding the upper bound of the homeostatic window. In this case, by exceeding the upper bound of the homeostatic window, the Beta band signal indicates that symptoms have increased to an undesirable amount, such that stimulation parameter magnitude is increased by IMD 106, e.g., to force the Beta band signal back into the homeostatic window, and thereby suppress or partially suppress symptoms.

Conversely, IMD 106 may be configured to increase a magnitude of a stimulation therapy parameter, such as a current or voltage amplitude of the electrical stimulation therapy, in response to the magnitude of a monitored signal within the Gamma frequency band falling below the lower bound of a homeostatic window established for the Gamma band signal. In this case, by falling below the lower bound of the homeostatic window, the Gamma band signal indicates that side effects have reduced, such that the stimulation parameter magnitude is increased by IMD 106. Alternatively, IMD 106 may reduce a magnitude of a stimulation parameter, such as a current or voltage amplitude of the electrical stimulation therapy, in response to the magnitude of a monitored signal within the Gamma frequency band rising above the upper bound of the homeostatic window. In this case, by exceeding the upper bound of the homeostasis window, the Gamma band signal indicates that side effects have increased to an undesirable amount, such that stimulation parameter magnitude is reduced by IMD 106, e.g., to force the Gamma band signal back into the homeostatic window and thereby suppress or partially suppress side effects. Further, while the magnitude of the monitored neurological signal remains within the homeostatic window, or when the magnitude of the monitored neurological signal returns to the homeostatic window, IMD 106 maintains the present magnitudes of the parameters defining the electrical stimulation. However, in this example, the IMD 106 is configured to ensure that any adjustments to the one or more parameters are within the bounds of the therapeutic window.

In further examples, IMD 106 determines a transformation of the neurological signal so as to determine a probability that the patient will experience an event, such as a seizure or a fall. In such an example, the clinician may set the upper bound and the lower bound of the homeostatic window to correspond to a maximum probability and a minimum probability that the patient will experience the event. For example, IMD 106 may reduce a magnitude of a parameter, such as a current or voltage amplitude of the electrical stimulation therapy, in response to the transformation falling below the lower bound of the homeostatic window. In this case, the transformation falling below the lower bound may indicate decreased probability that the patient will experience the event, such that stimulation parameter magnitude is reduced by IMD 106. Alternatively, IMD 106 may increase a magnitude of a parameter, such as a current or voltage amplitude of the electrical stimulation therapy, in response to the transformation exceeding the upper bound of the homeostatic window. In this case, the transformation exceeding the upper bound may indicate an increased probability that the patient will experience the event, such that stimulation parameter magnitude is increased by IMD 106.

In further examples, instead of, or in addition to, a neurological signal of patient 112, IMD 106 monitors, via one or more sensors, a physiological parameter. For example, the clinician may set lower and upper bounds for the homeostatic window using a sensed parameter indicative of tremor of patient 112 instead of a neurological signal. The IMD 106 may monitor, via an accelerometer, a tremor of patient 112. Accordingly, IMD 106, in response to variations in a monitored tremor signal, e.g., such as real-time or near real-time variations in amplitude or frequency of the tremor, may deliver adaptive DBS to patient 112 by adjusting the magnitude of one or more parameters defining the electrical stimulation therapy, such as the voltage or current amplitude of electrical stimulation pulses. For example, IMD 106 may reduce a magnitude of a parameter, such as a current or voltage amplitude of the electrical stimulation therapy, in response to the magnitude of a physiological parameter signal from an accelerometer, or other sensor, indicative of the tremor in patient 112 falling below the lower bound of the homeostatic window. In this case, the tremor signal falling below the lower bound may indicate a reduction in symptoms, such that stimulation parameter magnitude is reduced by IMD 106. Alternatively, IMD 106 may increase a magnitude of a parameter, such as a current or voltage amplitude of the electrical stimulation therapy, in response to the magnitude of a physiological parameter signal from an accelerometer indicative of the tremor in patient 112 exceeding the upper bound of the homeostatic window. In this case, the tremor signal exceeding the upper bound may indicate an increase in symptoms, such that stimulation parameter magnitude is increased by IMD 106. Further, while a signal from an accelerometer indicative of the tremor in patient 112 remains within the homeostatic window, or when the magnitude of signal from an accelerometer indicative of the tremor in patient 112 returns to the homeostatic window, IMD 106 maintains the present magnitudes of the parameters defining the electrical stimulation. However, IMD 106 ensures that any adjustments to the one or more parameters are within the bounds of the therapeutic window.

System 100 may use the therapeutic window to define an upper bound and a lower bound for one or more parameters defining the adaptive DBS. For example, system 100 may adjust current or voltage amplitude of the electrical stimulation therapy in response to patient input to the homeostatic window or variations in a sensed signal, but maintain the magnitude to be within a magnitude range defined by an upper magnitude bound and a lower magnitude bound of the therapeutic window. Typically, a clinician may set an upper bound for the therapeutic window as a maximum of one or more parameters defining the electrical stimulation. In an example of a voltage-controlled system, the clinician sets the upper bound of the therapeutic window as a maximum voltage amplitude of the electrical stimulation that the system may not exceed. In an example of a current-controlled system, the clinician sets the upper bound of the therapeutic window as a maximum current amplitude of the electrical stimulation that the system may not exceed. Typically, the upper bound of the therapeutic window is a maximum safe magnitude of the stimulation. In other words, the upper bound of the therapeutic window is a magnitude substantially below a pain threshold or a tissue injury threshold. In some examples, a clinician may alternatively or additionally determine the maximum safe magnitude to be a magnitude of the stimulation that does not cause side effects, or an undesirable degree of side effects, in the patient. However, in some cases, the upper bound of the therapeutic window is the highest magnitude of the stimulation that does not cause discomfort to the patient.

A clinician may set a lower bound for the therapeutic window as a minimum of one or more parameters defining the electrical stimulation. In one example, a clinician sets the lower bound for the therapeutic window to correspond to a minimum magnitude of stimulation that, when delivered at a continuous magnitude and frequency, is sufficient to suppress symptoms of the patient to at least a minimum degree on a substantially continuous basis. In an example of a voltage-controlled system, the clinician sets the lower bound of the therapeutic window as a minimum voltage amplitude of the electrical stimulation that the system should continuously provide to the patient. In an example of a current-controlled system, the clinician sets the lower bound of the therapeutic window as a minimum current amplitude of the electrical stimulation that the system should continuously provide to the patient for therapy. In some examples, the lower and upper bounds are inclusive (i.e., system 106 may select parameters defining the electrical stimulation within a range of values that are greater than or equal to the lower bound and less than or equal to the upper bound), while in other examples, the lower and upper bounds are exclusive (i.e., system 106 may select parameters defining the electrical stimulation within a range of values that are greater than but not equal to the lower bound and less than but not equal to the upper bound). Furthermore, while the patient may adjust the upper and lower bound of the homeostatic window to indirectly control one or more parameters defining the electrical stimulation, the patient typically is not permitted to adjust the upper and lower bound of the therapeutic window, e.g., out of safety concerns.

Thus, system 100, via IMD 106, by sensing the signal of the patient and adjusting one or more parameters of the electrical stimulation therapy such that the sensed signal remains within the homeostatic window, delivers electrical stimulation therapy that is adaptive, i.e., therapy that is moderated to the real-time severity of the one or more symptoms of patient 112. Thus, upon detecting that the severity of the one or more symptoms of patient 112 is increasing, e.g., as indicated by patient input sensed neurological signals, and/or sensed physiological parameter signals exceeding the upper bound of an applicable homeostatic window or windows, system 100 may ramp up the magnitude of one or more parameters defining the electrical stimulation therapy to ensure that the one or more symptoms of patient 112 remain controlled. Furthermore, upon detecting that the severity of the one or more symptoms of patient 112 is decreasing, e.g., as indicated by patient input, sensed neurological signals, and/or sensed physiological parameter signals, falling below the lower bound of the homeostatic window, system 100 may ramp down the magnitude of the one or more parameters defining the electrical stimulation therapy to reduce the likelihood of side effects to patient 112, as well as decrease power consumption and enhance the battery life of the IMD 106. Again, as an example, the one or more parameters may include current amplitude (for current-controlled systems) or voltage amplitude (for voltage-controlled systems) of stimulation.

As described above, the lower bound of the homeostatic window is set at the magnitude of the sensed signal, e.g., neurological signal or physiological parameter signal, during the minimum magnitude of electrical stimulation that was sufficient to prevent break-through of the symptoms of the patient while the patient was on medication. Further, the upper bound of the homeostatic window is set at the magnitude of the signal at which, while the patient was off medication (as described above), further increase to the magnitude of one or more parameters defining the electrical stimulation therapy does not cause a further reduction in the severity of the symptoms. Although, in some examples, the upper bound of the homeostatic window is set at the magnitude of the signal when electrical stimulation having a maximum magnitude of the one or more parameters is delivered to patient 112. By using the homeostatic window to heuristically define an upper bound and a lower bound as thresholds for adjusting the one or more parameters defining the electrical stimulation, the system 100 may ensure, via the lower and upper bounds of the homeostatic window, that the sensed signal, e.g., sensed neurological signal or sensed physiological parameter signal, floats within a range of expected behavior, and only triggers IMD 106 to make an adjustment to the one or more parameters defining the electrical stimulation when the signal deviates from the expected behavior.

Furthermore, the system 100 ensures, via the lower bound of the therapeutic window, that system 100 does not reduce the magnitude of electrical stimulation below a minimum magnitude that the clinician determined should be continuously delivered to the patient. Additionally, the system 100 ensures, via the upper bound of the therapeutic window, that system 100 does not increase the magnitude of electrical stimulation above a maximum magnitude that the clinician determined is safe and/or comfortable for the patient. By permitting adaptive adjustment of one or more stimulation parameters to maintain the sensed neurological signal or physiological parameter signal to remain in the homeostatic window, while constraining the values of the one or more parameters to reside within a range of values from the lower bound to the upper bound of the therapeutic window, system 100 may promote therapeutic efficacy and/or power efficiency. Further, the system 100 may avoid continuously adjusting, throttling, or oscillating the one or more stimulation parameters, avoiding excessive power drain on the system 100 without providing further treatment of the symptoms of the patient.

In another example, instead of the clinician, system 100 automatically defines parameters for the upper bound of the homeostatic window. In this example, sensors 109A-109B (collectively, "sensors 109") of system 100 measure the one or more symptoms while the patient 112 is off medication for the one or more symptoms. For example, sensors 109 may include one or more accelerometers for sensing signals used by programmer 104 or IMD 106 to determine rigidity due to Parkinson's disease by measuring wrist flexion of patient 112. Alternatively, the sensors 109 may include accelerometers for sensing signals used by programmer 104 or IMD 106 to measure the severity of tremors due to Parkinson's disease. IMD 106, in response to commands from external programmer 104, increases the one or more parameters until the electrical stimulation reduces the one or more symptoms to a predetermined threshold. In another example, IMD 106, in response to commands from external programmer 104, increases the one or more parameters until a point at which increasing the magnitude of the one or more parameters does not cause further alleviation of the one or more symptoms.

For example, programmer 104 may issue instructions to IMD 106 causing IMD 106 to increase the magnitude of one or more parameters of electrical stimulation therapy until the rigidity or tremors of patient 112 are eliminated or reduced by a predetermined degree, and the symptoms thereby reduced. Accordingly, programmer 104 measures the magnitude of the sensed signal, for example, the magnitude of beta in the brain 120 of patient 112 when the rigidity or tremors are eliminated or reduced by a predetermined degree, and sets this magnitude as the upper bound of the homeostatic window.

In another example, instead of the clinician, system 100 automatically defines parameters for the lower bound of the homeostatic window. In this example, sensors 109A-109B (collectively, "sensors 109") of system 100 measure the one or more symptoms while the patient 112 is on medication for the one or more symptoms (as described above). As described above, sensors 109 may include one or more accelerometers for sensing signals used by programmer 104 or IMD 106 to determine rigidity due to Parkinson's disease by measuring wrist flexion of patient 112. Alternatively, the sensors 109 may include accelerometers for sensing signals used by programmer 104 or IMD 106 to measure the severity of tremors due to Parkinson's disease. IMD 106, in response to commands from external programmer 104, decreases the one or more parameters until the electrical stimulation fails to treat the one or more symptoms. For example, the IMD 106 may decrease the one or more parameters until the symptoms of the patient 112 emerge, or until the severity of the symptoms increases to a predetermined threshold. For example, programmer 104 may issue instructions to IMD 106 causing IMD 106 to decrease the magnitude of one or more parameters of electrical stimulation therapy until the rigidity or tremors of patient 112 returns, or increases to a predetermined degree. Accordingly, programmer 104 measures the magnitude of the signal, for example, the magnitude of a neurological signal within the Beta frequency band in the brain 120 of patient 112, at a point which symptoms emerge or increase to a predetermined threshold, and sets this magnitude as the lower bound of the homeostatic window.

In the foregoing example, the one or more symptoms were symptoms of Parkinson's disease. However, in other implementations of the techniques of the disclosure, the one or more symptoms are symptoms resulting from other disorders, such as depression, epilepsy, chronic pain, or the like.

Additionally, in one example, patient 112, via external programmer 104, may provide feedback to adjust one or more bounds of the homeostatic window. For example, if patient 112 determines that the electrical stimulation therapy is not treating or not sufficiently treating the one or more symptoms of patient 112 effectively, patient 112 may provide feedback causing external programmer 104 to shift downward the upper bound of the homeostatic window, or shift the entire homeostatic window itself downward. To drive the signal to a lower window, the system increases the one or more parameters of the electrical stimulation therapy, and thereby increases the magnitude of electrical stimulation therapy to reduce the symptoms of the patient. In another example, if patient 112 determines that the electrical stimulation therapy is unpleasant, causes side effects, or is otherwise uncomfortable to patient 112, patient 112 may provide feedback causing external programmer 104 to shift upward the lower bound of the homeostatic window, or the shift entire homeostatic window itself upward. This has the effect of allowing the signal to float to a lower window, effectively causing the system 100 to decrease the one or more parameters of the electrical stimulation therapy, and thereby decreases the magnitude of electrical stimulation therapy to reduce side effects. While the patient 112 may adjust one or more bounds of the homeostatic window, or the homeostatic window itself, to ensure the safety of the patient, the patient 112 may not alter the therapeutic window that sets lower and upper bounds for the one or more parameters of the electrical stimulation therapy.

In another example, sensors 109 detect a physiological parameter of the patient, and in response to the physiological parameter, external programmer 104 automatically issues commands to IMD 106 to adjust one or both bounds of the homeostatic window. For example, in response to signals from sensors 109, external programmer 104 may determine that the magnitude of one or more parameters defining the electrical stimulation therapy is insufficient to reduce the one or more symptoms of patient 112. In this example, external programmer 104 may issue instructions to IMD 106 to shift downward the upper bound of the homeostatic window, or shift the entire homeostatic window itself downward. To drive the signal to a lower window, the system 100 effectively increases the one or more parameters of the electrical stimulation therapy, and thereby increases the magnitude of electrical stimulation therapy to reduce the symptoms of the patient. In another example, in response to signals from sensors 109, external programmer 104 may determine that, based on a symptom of the patient (e.g., tremor, rigidity, or wrist flexion), a posture of the patient (e.g., laying, sitting, standing, etc.) or an activity level of the patient (i.e., sleeping, walking, exercising, etc.), external programmer 104 should adjust the magnitude of one or more parameters defining the electrical stimulation therapy. External programmer 104 may issue instructions to IMD 106 to adjust the lower bound of the homeostatic window, the upper bound of the homeostatic window, or the entire homeostatic window itself. By allowing the signal to float at different magnitudes, system 100 effectively adjusts the one or more parameters of the electrical stimulation therapy, and thereby adjusts the magnitude of electrical stimulation therapy to compensate for different activity levels of patient 112. Typically, system 100 may not resize the therapeutic window beyond safety guidelines set by the clinician, which may be expressed as a maximum adjustment to upper bound, lower bound, or window shift, either in an absolute sense or in the sense of a maximum adjustment per unit time.

In some examples, each of sensors 109 is an accelerometer, a bonded piezoelectric crystal, a mercury switch, or a gyro. In some examples, sensors 109 may provide a signal that indicates a physiological parameter of the patient, which in turn varies as a function of patient activity. For example, the device may monitor a signal that indicates the heart rate, electrocardiogram (ECG) morphology, electroencephalogram (EEG) morphology, respiration rate, respiratory volume, core temperature, subcutaneous temperature, or muscular activity of the patient.

In some examples, sensors 109 generate a signal both as a function of patient activity and patient posture. For example, accelerometers, gyros, or magnetometers may generate signals that indicate both the activity and the posture of a patient 112. External programmer 104 may use such information regarding posture to determine whether external programmer 104 should perform adjustments to the therapeutic window.

For example, in order to identify posture, sensors 109 such as accelerometers may be oriented substantially orthogonally with respect to each other. In addition to being oriented orthogonally with respect to each other, each of sensors 109 used to detect the posture of a patient 112 may be substantially aligned with an axis of the body of a patient 112. When accelerometers, for example, are aligned in this manner, the magnitude and polarity of DC components of the signals generate by the accelerometers indicate the orientation of the patient relative to the Earth's gravity, e.g., the posture of a patient 112. Further information regarding use of orthogonally aligned accelerometers to determine patient posture may be found in a commonly assigned U.S. Pat. No. 5,593,431, which issued to Todd J. Sheldon, the entire content of which is incorporated by reference herein.

Other sensors 109 that may generate a signal that indicates the posture of a patient 112 include electrodes that generate a signal as a function of electrical activity within muscles of a patient 112, e.g., an electromyogram (EMG) signal, or a bonded piezoelectric crystal that generates a signal as a function of contraction of muscles. Electrodes or bonded piezoelectric crystals may be implanted in the legs, buttocks, chest, abdomen, or back of a patient 112, and coupled to one or more of external programmer 104 and IMD 106 wirelessly or via one or more leads. Alternatively, electrodes may be integrated in a housing of the IMD 106 or piezoelectric crystals may be bonded to the housing when IMD 106 is implanted in the buttocks, chest, abdomen, or back of a patient 112. The signals generated by such sensors when implanted in these locations may vary based on the posture of a patient 112, e.g., may vary based on whether the patient is standing, sitting, or lying down.

Further, the posture of a patient 112 may affect the thoracic impedance of the patient. Consequently, sensors 109 may include an electrode pair, including one electrode integrated with the housing of IMDs 106 and one of electrodes 116, 118, that generate a signal as a function of the thoracic impedance of a patient 112, and IMD 106 may detect the posture or posture changes of a patient 112 based on the signal. In one example (not depicted), the electrodes of the pair may be located on opposite sides of the patient's thorax. For example, the electrode pair may include electrodes located proximate to the spine of a patient for delivery of SCS therapy, and IMD 106 with an electrode integrated in its housing may be implanted in the abdomen or chest of patient 112. As another example, IMD 106 may include electrodes implanted to detect thoracic impedance in addition to leads 114 implanted within the brain of patient 112. The posture or posture changes may affect the delivery of DBS or SCS therapy to patient 112 for the treatment of any type of neurological disorder, and may also be used to detect patient sleep, as described herein.

Additionally, changes of the posture of a patient 112 may cause pressure changes with the cerebrospinal fluid (CSF) of the patient. Consequently, sensors 109 may include pressure sensors coupled to one or more intrathecal or intracerebroventricular catheters, or pressure sensors coupled to IMDs 106 wirelessly or via one of leads 114. CSF pressure changes associated with posture changes may be particularly evident within the brain of the patient, e.g., may be particularly apparent in an intracranial pressure (ICP) waveform.

Accordingly, in some examples, instead of monitoring a neurological signal of the patient, the system 100 monitors one or more signals from sensors 109 indicative of a magnitude of a physiological parameter of patient 112. Upon detecting that one or more signals from sensors 109 exceed the upper bound of the homeostatic window, the system 100 increases stimulation at a maximum ramp rate determined by the clinician until one or more signals from sensors 109 return to within the homeostatic window, or until the magnitude of the electrical stimulation reaches an upper limit of a therapeutic window determined by the clinician. Similarly, upon detecting that one or more signals from sensors 109 falls below the lower bound of the homeostatic window, the system decreases stimulation at a maximum ramp rate determined by the clinician until one or more signals from sensors 109 return to within the homeostatic window, or until the magnitude of the electrical stimulation reaches a lower limit of a therapeutic window determined by the clinician. Upon detecting that one or more signals from sensors 109 is within the bounds of the homeostatic window, the system holds the magnitude of the electrical stimulation constant.

Such a system 100 for delivering adaptive DBS to the patient by monitoring a physiological parameter may provide advantages over other techniques that use a neurological signal as a threshold in that the techniques of the disclosure allow an IMD to control delivery of therapy using hysteresis. In other words, such a system 100 uses the physiological parameter of the patient to create a control loop for not only controlling the delivery of therapy, but also controlling the magnitude of the delivered therapy. Such a system may be less intrusive on the activity of a patient because the system 100 adapts the stimulation to the current needs of the patient, and thus may reduce the side effects that the patient experiences.

Further, such a system 100 may use external sensors, such as accelerometers, instead of internal sensors, such as electrodes, to detect symptoms of the disease of the patient and control adjustments to the magnitude of one or more parameters of the therapy. For example, the system 100 may use a wrist sensor to detect wrist flexion or tremor of a patient suffering from Parkinson's disease. Thus, such an IMD the monitoring of a physiological parameter may be less invasive than other IMD systems because the system of the present disclosure may not require sensing electrodes to be implanted in the brain of the patient 112.

In some circumstances, system 100, as described herein, may deliver, based on the upper and lower bounds of the homeostatic window, a lower magnitude of electrical stimulation than patient 112 requires to prevent breakthrough of his or her symptoms. For example, a patient receiving therapy from an IMD 106 that controls delivery of electrical stimulation therapy using the homeostatic window may, in certain circumstances, experience results that are less optimal than if the patient received continuous electrical stimulation therapy at a maximum therapy magnitude. To prevent this occurrence, system 100 may determine a value for the at least one electrical stimulation parameter as defined by the homeostatic window, as described above. Further, the IMD 106 of system 100 may increase the value for the at least one electrical stimulation parameter by a bias amount greater than the determined magnitude defined by the homeostatic window so as to further prevent breakthrough of the symptoms of patient 112. Thus, system 100 may avoid delivering electrical stimulation therapy that is of a magnitude that may be insufficient for prevention of symptom breakthrough.

As one example of the biasing techniques described above, IMD 106 may determine an average value over time for the at least one parameter of the electrical stimulation (e.g., an average value over time of a voltage amplitude or a current amplitude) as defined by an average magnitude of the sensed signal within the homeostatic window. IMD 106 may further determine a bias amount for the at least one parameter of the electrical stimulation. In one example, the bias amount is a difference between the average value for the at least one parameter of the electrical stimulation, e.g., voltage or current amplitude, as defined by the average magnitude of the sensed signal, and a value for the at least one stimulation therapy parameter for an equivalent continuous (e.g., non-adaptive) electrical stimulation therapy continuously provided to the patient. In an example of a current-controlled system, the at least one parameter of the electrical stimulation is current amplitude, and the bias amount may be, for example, selected from a range of about 0.1 milliamps to about 5 milliamps (e.g., about 1 milliamp). In an example of a voltage-controlled system, the at least one parameter of the electrical stimulation is voltage amplitude, and the bias amount may be, for example, selected from a range of about 0.1 Volts to about 5 Volts (e.g., about 1 Volt). Upon delivering the electrical stimulation therapy, IMD 106 increases the value for the at least one parameter of the electrical stimulation as defined by the homeostatic window by the bias amount. In this fashion, IMD 106 may deliver electrical stimulation therapy with one or more stimulation parameter values selected to maintain the sensed psychological parameter or neurological signal within the homeostatic window while ensuring that the electrical stimulation therapy is as effective as continuous electrical stimulation therapy delivered at a maximum therapy magnitude.

In some examples, IMD 106 may determine the average value for the at least one parameter of the electrical stimulation and the bias amount on a periodic basis, such as a time period selected from a range of 1 second to 24 hours (e.g., every 30 seconds or every 10 minutes). In another example, the time period may correlate to a time course of medication and may be about 10 minutes to about 15 minutes. In other examples, a clinician may program the bias amount into a memory of IMD 106 or programmer 104. In such an example, the clinician may program the magnitude of the bias amount, such as selecting a magnitude for the bias amount from a range of bias amounts of about 0.5 milliamps to about 5 milliamps in a current controlled system. In another example, the clinician may specify how often the determination is performed, such as programming IMD 106 to recalculate the average value and the bias amount once after the expiration of a period of time selected from a range of about 10 seconds to 1 hour. In yet another example, the clinician may specify the length of time included in the determination of the average value of the stimulation parameter, such as averaging values for the at least one parameter of the electrical stimulation during a period of time selected from a range of the previous 20 seconds to the previous 5 minutes.

The architecture of system 100 illustrated in FIG. 1 is shown as an example. The techniques as set forth in this disclosure may be implemented in the example system 100 of FIG. 1, as well as other types of systems not described specifically herein. For example, a clinician may determine the upper bound and lower bound of the homeostatic window. In other examples, one of the external programmer 104 and IMD 104 determines the upper bound and lower bound of the homeostatic window. Furthermore, either external programmer 104 or IMD 106 may receive the signal representative of the signal of patient 112 and determine an adjustment to one or more parameters defining the electrical stimulation therapy that IMD 106 delivers to patient 112. Nothing in this disclosure should be construed so as to limit the techniques of this disclosure to the example architecture illustrated by FIG. 1.

Figure 2:
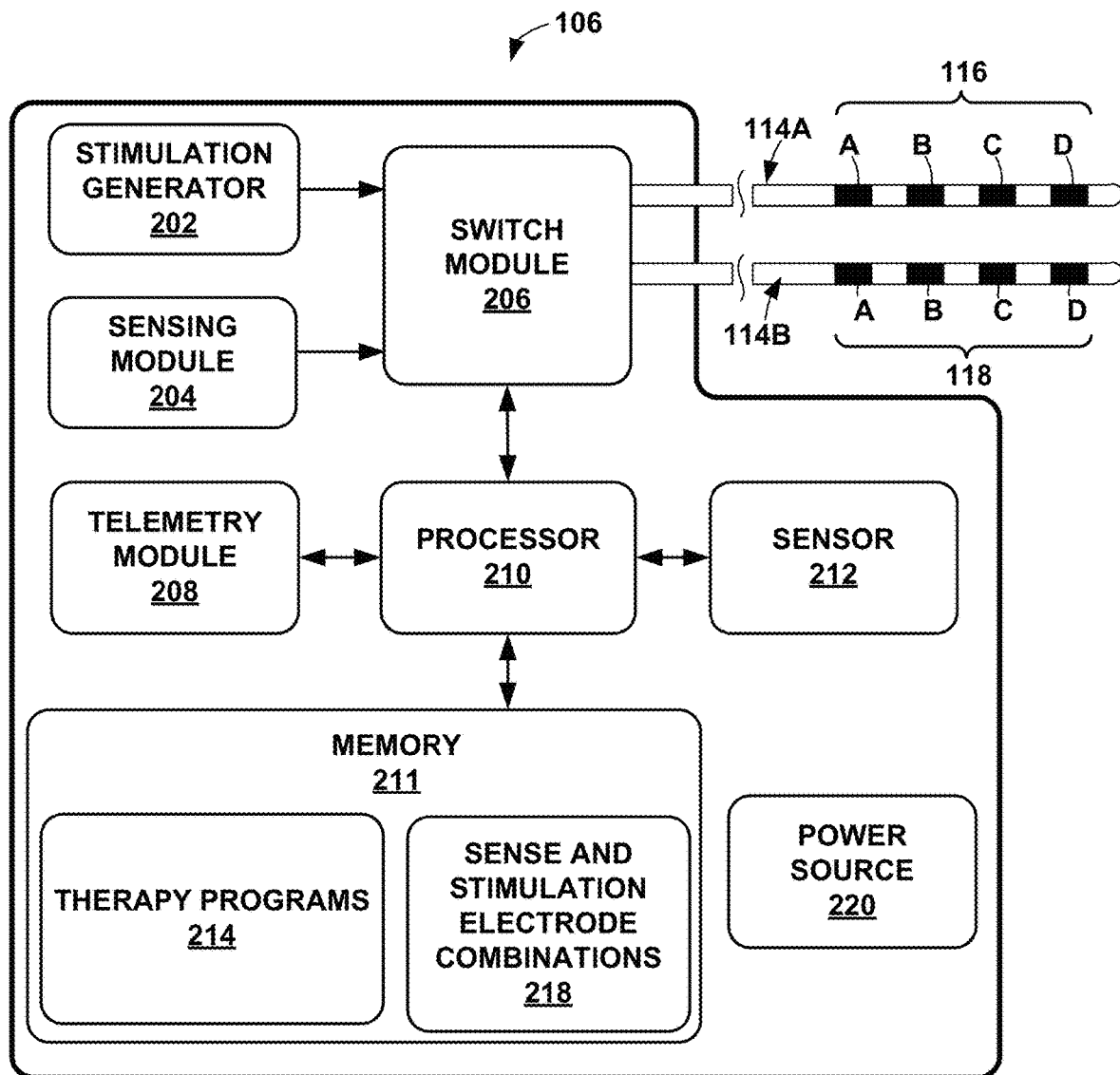
FIG. 2 is a block diagram of the example IMD of FIG. 1 for delivering adaptive DBS therapy according to an example of the techniques of the disclosure.

FIG. 2 is a block diagram of the example IMD 106 of FIG. 1 for delivering adaptive deep brain stimulation therapy. In the example shown in FIG. 2, IMD 106 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 40 to 185 Hertz or such as approximately 140 Hertz.

2. In the case of a voltage controlled system, Voltage Amplitude: between approximately 0.1 volts and approximately 50 volts, such as between approximately 2 volts and approximately 3 volts.

3. In the alternative case of a current controlled system, Current Amplitude: between approximately 0.2 milliamps to approximately 100 milliamps, such as between approximately 1.3 milliamps and approximately 2.0 milliamps.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above, subject to application of the upper and lower bounds of a therapeutic window to one or more of the parameters, such that an applicable parameter resides within the range prescribed by the window. Other ranges of therapy parameter values may also be useful, and may depend on the target stimulation site within patient 112. While stimulation pulses are described, stimulation signals may be of any form, such as continuous-time signals (e.g., sine waves) or the like.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 2, the set of electrodes 116 includes electrodes 116A, 116B, 116O, and 116D, and the set of electrodes 118 includes electrodes 118A, 118B, 118O, and 118D. Processor 210 also controls switch module 206 to apply the stimulation signals generated by stimulation generator 202 to selected combinations of electrodes 116, 118. In particular, switch module 204 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112. Alternatively, stimulation generator 202 may comprise multiple voltage or current sources and sinks that are coupled to respective electrodes to drive the electrodes as cathodes or anodes. In this example, IMD 106 may not require the functionality of switch module 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 106 and may communicate with processor 210 via wired or wireless communication techniques. Example neurological brain signals include, but are not limited to, a signal generated from local field potentials (LFPs) within one or more regions of brain 28. EEG and ECoG signals are examples of local field potentials that may be measured within brain 120. However, local field potentials may include a broader genus of electrical signals within brain 120 of patient 112.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers, electrodes 116, 118 interposed along leads 114 (and optionally switch module 206), electrical stimulation therapy to patient 112. The adaptive DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. In one example, the therapeutic window defines an upper bound and a lower bound for a voltage amplitude of the electrical stimulation therapy. In another example, the therapeutic window defines an upper bound and a lower bound for a current amplitude of the electrical stimulation therapy. In particular, a parameter of the electrical stimulation therapy, such as voltage or current amplitude, is constrained to a therapeutic window having an upper bound and a lower bound, such that the voltage or current amplitude may be adjusted provided the amplitude remains greater than or equal to the lower bound and less than or equal to the upper bound.

In one example, processor 210, via electrodes 116, 118 of IMD 106, monitors the behavior of a signal of patient 112 that correlates to one or more symptoms of a disease of patient 112 within a homeostatic window. Processor 210, via electrodes 116, 118, delivers to patient 112 adaptive DBS and may adjust one or more parameters defining the electrical stimulation within a parameter range defined by lower and upper bounds of a therapeutic window based on the activity of the sensed signal within the homeostatic window.

In one example, the signal is a neurological signal within the Beta frequency band of brain 120 of patient 112. The signal within the Beta frequency band of patient 112 may correlate to one or more symptoms of Parkinson's disease in patient 112. Generally speaking, neurological signals within the Beta frequency band of patient 112 may be approximately proportional to the severity of the symptoms of patient 112. For example, as tremor induced by Parkinson's disease increases, one or more electrodes 116, 118 detect an increase in the magnitude of neurological signals within the Beta frequency band of patient 112.

Similarly, as tremor induced by Parkinson's disease decreases, processor 210, via the one or more of electrodes 116, 118, detects a decrease in the magnitude of the neurological signals within the Beta frequency band of patient 112. In another example, the signal is a neurological signal within the Gamma frequency band of brain 120 of patient 112. The signal within the Gamma frequency band of patient 112 may also correlate to one or more side effects of the electrical stimulation therapy. However, in contrast to neurological signals within the Beta frequency band, generally speaking, neurological signals within the Gamma frequency band of patient 112 may be approximately inversely proportional to the severity of the side effects of the electrical stimulation therapy. For example, as side effects due to electrical stimulation therapy increase, processor 210, via the one or more of electrodes 116, 118, detects a decrease in the magnitude of the signal within the Gamma frequency band of patient 112. Similarly, as side effects due to electrical stimulation therapy decrease, processor 210, via the one or more of electrodes 116, 118, detects an increase in the magnitude of the signal within the Gamma frequency band of patient 112.

In response to detecting that the signal of the patient, e.g., a sensed physiological parameter signal or a sensed neurological signal, has deviated from the homeostatic window, processor 210 dynamically adjusts the magnitude of the one or more parameters of the electrical stimulation therapy such as, e.g., pulse current amplitude or pulse voltage amplitude, to drive the signal of the patient back into the homeostatic window. For example, wherein the signal is a neurological signal within the Beta frequency band of brain 120 of patient 112, processor 210, via the one or more of electrodes 116, 118, monitors the beta magnitude of patient 112. Upon detecting that the beta magnitude of patient 112 exceeds the upper bound of the homeostatic window, processor 210 increases a magnitude of the electrical stimulation delivered via electrodes 116, 118 at a maximum ramp rate determined by the clinician until the magnitude of the neurological signal within the Beta band falls back to within the homeostatic window, or until the magnitude of the electrical stimulation reaches an upper limit of a therapeutic window determined by the clinician. Similarly, upon detecting that the beta magnitude of patient 112 falls below the lower bound of the homeostatic window, processor 210 decreases stimulation magnitude at a maximum ramp rate determined by the clinician until the beta magnitude rises back to within the homeostatic window, or until the magnitude of the electrical stimulation reaches a lower limit of a therapeutic window determined by the clinician. Upon detecting that the beta magnitude is presently within the bounds of the homeostatic window, or has returned to within the bounds of the homeostatic window, processor 210 holds the magnitude of the electrical stimulation constant.

As another example, wherein the signal is a neurological signal within the Gamma frequency band of brain 120 of patient 112, processor 210, via the one or more of electrodes 116, 118, monitors the gamma magnitude of patient 112. Upon detecting that the gamma magnitude of patient 112 falls below the lower bound of the homeostatic window, processor 210 increases a magnitude of the electrical stimulation delivered via electrodes 116, 118 at a maximum ramp rate determined by the clinician until the gamma magnitude rises back to within the homeostatic window, or until the magnitude of the electrical stimulation reaches an upper limit of a therapeutic window determined by the clinician.

Similarly, upon detecting that the gamma magnitude of patient 112 rises above the upper bound of the homeostatic window, processor 210 decreases stimulation at a maximum ramp rate determined by the clinician until the gamma magnitude falls back to within the homeostatic window, or until the magnitude of the electrical stimulation reaches a lower limit of a therapeutic window determined by the clinician. Upon detecting that the gamma magnitude is presently within the bounds of the homeostatic window, or has returned to within the bounds of the homeostatic window, processor 210 holds the magnitude of the electrical stimulation constant.

In some examples, processor 210 continuously measures the signal in real time. In other examples, processor 210 periodically samples the signal according to a predetermined frequency or after a predetermined amount of time. In some examples, processor 210 periodically samples the signal at a frequency of approximately 150 Hertz.

Furthermore, processor 210 delivers electrical stimulation therapy that is constrained by an upper bound and a lower bound of a therapeutic window. In some examples, values defining the therapeutic window are stored within memory 211 of IMD 106. For example, in response to detecting that the signal has deviated from the homeostatic window, processor 210 of IMD 106 may adjust one or more parameters of the electrical stimulation therapy to provide responsive treatment to patient 112. For example, in response to detecting that the signal has exceeded an upper bound of the homeostatic window and prior to delivering the electrical stimulation therapy, processor 210 determines whether the adjustment to the one or more parameters is greater than an upper bound of the therapeutic window, and if so, reduces the one or more parameters to be at or below the magnitude of the upper bound. For example, in a voltage-controlled system wherein the clinician has set the upper bound of the therapeutic window to be 3 Volts, processor 210 determines whether the adjustment to the one or more parameters is greater than 3 Volts, and if so, sets the adjustment to be 3 Volts.

In another example, in response to detecting that the signal has fallen below a lower bound of the homeostatic window and prior to delivering the electrical stimulation therapy, processor 210 determines whether the adjustment to the one or more parameters is less than a lower bound of the therapeutic window, and if so, increases the one or more parameters to be at or above the magnitude of the lower bound. For example, in the above voltage-controlled system wherein the clinician has set the lower bound of the therapeutic window to be 2 Volts, processor 210 determines whether the adjustment to the one or more parameters is less than 2 Volts, and if so, sets the adjustment to be 2 Volts. Thus, processor 210 of DAD 106 may deliver adaptive DBS to patient 112 wherein the one or more parameters describing the adaptive DBS is within the therapeutic window.

In the foregoing example, the bounds of the therapeutic window are inclusive (i.e., the upper and lower bounds are valid values for the one or more parameters). However, in other examples, the bounds of the therapeutic window are exclusive (i.e., the upper and lower bounds are not valid values for the one or more parameters). In such an example of an exclusive therapeutic window, processor 210 instead sets the adjustment to the one or more parameters to be the next highest valid value (in the case of an adjustment potentially exceeding the upper bound) or the next lowest valid value (in the case of an adjustment potentially exceeding the lower bound).

In another example, values defining the therapeutic window are stored within a memory 311 of external programmer 104. In this example, in response to detecting that the signal has deviated from the homeostatic window, processor 210 of IMD 106 transmits, via telemetry module 208, data representing the measurement of the signal to external programmer 104. In one example, in response to detecting that the signal has exceeded an upper bound of the homeostatic window, processor 210 of IMD 106 transmits, via telemetry module 208, data representing the measurement of the signal to external programmer 104. External programmer 104 determines whether the adjustment to the one or more parameters is greater than an upper bound of the therapeutic window, and if so, reduces the one or more parameters to be at or below the magnitude of the upper bound. For example, in a voltage-controlled system wherein the clinician has set the upper bound of the therapeutic window to be 3 Volts, external programmer 104 determines whether the adjustment to the one or more parameters is greater than 3 Volts, and if so, instructs processor 210 of IMD 106 to set the adjustment to be 3 Volts.

In another example, in response to detecting that the signal has fallen below a lower bound of the homeostatic window, processor 210 of IMD 106 transmits, via telemetry module 208, data representing the measurement of the signal to external programmer 104. External programmer 104 determines whether the adjustment to the one or more parameters is less than a lower bound of the therapeutic window, and if so, reduces the one or more parameters to be at or above the magnitude of the lower bound. For example, in a voltage-controlled system wherein the clinician has set the lower bound of the therapeutic window to be 2 Volts, external programmer 104 determines whether the adjustment to the one or more parameters is less than 2 Volts, and if so, instructs processor 210 of IMD 106 to set the adjustment to be 2 Volts.

In another example, processor 210, via telemetry module 208 and from external programmer 104, receives instructions to adjust to one or more bounds of the therapeutic window. For example, such instructions may be in response to patient feedback on the efficacy of the electrical stimulation therapy, or in response to one or more sensors 109 that have detected a signal of the patient. Such signals from sensors 109 may include neurological signals, such as a signal within the Beta frequency band or signal within the Gamma frequency band of brain 120 of patient 112, or physiological parameters and measurements, such as a signal indicating one or more of a patient activity level, posture, and respiratory function. Further, such signals from sensors 109 may indicate a lack of reduction of one or more symptoms of the patient 112, such as tremor or rigidity or the presence of side effects due to electrical stimulation therapy, such as paresthesia. In response to these instructions, processor 210 may adjust one or more bounds of the homeostatic window. For example, processor 210 may adjust the magnitude of the upper bound, the lower bound, or shift the overall position of the homeostatic window such that the threshold, defined by the homeostatic window, for adjustment of the one or more parameters of electrical stimulation, is itself adjusted. Thereafter, processor 210, via electrodes 116 and 118, delivers the adjusted electrical stimulation to patient 112.

As one example, processor 210 receives, via telemetry module 208, an input from sensors 109 indicating a magnitude of wrist flexion. If the input indicates that the performance of the wrist flexion of patient 112 is below a therapeutic magnitude determined by the clinician and programmed into IMD 106 via external programmer 104, processor 210 adjusts the homeostatic window down. In some examples, processor 210 adjusts the lower and upper bound of the homeostatic window down by a predetermined amount, e.g., 5% or 10%, of their previous values. Processor 210 may maintain the homeostatic window at this new position until patient 112 performs a subsequent wrist flexion task. In some examples, processor 210 continues to adjust the homeostatic window down until the input from sensors 109 indicates that the wrist flexion of patient 112 reaches the therapeutic magnitude determined by the clinician.

For example, processor 206, via telemetry module 208, may receive from external programmer 104, information indicating feedback from a patient 112 to adjust one or more bounds of the homeostatic window. For example, processor 206, via telemetry module 208, receives instructions to shift downward the upper bound of the homeostatic window, or the entire homeostatic window itself. To drive the signal to a lower window, processor 206 increases the one or more parameters of the electrical stimulation therapy, and thereby increases the magnitude of electrical stimulation therapy to reduce the symptoms of the patient 112. In another example, processor 206, via telemetry module 208, receives instructions from external programmer 104 to shift upward the lower bound of the homeostatic window, or the entire homeostatic window itself. This has the effect of allowing the signal to float to a higher window, effectively causing the IMD 106 to decrease the one or more parameters of the electrical stimulation therapy, and thereby decrease the magnitude of electrical stimulation therapy to reduce side effects. While processor 206, in response to instructions from a patient 112, may adjust one or more bounds of the homeostatic window, or the homeostatic window itself, typically, to ensure the safety of the patient, processor 206 may not alter the therapeutic window that sets lower and upper bounds for the one or more parameters of the electrical stimulation therapy without the authorization of a clinician.

In another example, processor 206 receives a signal from sensors 109 indicative of a physiological parameter of the patient. In response to the physiological parameter, processor 206 adjusts one or both bounds of the homeostatic window. For example, in response to signals from sensors 109, processor 206 may determine that the magnitude of one or more parameters defining the electrical stimulation therapy is insufficient to reduce the one or more symptoms of patient 112. In this example, processor 206 shifts downward the upper bound of the homeostatic window, or the entire homeostatic window itself. In another example, in response to signals from sensors 109, processor 206 may determine that the magnitude of one or more parameters defining the electrical stimulation therapy may result in one or more side effects in patient 112. In this example, processor 206 shifts upward the lower bound of the homeostatic window, or the entire homeostatic window itself. In further examples, processor 206 adjusts the lower bound of the homeostatic window, the upper bound of the homeostatic window, or the entire homeostatic window itself. By allowing the signal to float at different magnitudes, the system 100 effectively adjusts the one or more parameters of the electrical stimulation therapy, and thereby adjusts the magnitude of electrical stimulation therapy to compensate for different activity levels of patient 112. Typically, processor 206 may not independently resize the therapeutic window beyond safety guidelines set by the clinician, which may be expressed as a maximum adjustment to upper bound, lower bound, or window shift, either in an absolute sense or in the sense of a maximum adjustment per unit time.

As described above, in one example, for a proportional neurological signal, such as a signal within the Beta frequency band, a clinician sets the upper bound of the homeostatic window as the magnitude of the sensed signal while receiving a minimum magnitude of electrical stimulation therapy sufficient to reduce one or more symptoms of the disease and while the patient is not receiving the medication for reduction of the one or more symptoms of the disease. Alternatively, the clinician may set the upper bound of the homeostatic window as the magnitude of the sensed signal while receiving electrical stimulation therapy and while the patient is not receiving the medication for reduction of the one or more symptoms of the disease, wherein the electrical stimulation is at a magnitude sufficient to reduce one or more symptoms of the disease or disorder but which, above the magnitude, no further substantial reduction in the one or more symptoms is achieved.

Further, in one example, for a proportional neurological signal, such as a signal within the Beta frequency band, the clinician sets the lower bound of the homeostatic window as a magnitude of the sensed signal while receiving a minimum magnitude of electrical stimulation therapy sufficient to reduce one or more symptoms of a disease and while the patient is receiving medication for reduction of one or more symptoms of a disease or disorder. Alternatively, the clinician may set the upper bound of the homeostatic window as the magnitude of the sensed signal while receiving electrical stimulation therapy sufficient to cause maximum reduction of the one or more symptoms of the disease or disorder without inducing substantial side effects in the patient and while the patient is not receiving the medication for reduction of the one or more symptoms of the disease. Note that, for an inversely proportional signal, such as a signal within the Gamma frequency band, the process for setting the upper and lower bounds is reversed.

By using the homeostatic window to heuristically define an upper bound and a lower bound as thresholds for adjusting the one or more parameters defining the electrical stimulation, processor 206 ensures, via the lower and upper bounds of the homeostatic window, that the neurological signal floats within a range of expected behavior, and only triggers adjustment to the one or more parameters defining the electrical stimulation when the neurological signal deviates from the expected behavior. It should be further noted that, while the lower and upper bounds are defined while the patient is either off medication or on medication, after defining the homeostatic window, electrical stimulation therapy is delivered according to the homeostatic window regardless of whether the patient is on or off medication.

Furthermore, the processor 206 ensures, via the lower bound of the therapeutic window, that IMD 106 does not reduce the magnitude of electrical stimulation below a minimum magnitude that the clinician determined should be continuously delivered to the patient. Additionally, processor 206 ensures, via the upper bound of the therapeutic window, that IMD 106 does not increase the magnitude of electrical stimulation above a maximum magnitude that the clinician determined is safe or comfortable for the patient. By permitting adaptive adjustment of one or more stimulation parameters, while constraining the values of the one or more parameters to reside within a range of values from the lower bound to the upper bound of the homeostatic therapeutic window, processor 206 may promote therapeutic efficacy and/or power efficiency. Further, the system 100 may avoid continuously adjusting, throttling, or oscillating the one or more stimulation parameters, avoiding excessive power drain on the system 100 without providing further treatment of the symptoms of the patient.

Thus, processor 210 may adjust the magnitude or magnitude of one or more parameters defining the electrical stimulation therapy only when the signal deviates from the homeostatic window to ensure that under normal conditions, the electrical stimulation remains constant, while still retaining the ability to dynamically increase or decrease the electrical stimulation to adapt to the needs of the patient.

Figure 3:
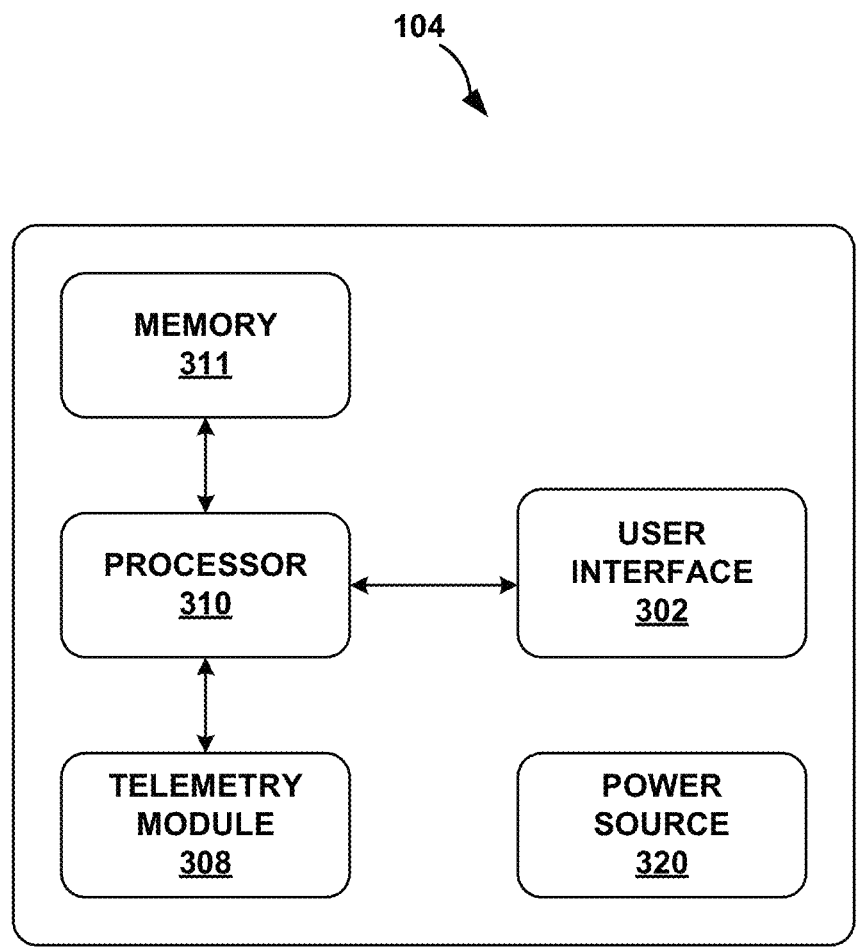
FIG. 3 is a block diagram of the external programmer of FIG. 1 for controlling delivery of adaptive DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an IF or proximal inductive medium. In some examples, telemetry module 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

According to the techniques of the disclosure, in some examples, processor 310 of external programmer 104 defines the parameters of a homeostatic therapeutic window, stored in memory 311, for delivering adaptive DBS to patient 112. In one example, processor 311 of external programmer 104, via telemetry module 308, issues commands to IMD 106 causing IMD 106 to deliver electrical stimulation therapy via electrodes 116, 118 via leads 114.

In one example, the homeostatic window has an upper bound and a lower bound that define an upper limit and a lower limit, respectively, for one or more parameters that define the electrical stimulation therapy that IMD 106 delivers to patient 112. For example, while the patient is not taking medication selected to reduce one or more symptoms, a clinician, via user interface 302 of external programmer 104, instructs IMD 106, via telemetry module 308, to gradually increase one or more parameters, such as a maximum voltage or current amplitude, defining the electrical stimulation therapy delivered to patient 112 to determine the point at which further increase to the magnitude of one or more parameters defining the electrical stimulation therapy results in the onset of side effects for the patient. The clinician, via user interface 302 of external programmer 104, defines the lower bound of the homeostatic window as a magnitude of the signal of the patient at this magnitude of electrical stimulation.

Further, while the patient is on medication selected to reduce the one or more symptoms, a clinician, via user interface 302 of external programmer 104, instructs IMD 106, via telemetry module 308, to gradually decrease the one or more parameters, such as a minimum voltage or current amplitude, defining the electrical stimulation therapy delivered to patient 112 to determine a minimum magnitude of the one or more parameters sufficient to reduce or maintain reduction of one or more symptoms without the symptoms breaking through or reemerging. The clinician, via user interface 302 of external programmer 104, may define this magnitude as a potential lower therapy limit for the device to adapt to when adaptive stimulation is running.

In another example, while the patient is off medication selected to reduce the one or more symptoms, sensors 109 measure the one or more symptoms and relay, via telemetry module 308, the measurements to processor 310 of external programmer 104. Processor 310 instructs IMD 106, via telemetry module 308, to gradually increase one or more parameters, such as a minimum voltage or current amplitude, defining the electrical stimulation therapy delivered to patient 112 to determine a minimum magnitude of the one or more parameters sufficient to reduce the one or more symptoms. Processor 310 defines the upper bound of the homeostatic window as a magnitude of the signal of the patient at this magnitude of electrical stimulation, and stores this value in memory 311.

Further, while the patient is on medication selected to reduce the one or more symptoms, sensors 109 measure the one or more symptoms and relay, via telemetry module 308, the measurements to processor 310 of external programmer 104. Processor 310 instructs IMD 106, via telemetry module 308, to gradually decrease the one or more parameters, such as a minimum voltage or current amplitude, defining the electrical stimulation therapy delivered to patient 112 to determine a minimum magnitude of the one or more parameters sufficient to reduce or maintain reduction of one or more symptoms without the symptoms breaking through or reemerging. Processor 310 defines the lower bound of the homeostatic window as a magnitude of the signal of the patient at this magnitude of electrical stimulation, and stores this value in memory 311.

Additionally, in one example, patient 112, via user interface 302, provides feedback to processor 310 indicating the efficacy of the electrical stimulation therapy. In response to the feedback, processor 310 adjusts one or more bounds of the homeostatic window. For example, if patient 112 determines that the electrical stimulation therapy is not treating the one or more symptoms of patient 112, patient 112 may provide feedback to external programmer 104 via user interface 302 to increase the electrical stimulation therapy. For example, if patient 112 determines that the electrical stimulation therapy is not treating the one or more symptoms of patient 112 effectively, patient 112 may provide feedback, via user interface 302, to processor 310, causing processor 310 to shift downward the upper bound of the homeostatic window, or the entire homeostatic window itself. To drive the sensed signal to a lower window, the processor 310 issues instructions, via telemetry module 308, to IMD 106 to increase the one or more parameters of the electrical stimulation therapy, and thereby increases the magnitude of electrical stimulation therapy to reduce the symptoms of the patient. In another example, if patient 112 determines that the electrical stimulation therapy is unpleasant, causes side effects, or is otherwise uncomfortable to patient 112, patient 112 may provide feedback, via user interface 302, to processor 310 causing processor 310 to shift upward the lower bound of the homeostatic window, or the entire homeostatic window itself. This has the effect of allowing the signal to float to a higher window, effectively causing IMD 106 to decrease the one or more parameters of the electrical stimulation therapy, and thereby decreases the magnitude of electrical stimulation therapy to reduce side effects. While the patient 112 may adjust one or more bounds of the homeostatic window, or the homeostatic window itself, typically, to ensure the safety of the patient, the patient 112 may not alter the therapeutic window that sets lower and upper bounds for the one or more parameters of the electrical stimulation therapy.

In another example, processor 310 receives, via telemetry module 308, a signal from sensors 109 indicative of a physiological parameter of the patient. In response to the physiological parameter, processor 310 of external programmer 104 issues instructions to IMD 106 to adjust one or both bounds of the homeostatic window. For example, in response to signals from sensors 109, processor 310 may determine that the magnitude of one or more parameters defining the electrical stimulation therapy is insufficient to reduce the one or more symptoms of patient 112. In this example, processor 310, via telemetry module 308, issues instructions to IMD 106 to shift downward the upper bound of the homeostatic window, or the entire homeostatic window itself. To drive the signal to a lower window, the IMD 106 effectively increases the one or more parameters of the electrical stimulation therapy, and thereby increases the magnitude of electrical stimulation therapy to reduce the symptoms of the patient. In another example, in response to signals from sensors 109, processor 310 may determine that, based on a symptom of the patient (e.g., tremor, rigidity, or wrist flexion), a posture of the patient (e.g., laying, sitting, standing, etc.) or an activity level of the patient (i.e., sleeping, walking, exercising, etc.), processor 310 should adjust the magnitude of one or more parameters defining the electrical stimulation therapy. Processor 310 may issue instructions, via telemetry module 308, to IMD 106 to adjust the lower bound of the homeostatic window, the upper bound of the homeostatic window, or the entire homeostatic window itself. By allowing the signal to float at different magnitudes, IMD 106 adjusts the one or more parameters of the electrical stimulation therapy, and thereby adjusts the magnitude of electrical stimulation therapy to compensate for different activity levels of patient 112. Typically, processor 310 may not resize the therapeutic window beyond safety guidelines set by the clinician, which may be expressed as a maximum adjustment to upper bound, lower bound, or window shift, either in an absolute sense or in the sense of a maximum adjustment per unit time.

Figure 4:
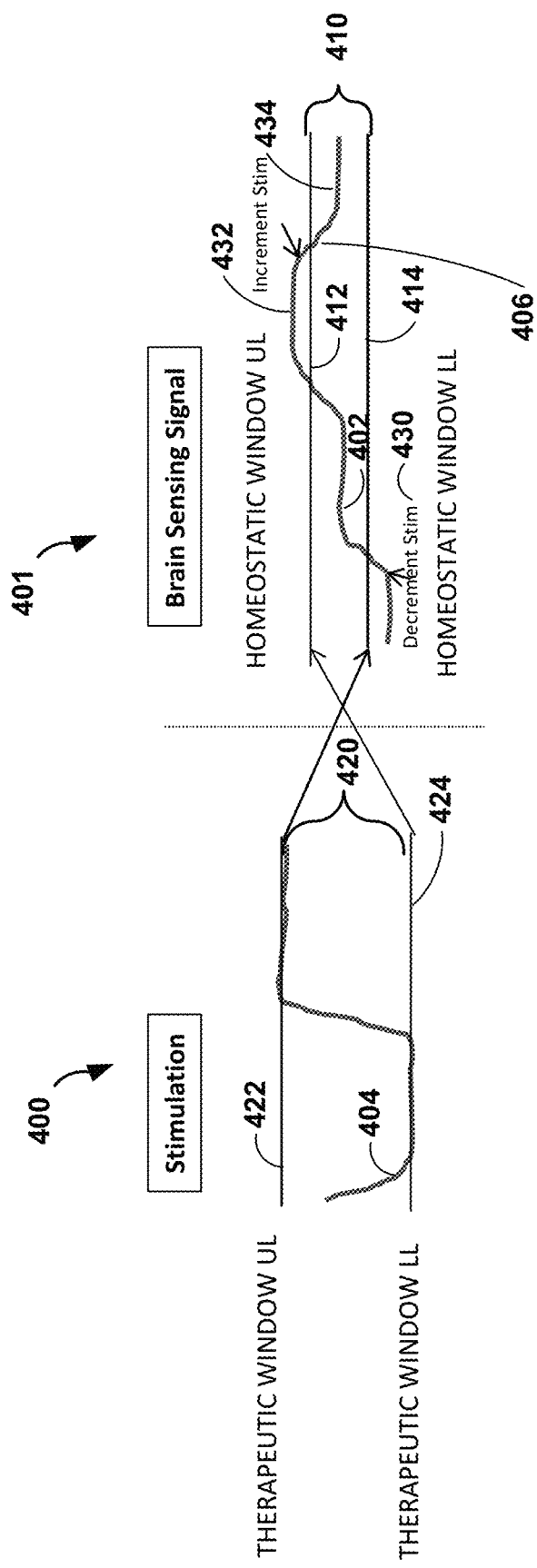
FIG. 4 is a timing diagram illustrating the example system of FIG. 1 setting a lower bound and an upper bound of a homeostatic window for a proportional signal with respect to a therapeutic window, in accordance with an example of the techniques of the disclosure.

FIG. 4 is a timing diagram illustrating the example system of FIG. 1 for setting a lower bound 414 and an upper bound 412 of the homeostatic window 410 for a proportional signal according to the techniques of the disclosure. In the example of FIG. 4, the horizontal axis depicts time and is identical for both graphs 400 and 401. The vertical axis of graph 400 depicts the magnitude of the one or more parameters of the electrical stimulation, while the vertical axis of graph 401 depicts the magnitude of the sensed neurological signal.

In the example of FIG. 4, IMD 106, via one or more electrodes, monitors a signal 402, e.g., a neurological signal within a Beta frequency band of brain 120 of patient 112, that is proportional to the severity of one or more symptoms of the patient. Further, IMD 106 delivers electrical stimulation therapy having a voltage magnitude 404 within an upper limit 422 and a lower limit 424 of therapeutic window 420. Graph 400 depicts a voltage amplitude of electrical stimulation delivered to patient 112 along the y-axis with respect to time along the x-axis. Graph 401 depicts a magnitude of a signal, such as a neurological signal within the Beta frequency band, of patient 112 along the y-axis with respect to time along the x-axis. Graph 400 depicts the electrical stimulation provided by IMD 106 in response to the measured signal of graph 401.

In the example of FIG. 4, a patient 112 has taken medication selected to reduce one or more symptoms. For Parkinson's disease, such medications may include extended release forms of dopamine agonists, regular forms of dopamine agonists, controlled release forms of carbidopa/ levodopa (CD/LD), regular forms of IMD, entacapone, rasagiline, selegiline, and amantadine.

To determine the lower bound 414 of homeostatic window 410, in one example, a clinician ensures that the patient has received one of medication selected to reduce one or more symptoms. Typically, the clinician ensures that the patient has been on the medication, i.e., has been taking regularly prescribed doses of the medication, for at least approximately 72 hours for extended release forms of dopamine agonists, the patient has been on medication for at least approximately 24 hours for regular forms of dopamine agonists and controlled release forms of CD/LD, and the patient has been on medication for at least approximately 12 hours for regular forms of CD/LD, entacapone, rasagiline, selegiline, and amantadine. In FIG. 4, the effectiveness of the medicine may be observed as, for example, a decrease 406 in a Beta signal of a brain of the patient. In other examples, instead of, or complimentary with the medication selected to reduce the one or more symptoms, the patient 112 receives a maximum magnitude of electrical stimulation therapy, as defined by the upper bound of the therapeutic window for patient safety and/or comfort, to reduce the one or more symptoms.

The clinician, via external programmer 104, instructs IMD 106 to titrate the voltage amplitude 404 of the electrical stimulation therapy delivered to patient 112. Typically, the clinician will begin at a value for the voltage amplitude 404 approximately in the middle of the therapeutic window and instruct IMD 106 to gradually decrease the magnitude of the voltage amplitude 404. However, in some examples, the clinician begins at a value for the voltage amplitude 404 approximately equal to the upper bound of the therapeutic window and gradually decreases the magnitude of the voltage amplitude. The clinician determines the point at which the magnitude of the voltage amplitude 404 is sufficient enough to reduce the one or more symptoms of patient 112, and any further reduction in the one or more parameters causes symptoms of the disease of patient 112 to emerge. In the example of Parkinson's disease, the clinician determines the point at which further reduction in the voltage amplitude 404 causes an increase in the severity of the symptoms of patient 112 under the UPDRS or MDS-UPDRS.

At this magnitude of the voltage amplitude 404, the clinician measures the magnitude of the signal 402 of the patient 112 and sets, via external programmer 104, this magnitude as the lower bound 414 of the homeostatic window 410. In some examples, the clinician may select a value for the lower bound 414 of the homeostatic window to be a predetermined amount, e.g., 5% or 10%, lower than the magnitude at which the symptoms of the patient 112 emerge to prevent emergence of the symptoms of the patient 112 during subsequent use.

In another example, the clinician sets the lower bound by first ensuring that the patient is off medication for the one or more symptoms. Typically, the clinician ensures that, prior to the time at which the lower bound is determined, the patient has been off the medication, i.e., has not taken the medication, for at least approximately 72 hours for extended release forms of dopamine agonists, the patient has been off medication for at least approximately 24 hours for regular forms of dopamine agonists and controlled release forms of CD/LD, and the patient has been off medication for at least approximately 12 hours for regular forms of CD/LD, entacapone, rasagiline, selegiline, and amantadine.

In this example, the clinician delivers electrical stimulation having a value for the voltage amplitude 404 approximately equal to the upper bound of the therapeutic window. In some examples, the clinician delivers electrical stimulation having a value for the voltage amplitude slightly below the magnitude which induces side effects in the patient 112. Typically, this causes maximal reduction of the one or more symptoms of the disease of the patient 112, and therefore maximal reduction of the signal. At this magnitude of the voltage amplitude 404, the clinician measures the magnitude of the signal 402 of the patient 112 and sets, via external programmer 104, this magnitude as the lower bound 414 of the homeostatic window 410. In some examples, the clinician may select a value for the lower bound 414 of the homeostatic window that is a predetermined amount, e.g., 5% or 10%, lower than the magnitude at which the symptoms of the patient 112 emerge to prevent emergence of the symptoms of the patient 112 during subsequent use.

To determine the upper bound 412 of homeostatic window 410, the clinician ensures that the patient has not received medication selected to reduce the one or more symptoms. Typically, to set the upper bound of the homeostatic window, the clinician ensures that the patient has been off medication, i.e., has not taken the medication, for at least approximately 72 hours for extended release forms of dopamine agonists, the patient has been off medication for at least approximately 24 hours for regular forms of dopamine agonists and controlled release forms of CD/LD, and the patient has been off medication for at least approximately 12 hours for regular forms of CD/LD, entacapone, rasagiline, selegiline, and amantadine.

The clinician, via external programmer 104, instructs IMD 106 to titrate the voltage amplitude 404 of the electrical stimulation therapy delivered to patient 112. Typically, the clinician will begin with a very low value for the voltage amplitude 404 and instruct IMD 106 to gradually increase the magnitude of the voltage amplitude 404. In one example, the clinician determines a minimum magnitude of the voltage amplitude 404 sufficient to reduce the one or more symptoms of patient 112. In another example, the clinician determines the point at which further increase to the magnitude of the voltage amplitude 404 defining the electrical stimulation therapy does not cause a further reduction in the severity of the symptoms of the disease of patient 112. For example, in the example of Parkinson's disease, the clinician may determine the point at which increasing the magnitude of the voltage amplitude 404 does not cause a further reduction in the score of patient 112 under the UPDRS or MDS-UPDRS. At this magnitude of the voltage amplitude 404 of the electrical stimulation therapy, the clinician measures the magnitude of the signal 402 of the patient 112 and sets, via external programmer 104 this magnitude as the upper bound 412 of the homeostatic window 410. In some examples, the clinician may select a value for the upper bound 412 of the homeostatic window that is a predetermined amount, e.g., 5% or 10%, higher than measured magnitude of the signal to prevent, during subsequent use, discomfort to patient 112 due to side effects of the therapy.

In the example of FIG. 4, during time 430, the sensed signal (e.g., the sensed neurological signal or physiological parameter of patient 112) is below the lower bound 414 of the homeostatic window. Accordingly, IMD 106 decrements the voltage amplitude of the electrical stimulation. Note that IMD 106 does not decrement stimulation below the lower bound 424 of the therapeutic window. Similarly, during time 432, the signal is above the upper bound 412 of the homeostatic window. Accordingly, IMD 106 increments the voltage amplitude of the electrical stimulation. Note that IMD 106 does not increment stim above the upper bound 422 of the therapeutic window. When the signal returns to within the homeostatic window at time 434, IMD maintains the present voltage amplitude of the electrical stimulation.

Figure 5:
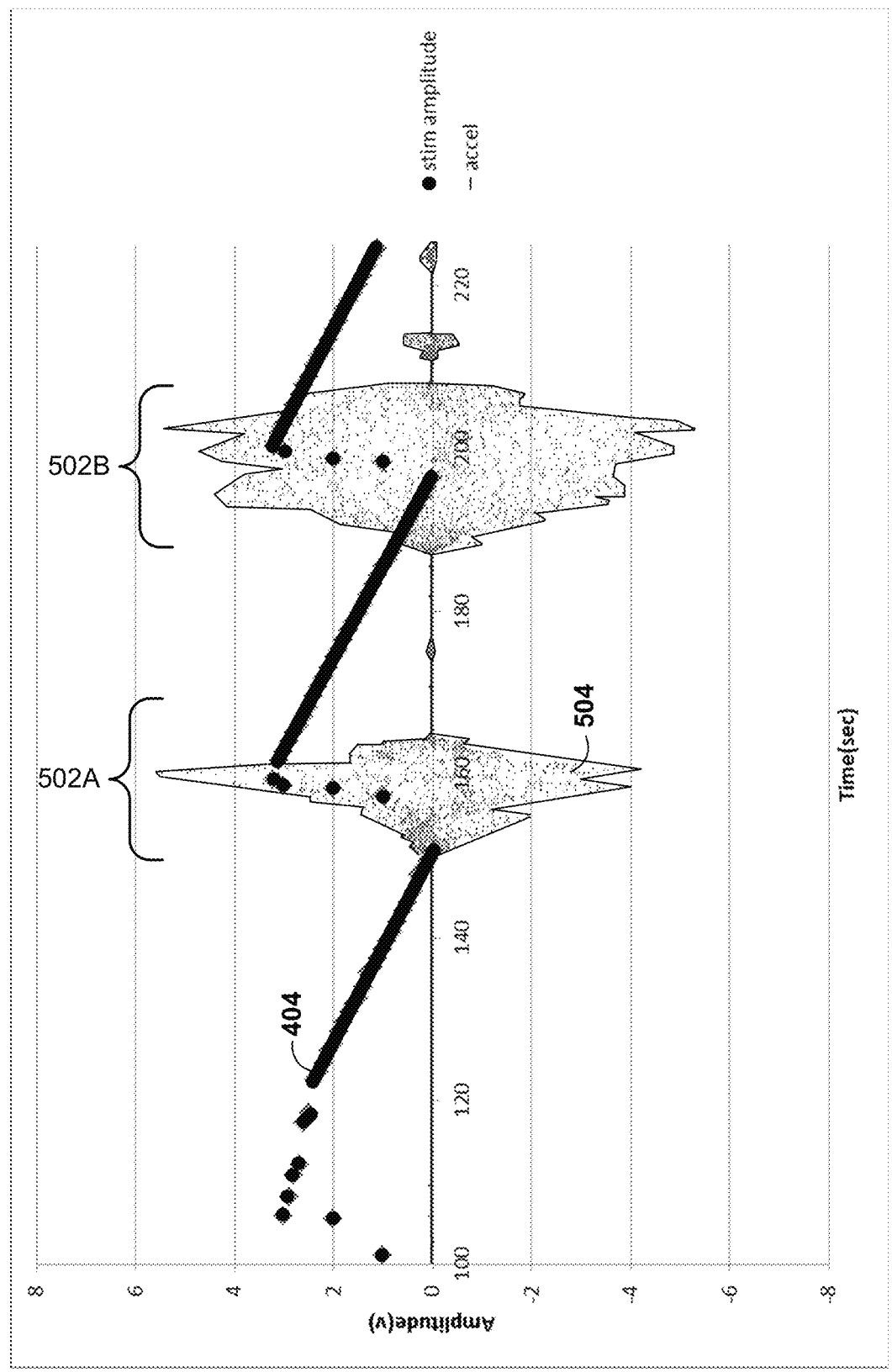
FIG. 5 is a graph illustrating an example operation for setting a lower bound of the homeostatic window according to an example of the techniques of the disclosure.

FIG. 5 is a graph illustrating an example operation for setting a lower bound of the homeostatic window according to the techniques of the disclosure. In the example of FIG. 5, IMD 106, via one or more electrodes, monitors a signal, e.g., a neurological signal within the Beta frequency band of brain 120 of patient 112, that is proportional to the severity of one or more symptoms of the patient. Further, IMD 106 delivers electrical stimulation therapy having a voltage magnitude 404 within an upper limit and a lower limit of a therapeutic window. Sensors 109 monitor a physiological parameter of patient 112. In the example of FIG. 5, sensors 109 are accelerometers that monitor a magnitude 504 of a tremor of patient 112. FIG. 5 depicts the output signal 504 of sensors 109 and the voltage magnitude 404 along the y-axis with respect to time in seconds along the x-axis.

To determine the lower bound 414 of homeostatic window 410, a clinician ensures that, the patient has received medication selected to reduce one or more symptoms. Typically, the clinician ensures that, prior to the time that the lower bound is defined, the patient has been on the medication, i.e., has been taking regularly prescribed doses of the medication, for at least approximately 72 hours for extended release forms of dopamine agonists, the patient has been on medication for at least approximately 24 hours for regular forms of dopamine agonists and controlled release forms of CD/LD, and the patient has been on medication for at least approximately 12 hours for regular forms of CD/LD, entacapone, rasagiline, selegiline, and amantadine.

The clinician, via external programmer 104, instructs IMD 106 to titrate the voltage amplitude 404 of the electrical stimulation therapy delivered to patient 112. Typically, the clinician will begin at a midrange value for the voltage amplitude 404 and instruct IMD 106 to gradually decrease the magnitude of the voltage amplitude 404. The clinician determines the point at which the magnitude of the voltage amplitude 404 is sufficient enough to reduce the one or more symptoms of patient 112, and any further reduction in the one or more parameters causes symptoms of the disease of patient 112 to emerge. In the example of FIG. 5, external processor ramps down voltage amplitude 404 of the electrical stimulation therapy until patient 112 experiences one or more "break-through" events 502A-502B of the tremor of patient 112, i.e., failure to reduce symptoms or return of symptoms.

At this magnitude of the voltage amplitude 404 that the "break-through" events 502A-502B occur, the clinician measures the magnitude of the signal of the patient 112 and sets, via external programmer 104, this magnitude as the lower bound 414 of the homeostatic window. In some examples, the clinician may select a value for the lower bound of the homeostatic window that is a predetermined amount, e.g., 5% or 10%, lower than the magnitude at which the symptoms of the patient 112 emerge to prevent additional "break-through" events from occurring during subsequent use. In addition, a clinician may use the magnitude of the voltage amplitude 404 found in this test to set the lower bound 424 of the therapeutic window. In other words, the clinician may set this magnitude as the minimum amplitude to which the system 100 may reduce the electrical stimulation voltage so as to prevent any symptom breakthrough.

Figure 6:
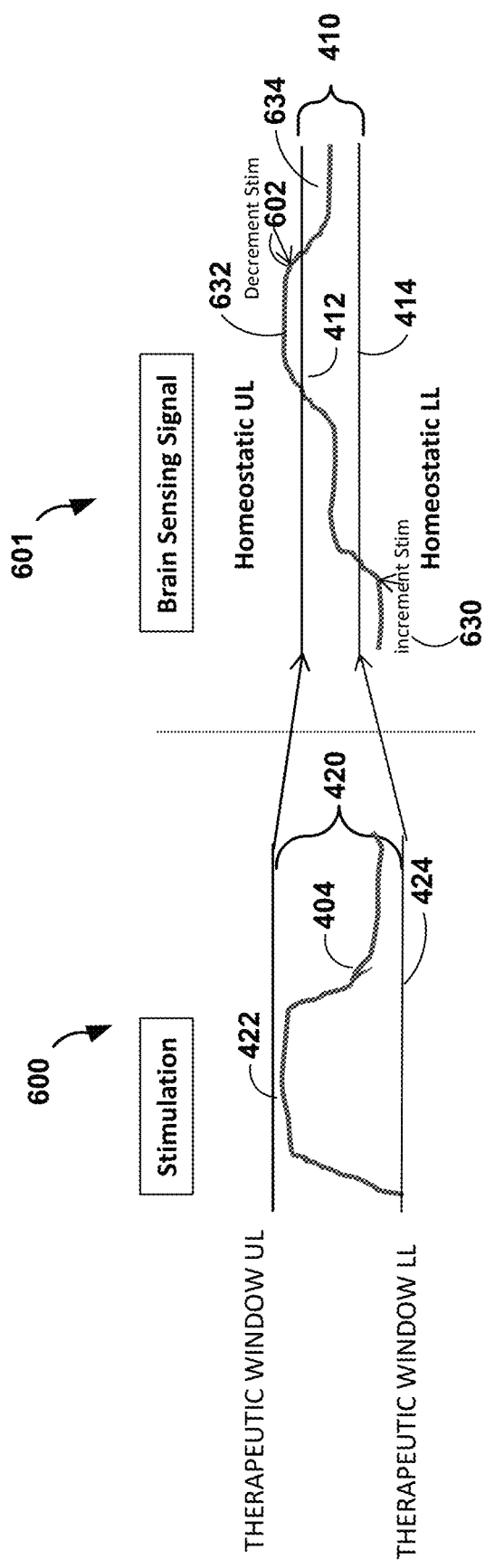
FIG. 6 is a timing diagram illustrating the example system of FIG. 1 setting a lower bound and an upper bound of the homeostatic window for an inversely proportional signal according to an example of the techniques of the disclosure.

FIG. 6 is a timing diagram illustrating the example system of FIG. 1 for setting a lower bound and an upper bound of the homeostatic window for an inversely proportional signal according to the techniques of the disclosure. In the example of FIG. 6, the horizontal axis depicts time and is identical for both graphs 600 and 601. The vertical axis of graph 600 depicts the magnitude of the one or more parameters of the electrical stimulation, while the vertical axis of graph 401 depicts the magnitude of the sensed neurological signal.

In the example of FIG. 6, IMD 106, via one or more electrodes, monitors a biological signal 602, e.g., a neurological signal within the Gamma frequency band of brain 120 of patient 112, that is inversely proportional to the severity of side effects due to electrical stimulation therapy. Further, IMD 106 delivers electrical stimulation therapy having a voltage magnitude 404 within an upper limit 422 and a lower limit 424 of therapeutic window 420. Graph 600 depicts a voltage amplitude of electrical stimulation delivered to patient 112 along the y-axis with respect to time along the x-axis. Graph 601 depicts a magnitude of a signal, such as a signal within the Gamma frequency band, of patient 112 along the y-axis with respect to time along the x-axis. Graph 600 depicts the electrical stimulation provided by IMD 106 in response to the measured signal of graph 601.

Note that in contrast to FIG. 4, FIG. 6 depicts a signal that is inversely proportional to the severity of side effects due to electrical stimulation therapy. In other words, as the magnitude of the severity of the side effects due to electrical stimulation therapy increases, the magnitude of the inversely proportional signal decreases. Accordingly, the upper and lower bounds for the inversely proportional signal are the opposite of the upper and lower bounds of the proportional signal of FIG. 4.

In the example of FIG. 6, a patient 112 has not taken medication selected to reduce one or more symptoms prior to the evaluation, as described above. For Parkinson's disease, such medications include extended release forms of dopamine agonists, regular forms of dopamine agonists, controlled release forms of carbidopa/levodopa (CD/LD), regular forms of CD/LD, entacapone, rasagiline, selegiline, and amantadine.

To determine the upper bound 412 of homeostatic window 410, a clinician ensures that the patient has received medication selected to reduce one or more symptoms. Typically, the clinician ensures that, prior to defining the upper bound, the patient has been on the medication, i.e., has been taking regularly prescribed doses of the medication, for at least approximately 72 hours for extended release forms of dopamine agonists, the patient has been on medication for at least approximately 24 hours for regular forms of dopamine agonists and controlled release forms of CD/LD, and the patient has been on medication for at least approximately 12 hours for regular forms of CD/LD, entacapone, rasagiline, selegiline, and amantadine. In FIG. 6, the effectiveness of the medicine may be observed as an increase 602 in the neurological signal within the Gamma frequency band.

The clinician, via external programmer 104, instructs MD 106 to titrate the voltage amplitude 404 of the electrical stimulation therapy delivered to patient 112. Typically, the clinician will begin at a midrange value for the voltage amplitude 404 and instruct IMD 106 to gradually decrease the magnitude of the voltage amplitude 404. The clinician determines the point at which the magnitude of the voltage amplitude 404 is sufficient enough to reduce the one or more symptoms of patient 112, and any further reduction in the one or more parameters causes symptoms of the disease of patient 112 to emerge. In the example of Parkinson's disease, the clinician determines the point at which further reduction in the voltage amplitude 404 causes an increase in the severity of the symptoms of patient 112 under the UPDRS or MDS-UPDRS.

At this magnitude of the voltage amplitude 404, the clinician measures the magnitude of the signal 402 of the patient 112 and sets, via external programmer 104, this magnitude of the signal as the upper bound 412 of the homeostatic window 410. In some examples, the clinician may select a value for the upper bound 412 of the homeostatic window that is a predetermined amount, e.g., 5% or 10%, lower than the magnitude at which the symptoms of the patient 112 emerge to prevent emergence of the symptoms of the patient 112 during subsequent use.

To determine the upper bound 412 of homeostatic window 410, the clinician ensures that the patient has received medication selected to reduce the one or more symptoms. Typically, when medication and electrical stimulation are combined, a Gamma signal is selected as the sensed signal for defining homeostatic window 410, as opposed a Beta signal. Thus, to set the upper bound of the homeostatic window for a system monitoring a signal within the Gamma frequency band of brain 120 of patient 112, typically the clinician ensures that, prior to defining the upper bound 412, the patient has been on medication, i.e., has been taking regularly prescribed doses of the medication, for at least approximately 72 hours for extended release forms of dopamine agonists, the patient has been on medication for at least approximately 24 hours for regular forms of dopamine agonists and controlled release forms of CD/LD, and the patient has been on medication for at least approximately 12 hours for regular forms of CD/LD, entacapone, rasagiline, selegiline, and amantadine.

The clinician, via external programmer 104, instructs IMD 106 to titrate the voltage amplitude 404 of the electrical stimulation therapy delivered to patient 112. Typically, the clinician will begin with a very low value for the voltage amplitude 404 and instruct IMD 106 to gradually increase the magnitude of the voltage amplitude 404. In one example, the clinician determines a minimum magnitude of the voltage amplitude 404 sufficient to reduce the one or more symptoms of patient 112. In another example, the clinician determines the point at which further increase to the magnitude of the voltage amplitude 404 of the defining the electrical stimulation therapy causes side effect symptoms of the disease of patient 112. For example, in the example of Parkinson's disease, the clinician may determine the point at which increasing the magnitude of the voltage amplitude 404 causes the side effect dyskinesia.

At this magnitude of the voltage amplitude 404 of the electrical stimulation therapy, the clinician measures the magnitude of the signal 602 of the patient 112 and sets, via external programmer 104, this magnitude as the upper bound 412 of the homeostatic window 410. In some examples, the clinician may select a value for the upper bound 412 of the homeostatic window that is a predetermined amount, e.g., 5% or 10%, lower than a measured magnitude of the signal to prevent, during subsequent use, discomfort to patient 112 due to side effects of the therapy.

In the example of FIG. 6, during time 630, the signal is below the lower bound 414 of the homeostatic window. Accordingly, IMD 106 increments the voltage amplitude of the electrical stimulation. Note that IMD 106 does not increment stim above the upper bound 422 of the therapeutic window. Similarly, during time 632, the signal is above the upper bound 412 of the homeostatic window. Accordingly, IMD 106 decrements the voltage amplitude of the electrical stimulation. Note that IMD 106 does not decrement stim below the lower bound 424 of the therapeutic window.

When the signal returns to within the homeostatic window at time 434, IMD maintains the present voltage amplitude of the electrical stimulation.

Figure 7:
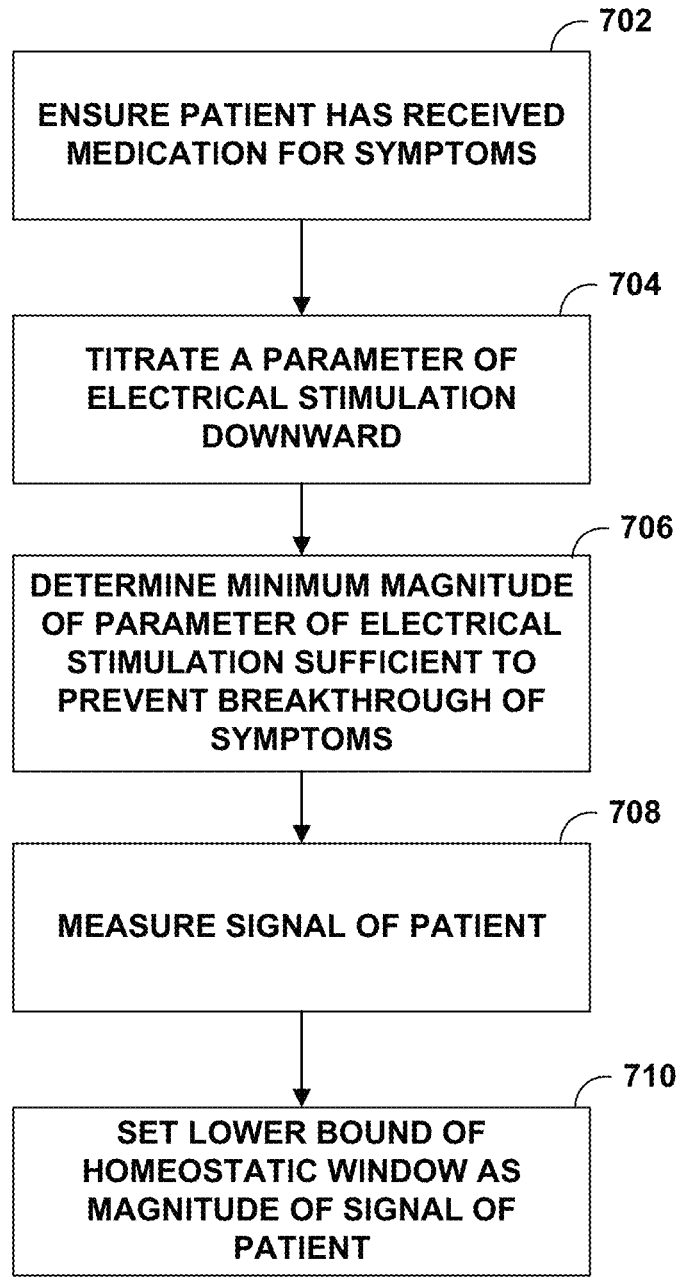
FIG. 7 is a flowchart illustrating an example operation for setting a lower bound of the homeostatic window for a proportional signal according to an example of the techniques of the disclosure.

FIG. 7 is a flowchart illustrating an example operation for setting a lower bound of the homeostatic window for a proportional signal, e.g., a neurological signal within the Beta frequency band, according to the techniques of the disclosure. For convenience, FIG. 7 is described with reference to system 100 of FIG. 1.

A clinician ensures that the patient has received medication selected to reduce one or more symptoms for at least time period prior to the evaluation as described above (702). Such medications include extended release forms of dopamine agonists, regular forms of dopamine agonists, controlled release forms of carbidopa/levodopa (CD/LD), regular forms of CD/LD, entacapone, rasagiline, selegiline, and amantadine. Typically, to set the lower bound of the homeostatic window, the clinician ensures that the patient has been on medication, i.e., has taken prescribed doses of the medication, for at least approximately 72 hours for extended release forms of dopamine agonists, the patient has been on medication for at least approximately 24 hours for regular forms of dopamine agonists and controlled release forms of CD/LD, and the patient has been on medication for at least approximately 12 hours for regular forms of CD/LD, entacapone, rasagiline, selegiline, and amantadine.

The clinician, via external programmer 104, instructs IMD 106 to titrate downward one or more parameters, such as a voltage or current amplitude, defining the electrical stimulation therapy delivered to patient 112 (704). Typically, the clinician begins with a value in the middle of the therapeutic window or near the upper bound of the therapeutic window for the one or more parameters and instructs IMD 106 to gradually decrease the magnitude of the one or more parameters. In one example, the clinician determines a minimum magnitude of the one or more parameters sufficient to prevent breakthrough of the one or more symptoms of patient 112 (706). For example, in the example of Parkinson's disease, the clinician determines the point at which the symptoms of Parkinson's disease in patient 112 emerge, as measured by sudden increase with respect to tremor or rigidity, in the score of patient 112 under the UPDRS or MDS-UPDRS. In another example, the clinician measures a wrist flexion of the patient and determines the point at which further decrease to the magnitude of one or more parameters defining the electrical stimulation therapy causes a sudden increase in the lack of wrist flexion of the patient.

At this magnitude of one or more parameters defining the electrical stimulation therapy, the clinician measures the magnitude of the signal of the patient 112. (e.g., a signal within the Beta frequency band) (708) and sets, via external programmer 104, this magnitude as the lower bound of the homeostatic window (710). In some examples, the signal is a neurological signal within the Beta frequency band of the patient. In some examples, the clinician may select a value for the lower bound of the homeostatic window that is a predetermined amount, e.g., 5% or 10%, higher than the measured magnitude of the signal to prevent breakthrough of the symptoms of patient 112.

However, in alternate examples, the clinician sets the lower bound by first ensuring that the patient is off medication for the one or more symptoms. In this example, the clinician delivers electrical stimulation having a value for the one or more parameters approximately equal to the upper bound of the therapeutic window. In some examples, the clinician delivers electrical stimulation having a value for the one or more parameters slightly below the magnitude which induces side effects in the patient 112. Typically, this causes maximal reduction of the one or more symptoms of the disease of the patient 112, and therefore maximal reduction of the signal. At this magnitude of the one or more parameters, the clinician measures the magnitude of the signal of the patient 112 and sets, via external programmer 104, this magnitude as the lower bound of the homeostatic window. In some examples, the clinician may select a value for the lower bound of the homeostatic window that is a predetermined amount, e.g., 5% or 10%, lower than the magnitude at which the symptoms of the patient 112 emerge to prevent emergence of the symptoms of the patient 112 during subsequent use.

Figure 8:
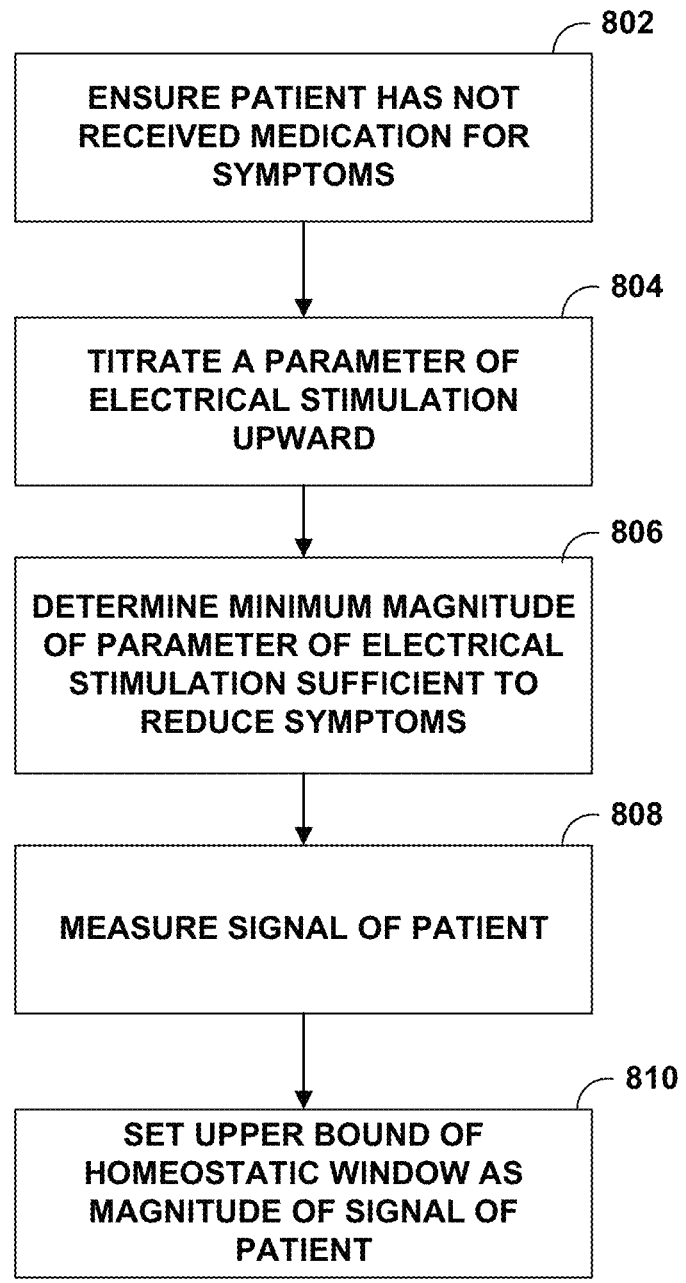
FIG. 8 is a flowchart illustrating an example operation for setting an upper bound of the homeostatic window for a proportional signal according to an example of the techniques of the disclosure.

FIG. 8 is a flowchart illustrating an example operation for setting an upper bound of the homeostatic window for a proportional signal according to the techniques of the disclosure. For convenience, FIG. 8 is described with reference to system 100 of FIG. 1. In some examples, the proportional signal is a neurological signal within the Beta frequency band of brain 120 of patient 112.

A clinician ensures that the patient has not received medication selected to reduce one or more symptoms (802). Such medications include extended release forms of dopamine agonists, regular forms of dopamine agonists, controlled release forms of carbidopa/levodopa (CD/LD), regular forms of CD/LD, entacapone, rasagiline, selegiline, and amantadine. Typically, to set the upper bound of the homeostatic window, the clinician ensures that, prior to setting the upper bound of the homeostatic window, the patient has not been on medication, i.e., has not taken the medication, for at least approximately 72 hours for extended release forms of dopamine agonists, the patient has not been on medication for at least approximately 24 hours for regular forms of dopamine agonists and controlled release forms of CD/LD, and the patient has not been on medication for at least approximately 12 hours for regular forms of CD/LD, entacapone, rasagiline, selegiline, and amantadine.

The clinician, via external programmer 104, instructs IMD 106 to titrate upward one or more parameters, such as a minimum voltage or current amplitude, defining the electrical stimulation therapy delivered to patient 112 (804). Typically, the clinician will begin at a midrange value for the one or more parameters and instruct IMD 106 to gradually increase the magnitude of the one or more parameters. The clinician determines the point at which the magnitude of the one or more parameters is sufficient enough to reduce the one or more symptoms of patient 112 (806). In some examples, the clinician determines the point at which any further increase in the one or more parameters does not cause a further reduction in the symptoms of the disease of patient 112. In the example of Parkinson's disease, the clinician determines the point at which further increase in the one or more parameters does not cause a further reduction in the severity of the symptoms of patient 112 under the UPDRS or MDS-UPDRS.

At this magnitude of one or more parameters defining the electrical stimulation therapy, the clinician measures the magnitude of the signal of the patient 112 (808) and sets, via external programmer 104, this magnitude as the upper bound of the homeostatic window (810). In some examples, the signal is a neurological signal within the Beta frequency band of the patient. In some examples, the clinician may select a value for the upper bound of the homeostatic window that is a predetermined amount, e.g., 5% or 10%, lower than the magnitude at which the symptoms of the patient 112 emerge to prevent emergence of the symptoms of the patient 112 during subsequent use.

Figure 9:
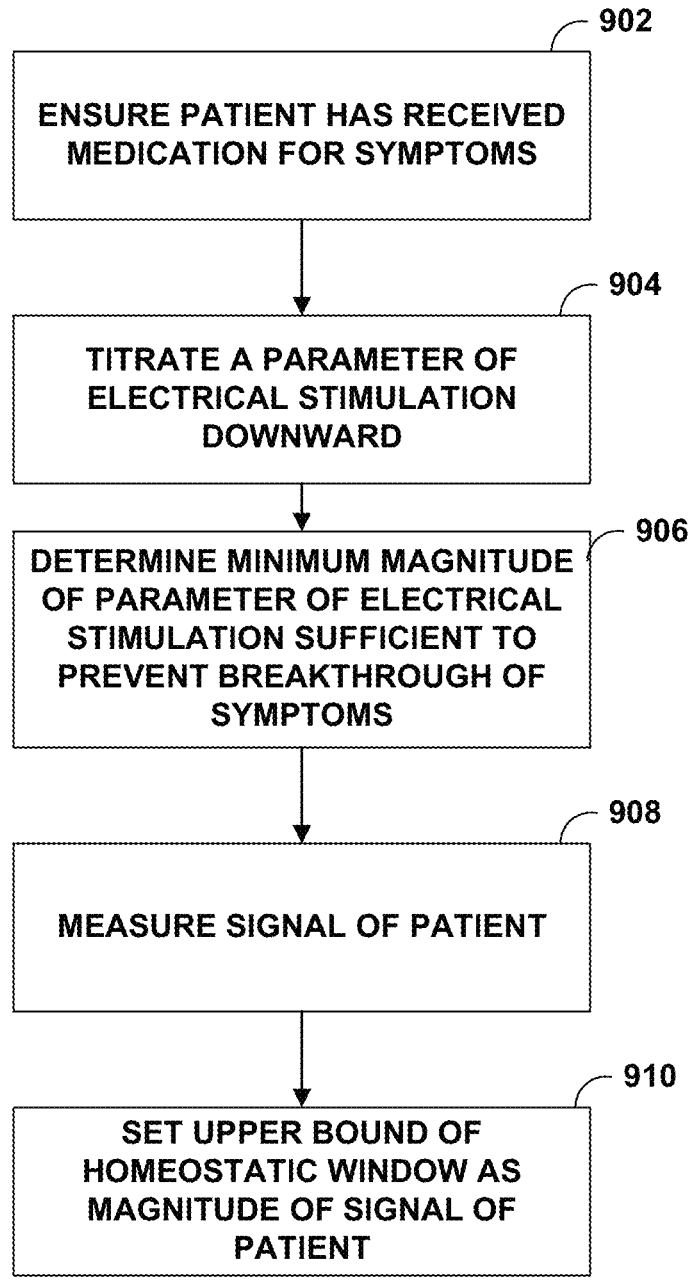
FIG. 9 is a flowchart illustrating an example operation for setting an upper bound of the homeostatic window for an inversely proportional signal according to an example of the techniques of the disclosure.

FIG. 9 is a flowchart illustrating an example operation for setting an upper bound of the homeostatic window for an inversely proportional signal, e.g., a signal within the Gamma frequency band, according to the techniques of the disclosure. For convenience, FIG. 9 is described with reference to system 100 of FIG. 1.

A clinician ensures that the patient has received medication selected to reduce one or more symptoms (902). Such medications include extended release forms of dopamine agonists, regular forms of dopamine agonists, controlled release forms of carbidopa/levodopa (CD/LD), regular forms of CD/LD, entacapone, rasagiline, selegiline, and amantadine. Typically, to set the upper bound of the homeostatic window, the clinician ensures that, prior to setting the upper bound of the homeostatic window, the patient has been on medication, i.e., has been taking regularly prescribed doses of the medication, for at least approximately 72 hours for extended release forms of dopamine agonists, the patient has been on medication for at least approximately 24 hours for regular forms of dopamine agonists and controlled release forms of CD/LD, and the patient has been off medication for at least approximately 12 hours for regular forms of CD/LD, entacapone, rasagiline, selegiline, and amantadine.

The clinician, via external programmer 104, instructs IMD 106 to titrate downward one or more parameters, such as a voltage or current amplitude, defining the electrical stimulation therapy delivered to patient 112 (904). Typically, the clinician begins with a value in the middle of the therapeutic window or near the upper bound of the therapeutic window for the one or more parameters and instructs IMD 106 to gradually decrease the magnitude of the one or more parameters. In one example, the clinician determines a minimum magnitude of the one or more parameters sufficient to prevent breakthrough of the one or more symptoms of patient 112 (906). For example, in the example of Parkinson's disease, the clinician determines the point at which the symptoms of Parkinson's disease in patient 112 emerge, as measured by sudden increase with respect to tremor or rigidity, in the score of patient 112 under the UPDRS or MDS-UPDRS. In another example, the clinician measures a wrist flexion of the patient and determines the point at which further decrease to the magnitude of one or more parameters defining the electrical stimulation therapy causes a sudden increase in the lack of wrist flexion of the patient.

At this magnitude of one or more parameters defining the electrical stimulation therapy, the clinician measures the magnitude of the signal of the patient 112 (908) and sets, via external programmer 104, this magnitude as the upper bound of the homeostatic window (910). In some examples, the signal is a neurological signal within the Gamma frequency band of the patient. In some examples, the clinician may select a value for the upper bound of the homeostatic window that is a predetermined amount, e.g., 5% or 10%, lower than measured magnitude of the signal to prevent, during subsequent use, discomfort to patient 112 due to side effects of the therapy.

However, in alternate examples, the clinician sets the upper bound by first ensuring that the patient is off medication for the one or more symptoms. In this example, the clinician delivers electrical stimulation having a value for the one or more parameters approximately equal to the upper bound of the therapeutic window. In some examples, the clinician delivers electrical stimulation having a value for the one or more parameters slightly below the magnitude which induces side effects in the patient 112. Typically, this causes maximal reduction of the one or more symptoms of the disease of the patient 112, and therefore maximal reduction of the signal. At this magnitude of the one or more parameters, the clinician measures the magnitude of the signal of the patient 112 and sets, via external programmer 104, this magnitude as the upper bound of the homeostatic window. In some examples, the clinician may select a value for the upper bound of the homeostatic window that is a predetermined amount, e.g., 5% or 10%, lower than the magnitude at which the symptoms of the patient 112 emerge to prevent emergence of the symptoms of the patient 112 during subsequent use.

Figure 10:
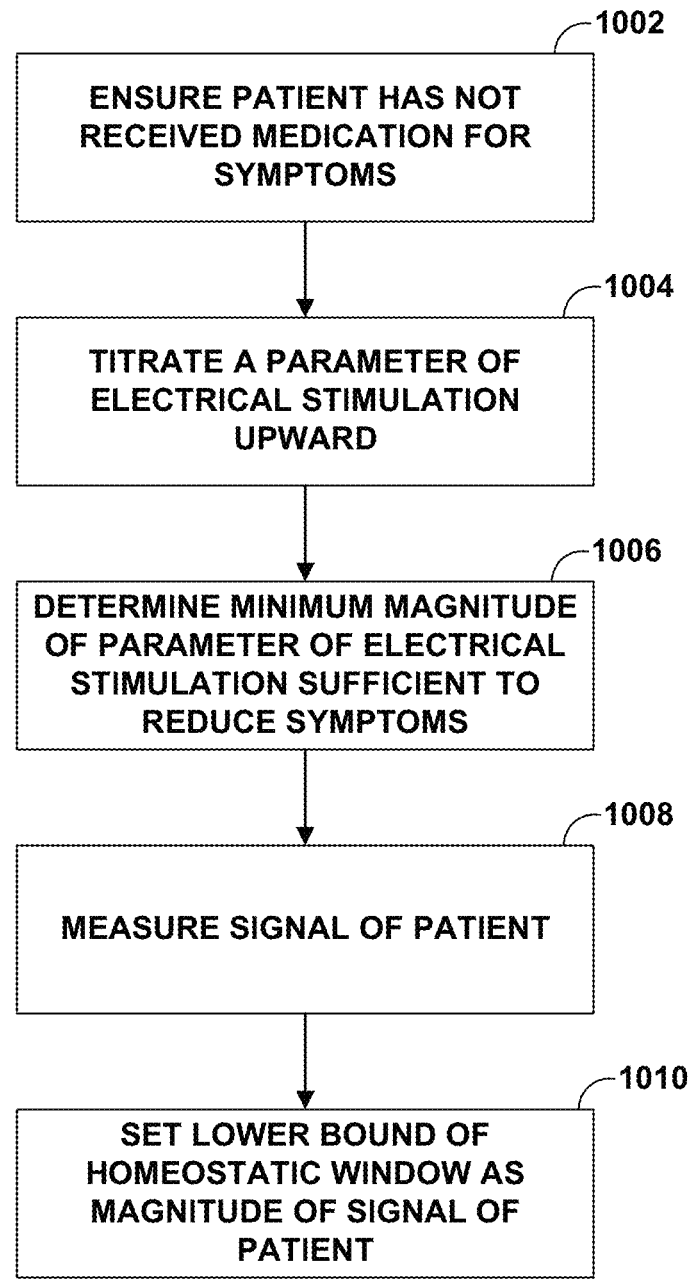
FIG. 10 is a flowchart illustrating an example operation for setting a lower bound of the homeostatic window for an inversely proportional signal according to an example of the techniques of the disclosure.

FIG. 10 is a flowchart illustrating an example operation for setting a lower bound of the homeostatic window for an inversely proportional signal according to the techniques of the disclosure. For convenience, FIG. 10 is described with reference to system 100 of FIG. 1.

A clinician ensures that the patient has not received medication selected to reduce one or more symptoms prior to the evaluation (1002). Such medications include extended release forms of dopamine agonists, regular forms of dopamine agonists, controlled release forms of carbidopa/levodopa (CD/LD), regular forms of CD/ID, entacapone, rasagiline, selegiline, and amantadine. Typically, to set the lower bound of the homeostatic window, the clinician ensures that the patient has been on medication, i.e., has been taking regularly prescribed doses of the medication, for at leak approximately 72 hours for extended release forms of dopamine agonists, the patient has been on medication for at least approximately 24 hours for regular forms of dopamine agonists and controlled release forms of CD/LD, and the patient has been on medication for at least approximately 12 hours for regular forms of CD/LD, entacapone, rasagiline, selegiline, and amantadine.

The clinician, via external programmer 104, instructs IMD 106 to titrate upward one or more parameters, such as a minimum voltage or current amplitude, defining the electrical stimulation therapy delivered to patient 112 (1004). Typically, the clinician will begin at a midrange value for the one or more parameters and instruct IMD 106 to gradually increase the magnitude of the one or more parameters. The clinician determines the point at Which the magnitude of the one or more parameters is sufficient enough to reduce the one or more symptoms of patient 112 (1006). In some examples, the clinician determines the point at which any further increase in the one or more parameters does not cause a further reduction in the symptoms of the disease of patient 112. In the example of Parkinson's disease, the clinician determines the point at which further increase in the one or more parameters does not cause a further reduction in the severity of the symptoms of patient 112 under the UPDRS or MDS-UPDRS.

At this magnitude of one or more parameters defining the electrical stimulation therapy, the clinician measures the magnitude of the signal of the patient 112 (1008) and sets, via external programmer 104, this magnitude as the lower bound of the homeostatic window (810). In some examples, the signal is a neurological signal within the Gamma frequency band of the patient. In some examples, the clinician may select a value for the lower bound of the homeostatic window that is a predetermined amount, e.g., 5% or 10%, lower than the magnitude at which the symptoms of the patient 112 emerge to prevent emergence of the symptoms of the patient 112 during subsequent use.

Figure 11:
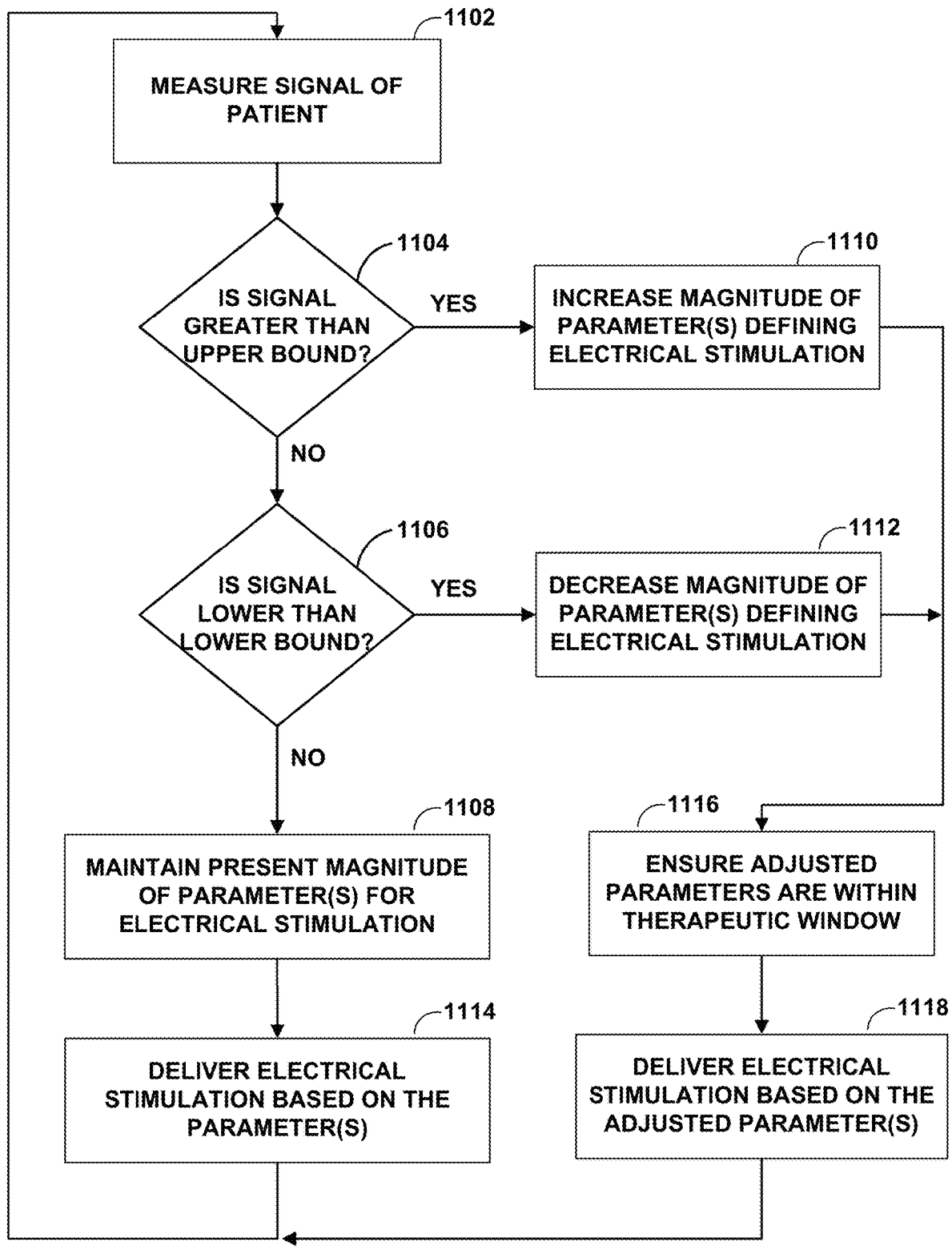
FIG. 11 is a flowchart illustrating an example operation for delivering adaptive deep brain stimulation (DBS) based on the deviation of a signal from the homeostatic window according to an example of the techniques of the disclosure.

FIG. 11 is a flowchart illustrating an example operation for delivering adaptive DBS based on the deviation of a signal from the homeostatic window according to the techniques of the disclosure. For convenience, FIG. 11 is described with respect to FIG. 1 and further with respect to a proportional signal, such as a neurological signal within the Beta frequency band of brain 120 of patient 112.

System 100 may adaptively deliver electrical stimulation and adjust one or more parameters defining the electrical stimulation within a parameter range defined by the lower and upper bounds of the therapeutic window based on the activity of the sensed signal within the homeostatic window. For example, IMD 106, via electrodes 116, 118, senses a signal of the brain 120 of patient 112 (1102). In some examples, this signal is a neurological signal within the Beta frequency band of the brain 120 or another proportional signal.

IMD 106 determines whether the sensed signal of patient 112 is greater than an upper bound of the homeostatic window (1104). Upon determining that the signal of patient 112 is greater than an upper bound of the homeostatic window, IMD 106 increases the magnitude of one or more parameters defining the electrical stimulation (1110). Note that if the sensed signal were instead an inversely proportional signal such as a neurological signal within the Gamma frequency band, the electrical stimulation magnitude would instead be decreased. Typically, IMD 106 increases the magnitude of one or more parameters such that the electrical stimulation is increased at a maximum ramp rate defined by the clinician.

If IMD 106 determines that the sensed signal of patient 112 is not greater than the upper bound of the homeostatic window, IMD 106 determines whether the sensed signal of patient 112 is less than a lower bound of the homeostatic window (1106). Upon determining that the signal of patient 112 is less than a lower bound of the homeostatic window, IMD 106 decreases the magnitude of one or more parameters defining the electrical stimulation (1112). Typically, IMD 106 decreases the magnitude of one or more parameters such that the electrical stimulation is decreased at a maximum ramp rate defined by the clinician.

Note that, as described above, the signal is proportional to the severity of the one or more symptoms of the patient (for example, as is the case when monitoring neurological signals within the Beta frequency band of the brain of patient 112). Thus, for a proportional signal such as beta, IMD 106 increases the magnitude of one or more parameters of the electrical stimulation when the signal is greater than the upper bound and decreases the magnitude of one or more parameters of the electrical stimulation when the signal is less than the lower bound. However, where the signal is inversely proportional to the severity of the one or more symptoms of the patient (for example, as is the case when monitoring a neurological signal within the Gamma frequency hand of the brain of patient 112), IMD 106 operates in an opposite manner. Accordingly, for an inversely proportional signal such as gamma, IMD 106 increases the magnitude of one or more parameters of the electrical stimulation when the signal is less than the lower bound and decreases the magnitude of one or more parameters of the electrical stimulation when the signal is greater than the upper bound.

As described above, the maximum ramp rate is typically determined based on a factor of the tolerance of the patient and the capabilities of system 100. In some examples, the maximum ramp rate is at least approximately 0.1 Volts per 400 milliseconds. In some examples, the clinician titrates a plurality of ramps, such as 0.1 Volts per 400 milliseconds; 0.5 Volts per 400 milliseconds; 1 Volt per 400 milliseconds;

and 2 Volts per 400 milliseconds, and selects a maximum ramp rate based on the tolerance of the patient and the reliability of the system 100. Typically, IMD 106 incrementally adjusts the magnitude of the one or more parameters. For example, IMD 106 may incrementally increase or decrease the magnitude of the one or more parameters by a partial amount such that, by repeating the operation of FIG. 8 at a particular frequency, IMD 106 effectively adjusts the magnitude of the one or more parameters at the maximum ramp rate. For example, where the maximum ramp rate is 0.1 Volts per 400 milliseconds and IMD 106 repeats the operation of FIG. 11 every 100 milliseconds, IMD 106 adjusts a voltage amplitude by 0.025 Volts. Thus, IMD 106 performs four 0.025 Volt adjustments over 400 milliseconds, effectively ramping the voltage amplitude by 0.1 Volts over 400 milliseconds, e.g., the maximum ramp rate.

Prior to delivering the electrical stimulation according to the one or more adjusted parameters, one of MD 106 and external programmer 104 ensures that the one or more adjusted parameters are greater than the lower bound of the therapeutic window and less than the upper bound of the therapeutic window (1116). If the one or more adjusted parameters are less than the lower bound of the therapeutic window, one of IMD 106 and external programmer 104 may reset the lower bound of the therapeutic window to be equal to the value of the one or more adjusted parameters. This may require user (e.g., clinician) input to allow this to occur. Alternatively, the adjusted parameter may be readjusted upward to the lower bound of the therapeutic window. If the one or more adjusted parameters are greater than the upper bound of the therapeutic window, one of IMD 106 and external programmer 104 may reset the upper bound of the therapeutic window to be equal to the value of the one or more adjusted parameters. Again, this may require some type of input, such as input from a clinician programmer providing approval from a clinician to overrule the bound of the therapeutic window. Alternatively, the adjusted parameter may be readjusted downward to the upper bound of the therapeutic window. In either case, the adjusted parameter is within the therapeutic window or an adjusted therapeutic window. Upon determining that the one or more adjusted parameters are within the therapeutic window, IMD 106 delivers electrical stimulation according to the one or more adjusted parameters (1118). After delivering the electrical stimulation, IMD 106 repeats the entire operation process and again senses a signal of patient 112 (1102).

Upon determining that the sensed signal of patient 112 is not greater than the upper bound of the homeostatic window and the sensed signal is not less than a lower bound of the homeostatic window, IMD 106 maintains the present magnitude of the one or more parameters (1108) and delivers electrical stimulation according to the one or more adjusted parameters (1114). Thus, while the signal is within the upper and lower bounds of the homeostatic window, IMD 106 continues to deliver electrical stimulation at the present magnitude of the one or more parameters. Further, if the signal deviates outside of the homeostatic window, upon detecting that the signal has returned to the homeostatic window, IMD 106 continues to deliver electrical stimulation at the previous magnitude of the one or more parameters. After delivering the electrical stimulation, IMD 106 repeats the entire operation process and again senses a signal of the brain 120 of patient 112 (1102).

Figure 12:
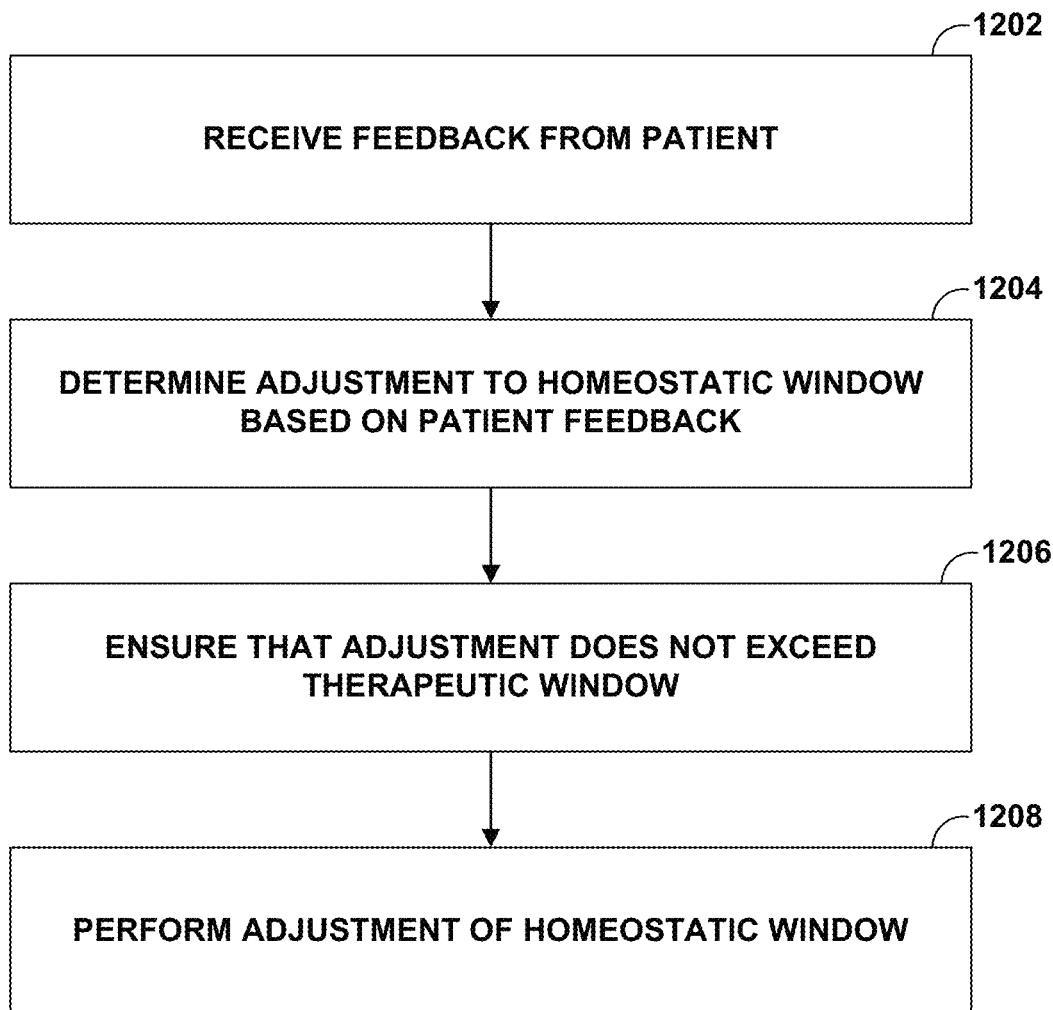
FIG. 12 is a flowchart illustrating an example operation for adjusting the homeostatic window in response to patient feedback according to an example of the techniques of the disclosure.

FIG. 12 is a flowchart illustrating an example operation for adjusting the homeostatic window in response to patient feedback according to the techniques of the disclosure. For convenience, FIG. 12 is described with respect to FIG. 1.

In the example of FIG. 12, external programmer 104 receives feedback from patient 112 regarding the efficacy of electrical stimulation delivered by IMD 106 (1202). For example, external programmer 104 may receive feedback from patient 112 that the electrical stimulation delivered by IMD 106 is insufficient to control one or more symptoms of patient 112, or that the electrical stimulation delivered by IMD 106 is causing side effects, paresthesia, or discomfort to patient 112.

In response to the feedback received from patient 112, external programmer 104 determines an adjustment to the homeostatic window (1204). For example, if external programmer 104 receives feedback from patient 112 that the electrical stimulation therapy is not treating the one or more symptoms of patient 112 effectively, external programmer 104 may determine a downward adjustment of the upper bound of the homeostatic window, or the entire homeostatic window itself. To drive a proportional signal (e.g., a neurological signal within the Beta frequency band) to a lower magnitude, the system increases the one or more parameters of the electrical stimulation therapy, and thereby increases the magnitude of electrical stimulation therapy to reduce the symptoms of the patient. Alternatively, to drive an inversely proportional signal (e.g., a neurological signal within the Gamma frequency band) to a lower magnitude, the system decreases the one or more parameters of the electrical stimulation.

Similarly, if external programmer 104 receives feedback from patient 112 that the electrical stimulation therapy is unpleasant, causes side effects, or is otherwise uncomfortable to patient 112, and if the signal is a proportional signal (e.g., a neurological signal within the Beta frequency band), external programmer 104 may determine an upward adjustment of the lower bound of the homeostatic window, or the entire homeostatic window itself. This has the effect of allowing the neurological signal to float to a higher window, effectively causing the system to decrease the one or more parameters of the electrical stimulation therapy, and thereby decreases the magnitude of electrical stimulation therapy to reduce side effects.

While the patient 112 may adjust one or more bounds of the homeostatic window, or the homeostatic window itself, typically, to ensure the safety of the patient, the patient 112 may not alter the therapeutic window that sets lower and upper bounds for the one or more parameters of the electrical stimulation therapy. Thus, prior to performing the adjustment of the homeostatic window, external programmer 104 determines whether the adjustment to the homeostatic window would result in a stimulation parameter value that exceeds an upper bound of the therapeutic window or is less than a lower bound of the therapeutic window (1206). Upon determining that the adjusted bounds of the homeostatic window result in stimulation parameter values that are within the therapeutic window, external programmer performs the adjustment to the homeostatic window (1208).

Figure 13:
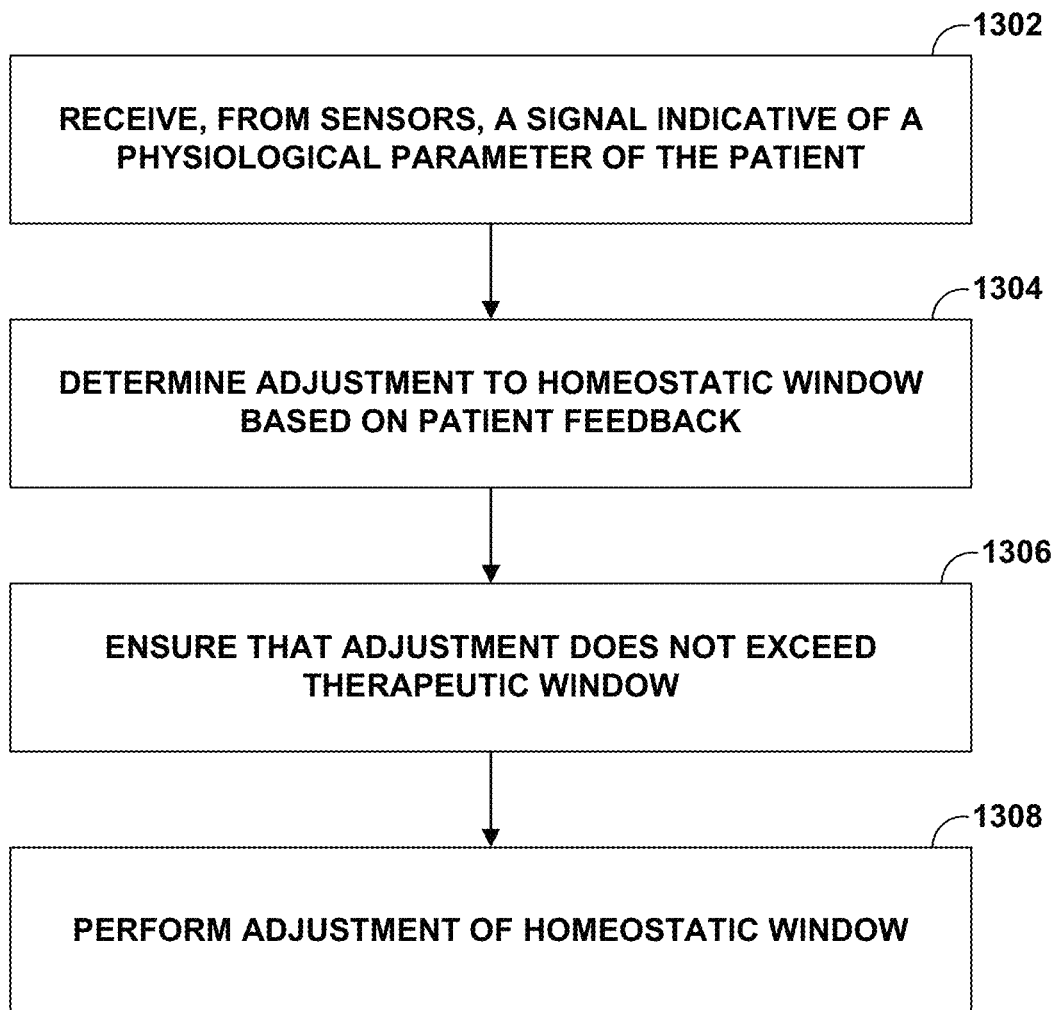
FIG. 13 is a flowchart illustrating an example operation for adjusting the homeostatic window in response to a signal indicative of a physiological parameter of the patient according to an example of the techniques of the disclosure.

FIG. 13 is a flowchart illustrating an example operation for adjusting the homeostatic window in response to a signal indicative of a physiological parameter of the patient according to the techniques of the disclosure. For convenience, FIG. 13 is described with respect to FIG. 1.

In the example of FIG. 13, external programmer 104 receives a signal from sensors 109, wherein the signal is indicative of a physiological parameter of the patient (1302). For example, in response to signals from sensors 109, external programmer 104 may determine that the magnitude of one or more parameters defining the electrical stimulation therapy is insufficient to reduce the one or more symptoms of patient 112. In another example, in response to signals from sensors 109, external programmer 104 may determine that, based on a symptom of the patient (e.g., tremor, rigidity, or wrist flexion), a posture of the patient (e.g., laying, sitting, standing, etc.) or an activity level of the patient (i.e., sleeping, walking, exercising, etc.), external programmer 104 should adjust the magnitude of one or more parameters defining the electrical stimulation therapy.

In response to the signal received from sensors 109, external programmer 104 determines an adjustment to the homeostatic window (1304). For example, external programmer 104 may determine an adjustment of the upper bound, the lower bound, or the entire homeostatic window itself. In one example, external programmer 104 makes an adjustment to effectively increase magnitude of the electrical stimulation therapy delivered to patient 112 to further reduce the one or more symptoms of the patient. In another example, external programmer an adjustment to effectively decrease magnitude of the electrical stimulation therapy delivered to patient 112 to reduce one or more side effects of the electrical stimulation therapy delivered to patient 112.

Accordingly, in response to the signal received from sensors 109, external programmer 106 may shift the upper bound of the homeostatic window downward to decrease the magnitude of the signal required to trigger IMD 106 to ramp up the magnitude of the one or more parameters defining the electrical stimulation to bring the signal back into the homeostatic window. External programmer 106 may shift the upper bound to cause IMD 106 to respond more quickly to changes in the sensed neurological signal that may indicate that a larger magnitude of one or more parameters of the electrical stimulation is required to reduce the one or more symptoms of patient 112. External programmer may adjust the upper bound of the homeostatic window in the opposite direction to have the opposite effect. Similarly, external programmer 106 may shift the lower bound of the homeostatic window upward to increase the magnitude of the sensed neurological signal required to trigger IMD 106 to ramp down the magnitude of the one or more parameters defining the electrical stimulation to bring the signal back into the homeostatic window. External programmer 106 may shift the lower bound to cause IMD 106 to respond more quickly to decreases in the sensed neurological signal that may indicate that a smaller magnitude of one or more parameters of the electrical stimulation is required to avoid inducing side effects in patient 112. External programmer may adjust the upper bound of the homeostatic window in the opposite direction to have the opposite effect. External programmer may adjust the lower bound of the homeostatic window in the opposite direction to have the opposite effect.

In yet a further example, external programmer 106 may adjust the position of the entire homeostatic window to adjust both the magnitude of the sensed neurological signal required to trigger IMD 106 to ramp up the magnitude of the one or more parameters defining the electrical stimulation and the magnitude of the sensed neurological signal required to trigger IMD 106 to ramp down the magnitude of the one or more parameters defining the electrical stimulation, so as to bring the signal back into the homeostatic window. Thus, external programmer 106 may adjust the shape and position of the homeostatic window so as to deliver adaptive DBS that is tailored to the needs of each individual patient.

Typically, system 100 may not resize the therapeutic window beyond safety guidelines set by the clinician, which may be expressed as a maximum adjustment to upper bound, lower bound, or window shift, either in an absolute sense or in the sense of a maximum adjustment per unit time. Thus, prior to performing the adjustment of the homeostatic window, external programmer 104 determines whether the adjustment to the homeostatic window would result in a stimulation parameter that exceeds an upper bound of the therapeutic window or is less than a lower bound of the therapeutic window (1306). Upon determining that the adjusted bounds of the homeostatic window result in stimulation parameter values that are within the therapeutic window, external programmer performs the adjustment to the homeostatic window (1308).

Figure 14:
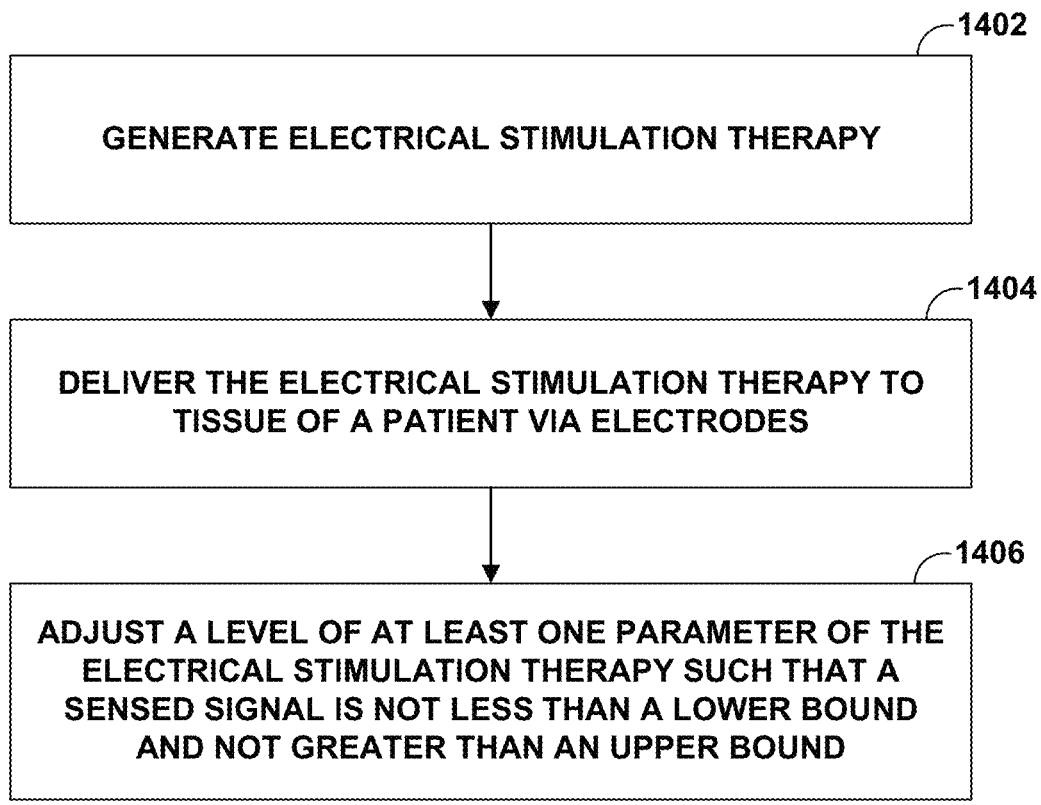
FIG. 14 is a flowchart illustrating an example operation for delivering adaptive deep brain stimulation according to an example of the techniques of the disclosure.

FIG. 14 is a flowchart illustrating an example operation for delivering adaptive deep brain stimulation according to the techniques of the disclosure. For convenience, FIG. 14 is described with respect to IMD 106 of FIG. 2.

In one example, stimulation generator 202 of IMD 106 generates electrical stimulation therapy (1402). Processor 210 of IMD 106, delivers the electrical stimulation therapy to tissue of a patient 112 via electrodes 116, 118 (1404). During delivery of the electrical stimulation therapy, processor 210, via electrodes 116, 118, senses a signal of the patient 112. In some examples, this signal is a signal of patient 112, such as a neurological signal within the Beta frequency band or Gamma frequency band of the brain 120 of patient 112. In other examples, this signal is a physiological parameter signal from one or more sensors, such as one or more accelerometers, gyros, or magnetometers. In this example, the signal may indicate a physiological parameter of the patient 112, such as a magnitude of rigidity of the patient due to Parkinson's disease, a magnitude of tremor of the patient due to Parkinson's disease, a magnitude of wrist flexion of the patient, a posture of the patient, a physical activity level of the patient, or a sleep state of the patient.

In response to the signal, processor 210 adjusts a magnitude of at least one parameter of the electrical stimulation therapy such that a sensed signal of the patient is not less than a lower bound of a homeostatic window and not greater than an upper bound of a homeostatic window (1406). In some examples, the sensed signal is a neurological signal within the Beta frequency band or Gamma frequency band of a brain 120 of patient 112. For example, while a patient is not taking medication selected to reduce one or more symptoms, a clinician determines a minimum magnitude of one or more parameters defining the electrical stimulation therapy, such as a minimum voltage or current amplitude, sufficient to reduce the one or more symptoms. The clinician defines the upper bound of the homeostatic window as a magnitude of the signal of the patient at this magnitude of electrical stimulation. Further, the clinician may determine a minimum magnitude of one or more parameters defining the electrical stimulation therapy, such as a minimum voltage or current amplitude, sufficient to reduce or maintain reduction of one or more symptoms when the patient is taking medication selected to reduce the symptoms. The clinician defines a lower bound of the homeostatic window as the signal of the patient at this magnitude of stimulation.

Figure 15:
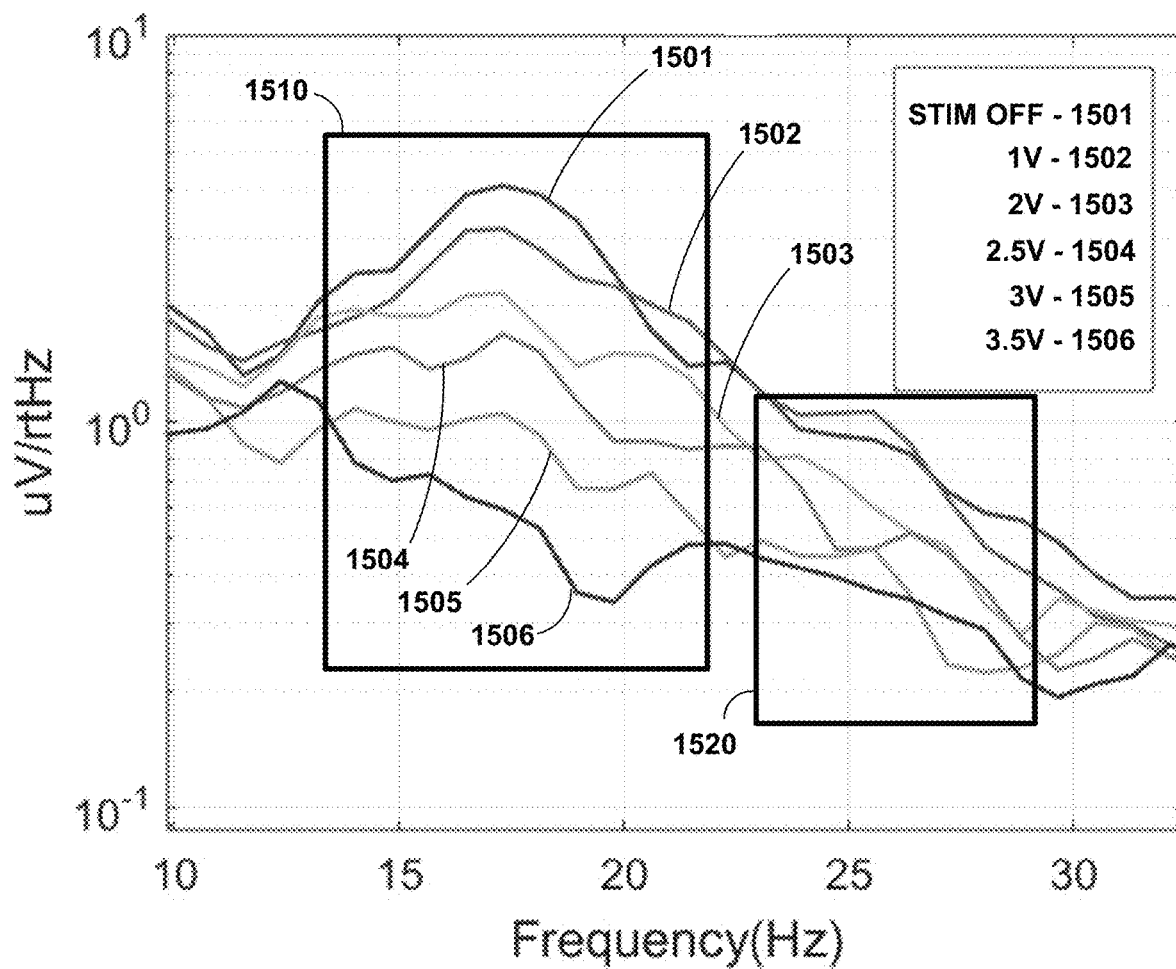
FIG. 15 is a graph illustrating an example response of a signal of a brain of the patient to electrical stimulation in accordance with an example of the techniques of the disclosure.

FIG. 15 is a graph illustrating an example response of a signal of a brain of the patient to electrical stimulation in accordance with the techniques of the disclosure. For convenience, FIG. 15 is described with respect to FIG. 1. In the example of FIG. 15, the horizontal axis depicts frequency in Hertz, while the vertical axis depicts a magnitude (e.g., spectral noise density) of a sensed neurological signal as measured in microvolts per root-Hertz. In the example of FIG. 15, the electrical stimulation further comprises a frequency of 140 Hertz and a pulse width of 90 microseconds.

In some examples, neurological signals of brain 120 of patient 112 may demonstrate multiple peak magnitudes within a frequency band of sensed neurological signals. Each of these peak magnitudes may be located within a different sub-band of the frequency band. Further, each of these sub-bands may respond differently to the electrical stimulation. In examples of system 100 where electrical stimulation is delivered based on sensing or tracking a neurological signal of brain 120 of patient 112, the correlation of the neurological signal to the severity of symptoms in the patient may depend on which sub-band of frequencies of the neurological signal is selected to define the electrical stimulation.

As an example of the above, patient 112 suffers from Parkinson's disease and may exhibit symptoms such as rigidity and tremor. Further, brain 120 of patient 112 exhibits two or more peak magnitudes (e.g., a multi-modal peak) of activity within a single Beta-frequency band. In this example, a first peak magnitude exists within a first sub-band of the Beta frequency band, while a second peak magnitude exists within a second sub-band of the Beta frequency band. Further, in response to electrical stimulation therapy, the first peak magnitude displays minimal suppression or reduction in magnitude, while the second peak magnitude displays a large amount of suppression or reduction in magnitude. In other words, the first peak magnitude may require electrical stimulation of a much higher magnitude to reduce the first peak magnitude to a certain amount, while the second peak magnitude may require electrical stimulation having much less magnitude to reduce the second peak magnitude to the same amount.

In this example, patient 112 receives electrical stimulation therapy to suppress rigidity and/or tremor due to Parkinson's disease. While receiving the electrical stimulation therapy, the change in severity of the patient's rigidity and tremor has been shown to correlate most to changes in the first peak magnitude within the first sub-band of the Beta frequency band, and correlate least to changes in the second peak magnitude within the second sub-band of the Beta frequency band. In other words, the change in severity of the patient's rigidity and tremor may correlate most strongly to the peak magnitude within the sub-band of the Beta frequency band that changes the least in response to electrical stimulation therapy (e.g., the peak magnitude that requires the highest level of electrical stimulation therapy to suppress), in comparison to other peak magnitudes within other sub-bands of the Beta frequency that fluctuate greatly in response to electrical stimulation.

Thus, the techniques of the disclosure describe how system 100 may select a sub-band of frequencies for use as a control signal for controlling electrical stimulation such that the electrical stimulation therapy that IMD 102 delivers correlates more accurately to the severity of the symptoms of patient 112. Furthermore, such a sub-band of frequencies may be used to accurately define the bounds of a homeostatic window as described above. For example, system 100 may select the sub-band of frequencies that demonstrates the least response to electrical stimulation, as that sub-band has been found to exhibit greater correlation to the severity of the symptoms of patient 112 than other sub-bands that exhibit greater response to electrical stimulation.

For example, as depicted in the example of FIG. 15, IMD 106 delivers, via electrodes 116, 118 disposed along leads 114, electrical stimulation at a plurality of voltage amplitudes to brain 120 of patient 112. In the example of FIG. 15, IMD 106 delivers a plurality of electrical stimulation therapies at various voltage amplitudes. Further, IMD 106 senses, via electrodes 116, 118 disposed along leads 114, a response of local field potentials of neurological signals located within a beta frequency band of about 13 Hertz to about 30 Hertz of brain 120 of patient 112.

The response of the sensed neurological signal of brain 120 of patient 112 to each electrical stimulation therapy is depicted in FIG. 15. For example, when IMD 102 delivers no electrical stimulation, the sensed neurological signal exhibits a baseline response 1501. For example, when IMD 102 delivers electrical stimulation comprising a voltage amplitude of 1 Volt, the sensed neurological signal exhibits a first response 1502. Further, when IMD 102 delivers electrical stimulation comprising a voltage amplitude of 2 Volts, the sensed neurological signal exhibits a second response 1503. When IMD 102 delivers electrical stimulation comprising a voltage amplitude of 2.5 Volts, the sensed neurological signal exhibits a third response 1504. When IMD 102 delivers electrical stimulation comprising a voltage amplitude of 3 Volts, the sensed neurological signal exhibits a fourth response 1505. When IMD 102 delivers electrical stimulation comprising a voltage amplitude of 3.5 Volts, the sensed neurological signal exhibits a fifth response 1506.

As depicted in the example of FIG. 15, the neurological signals located within the beta frequency band exhibit two peaks. A first peak lies within a first sub-band 1510 of frequencies of the beta band, at about 13 Hertz to about 22 Hertz, and centered at about 15 Hertz. A second peak lies within a second sub-band 1520 of frequencies of the beta band, at about 23 Hertz to about 28 Hertz, and centered at about 25 Hertz. As further depicted in FIG. 15, as the voltage amplitude of the electrical stimulation increases, the magnitude of the signals within first sub-band 1510 of frequencies diminish relatively slightly, while the magnitude of the signals within second sub-band 1520 of frequencies diminish relatively greatly. Thus, in accordance with the techniques of the disclosure, first sub-band 1510 may be selected as a control signal for controlling one or more parameters defining the electrical stimulation because first sub-band 1510 exhibits less responsiveness to electrical stimulation therapy then second sub-band 1520.

Similarly, first sub-band 1510 may be used to define the bounds of a homeostatic window as described above. For example, as described above, while the patient is not taking medication selected to reduce one or more symptoms, a clinician determines a minimum magnitude of one or more parameters defining the electrical stimulation therapy, such as a minimum voltage amplitude or minimum current amplitude, sufficient to reduce the one or more symptoms. The clinician defines the upper bound of the homeostatic window as a magnitude of the first sub-band 1510 of the patient at this magnitude of the electrical stimulation therapy. Further, the clinician may determine a minimum magnitude of one or more parameters defining the electrical stimulation therapy, such as a minimum voltage amplitude or minimum current amplitude, sufficient to reduce or maintain reduction of one or more symptoms when the patient is taking medication selected to reduce the symptoms. The clinician defines a lower bound of the homeostatic window as a magnitude of the first sub-band 1510 of the patient at this magnitude of stimulation.

While the example of FIG. 15 depicts only two peak magnitudes within the beta frequency band, it is recognized that other patients may have three or more peak magnitudes, and therefore three or more sub-bands of frequencies that may be selected as a control signal for controlling one or more parameters defining the electrical stimulation or to define the homeostatic window. In such an example, the sub-band of the three or more sub-bands of frequencies that exhibits the least responsiveness to electrical stimulation therapy may be selected as the control signal for controlling the electrical stimulation therapy.

Furthermore, while in the example of FIG. 15, the responsiveness of the sensed neurological signal to variations in voltage amplitude of the electrical stimulation is determined, the techniques of the disclosure recognize that other types of parameters defining the electrical stimulation may be varied to select a sub-band of frequencies. For example, a selection of one or more electrodes for delivery of the electrical stimulation, a polarity of the one or more selected electrodes, a current amplitude (for a current-controlled system), an electrical stimulation pulse width, an electrical stimulation pulse frequency, or any combination of the above may be used to select a sub-band of frequencies for use as a control signal for controlling one or more parameters defining the electrical stimulation or to define the homeostatic window.

Figure 16:
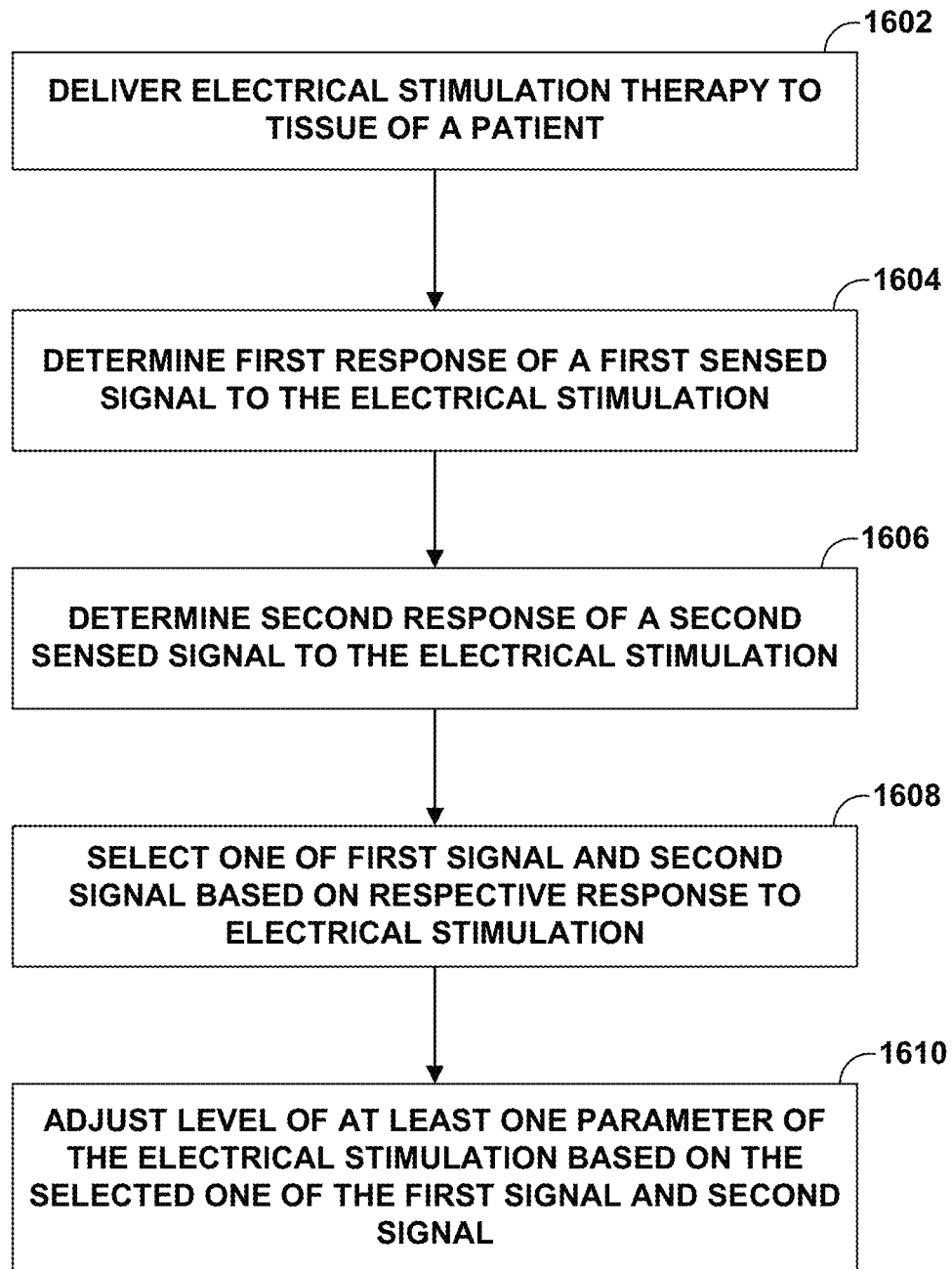
FIG. 16 is a flowchart illustrating an example operation for delivering adaptive deep brain stimulation according to an example of the techniques of the disclosure.

FIG. 16 is a flowchart illustrating an example operation for delivering adaptive deep brain stimulation according to the techniques of the disclosure. Specifically, FIG. 16 depicts an example operation for selecting a neurological signal within a sub-band of frequencies for use as a control signal for controlling electrical stimulation or to define the bounds of a homeostatic window. FIG. 16 is described with respect to FIG. 1 for convenience. As described above, in some examples, neurological signals of brain 120 of patient 112 demonstrate multiple peak magnitudes within a frequency band of sensed neurological signals. Each of these peak magnitudes may be located within a different sub-band of the frequency band, e.g., the beta band. Further, each of these sub-bands may respond differently to electrical stimulation.

IMD 106 delivers, via electrodes 116, 118 disposed along leads 114, electrical stimulation to brain 120 of patient 112 (1602). Further, IMD 106 senses, via electrodes 116, 118 disposed along leads 114, a response of neurological signals located within a frequency band of brain 120 of patient 112 e.g., in terms of a voltage amplitude of the neurological signals. In one example, the frequency band is a Beta frequency band of about 13 Hertz to about 30 Hertz.

While delivering the electrical stimulation, IMD 106 determines a first response of a first sensed neurological signal to the electrical stimulation (1604). Further, IMD 106 determines a second response of a second sensed neurological signal to the electrical stimulation (1606). In some examples, the first sensed neurological signal is within a first sub-band of frequencies of the frequency band of brain 120 of patient 112. In one example, the first sensed neurological signal is within a first sub-band of Beta-band frequencies of about 13 Hertz to about 30 Hertz, the first sub-band comprising frequencies of about 13 Hertz to about 22 Hertz. In some examples, the first sensed neurological signal comprises neurological signals at about 15 Hertz. In some examples, the second sensed neurological signal is within a second sub-band of frequencies of the frequency band of brain 120 of patient 112, and comprises frequencies that are different from the first sub-band of frequencies. In one example, the frequencies of the second sub-band are greater than the frequencies of the first sub-band. In one example, the second sensed neurological signal is within a second sub-band of Beta-band frequencies from about 13 Hertz to about 30 Hertz, the second sub-band comprising frequencies of about 23 Hertz to about 28 Hertz. In some examples, the second sensed neurological signal comprises neurological signals at about 25 Hertz.

IMD 106 selects, based on the respective response to the electrical stimulation, one of the first sensed signal and the second sensed signal for use as a control signal for controlling the electrical stimulation, or to define bounds of a homeostatic window, such as described above (1608). For example, IMD 106 determines a first magnitude of suppression of a first magnitude of the first sensed signal in response to electrical stimulation therapy. Further, IMD 106 determines a second magnitude of suppression of a second magnitude of the second sensed signal in response to electrical stimulation therapy. In this example, IMD 106 compares the first magnitude with the second magnitude to determine which, of the first sensed signal and the second sensed signal, demonstrates less response to the electrical stimulation. IMD 106 selects the one of the first sensed signal and the second sensed signal that demonstrates the least response to the electrical stimulation for use as a control signal for controlling the electrical stimulation, or to define bounds of a homeostatic window. As discussed above, the sensed signal that demonstrates the least suppression in response to electrical stimulation may more accurately indicate to the severity of symptoms of a patient than another sensed signal that demonstrates greater suppression in response to electrical stimulation.

Subsequently, IMD 106 adjusts at least one parameter of the electrical stimulation therapy based on the selected signal (e.g., the first sensed signal in the above example) (1610). For example, as magnitude of the first sensed signal increases, IMD 106 increases at least one parameter defining the electrical stimulation therapy, such as a voltage amplitude (for a voltage-controlled system) or a current amplitude (for a current-controlled system). As another example, as the magnitude of the first sensed signal decreases, IMD 106 decreases at least one parameter defining the electrical stimulation therapy. In this fashion, IMD 106 may provide adaptive DBS to patient 112 based on the first sensed signal to suppress one or more symptoms of patient 112 in proportion to the severity of the one or more systems while ensuring that the first sensed signal correlates strongly to the severity of the one or more symptoms.

Figure 17:
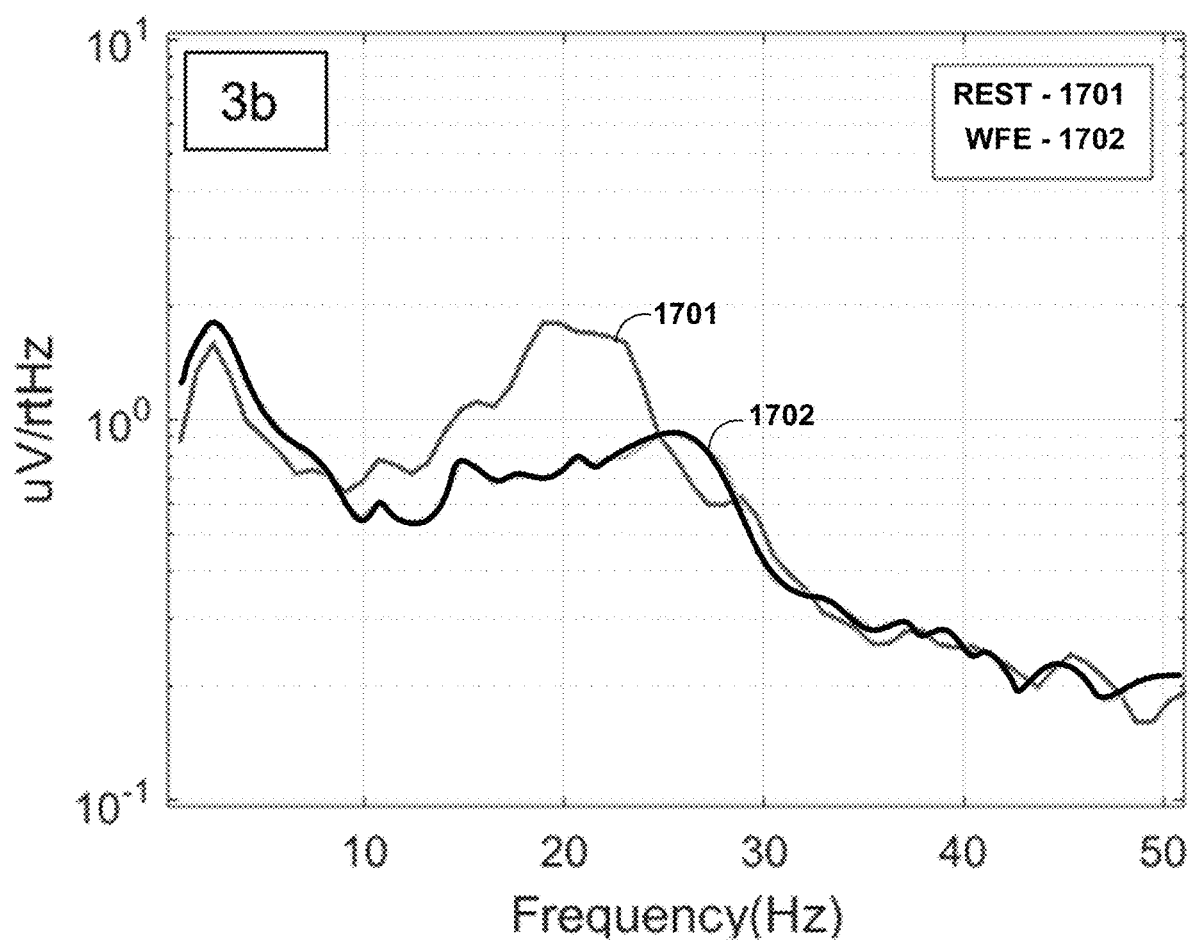
FIG. 17 is a graph illustrating measured neurological signal of a brain 120 of a patient during movement by the patient.

FIG. 17 is a graph illustrating measured neurological signal of a brain 120 of patient 112 during movement by patient 112. For convenience, FIG. 17 is described with respect to FIG. 1. The horizontal axis of FIG. 17 depicts frequency in Hertz, and the vertical axis depicts magnitude of the sensed neurological signal (e.g., a spectral power) in microvolts per root-Hertz. As described above, in some examples, neurological signals of brain 120 of patient 112 may demonstrate multiple peak magnitudes within a frequency band of sensed neurological signals. Each of these peak magnitudes may be located within a different sub-band of the frequency band. While each of these sub-bands may respond differently to the electrical stimulation, as described above, each of these sub-bands may further demonstrate different amounts of movement desynchronization during to movement by patient 112. Movement desynchronization refers to the phenomenon where neurological signals within brain 120 of patient 112 display a reduction in magnitude during movement by patient 112. Different neurological signals within the brain may exhibit different amounts of movement desynchronization. For example, movement by patient 112 may cause a first peak magnitude within a first sub-band to substantially decrease, while the same movement may cause a second peak magnitude within a second sub-band to decrease only slightly relative to the peak magnitude of the signal in the first sub-band. In other words, during a patient movement, a first peak magnitude in the first sub-band of the signal may decrease more than a second peak magnitude in a second sub-band of the signal, relative to respective peak magnitudes in the absence of patient movement. In this case, the first peak magnitude in the first sub-band exhibits a greater amount movement desynchronization than the second peak magnitude in the second sub-band, e.g., of the beta band.

In examples of system 100 where electrical stimulation is delivered based on sensing or tracking a neurological signal of brain 120 of patient 112, the correlation of the neurological signal to the severity of symptoms in patient 112, and thus the effectiveness of the electrical stimulation therapy, may depend on which sub-band of frequencies of the neurological signal is selected to define the electrical stimulation. For example, if a first sub-band is selected as a control signal for controlling electrical stimulation, and that first sub-band demonstrates a large amount of movement desynchronization, movement of patient 112 may be correlated with a suppression of signals within the first sub-band. This may cause IMD 106 to incorrectly reduce the magnitude of one or more parameters of electrical stimulation delivered to patient 112 despite the fact that patient 112 may require the higher magnitude of the one or more parameters of electrical stimulation to effectively suppress one or more symptoms of a disease of patient 112. For example, as a patient suffering from rigidity due to Parkinson's disease moves, magnitude of signals in a beta-frequency band of neurological signals may diminish, causing IMD 106 to decrease electrical stimulation, resulting in degradation in limb movement of the patient. Thus, the techniques of the disclosure describe how system 100 may select a sub-band of frequencies for use as a control signal for controlling electrical stimulation such that the electrical stimulation therapy that IMD 102 delivers correlates more accurately to the severity of the symptoms of patient 112, regardless of movement by patient 112. Furthermore, such a sub-band of frequencies may be used to accurately define the bounds of a homeostatic window as described above. For example, system 100 may select the sub-band of frequencies that demonstrates the least suppression during movement, relative to other sub-bands in a selected band (e.g., the beta band), as that sub-band has been found to exhibit greater correlation to the severity of the symptoms of patient 112 than other sub-bands that exhibit greater suppression during movement.

For example, as depicted in the example of FIG. 17, IMD 106 delivers, via electrodes 116, 118 disposed along leads 114, electrical stimulation therapy to patient 112 to suppress rigidity and tremor due to Parkinson's disease. IMD 106 senses, via electrodes 116, 118 disposed along leads 114, a magnitude of neurological signals located within a Beta frequency band of about 13 Hertz to about 30 Hertz of brain 120 of patient 112. IMD 106 records a first magnitude 1701 of neurological signals within the Beta frequency band sensed while patient 112 is at rest. Further, IMD 106 records a second magnitude 1702 of neurological signals within the Beta frequency band sensed while patient 112 is performing a walking forward exercise (WFE). As depicted in FIG. 17, upon performing the walking forward exercise, neurological signals within the Beta frequency experience movement desynchronization. This is demonstrated as a suppression of the neurological signals within the Beta frequency band, e.g., of about 13 Hertz to about 33 Hertz. Movement desynchronization may particularly be observable for frequencies in the sub-band range of about 10 Hertz to about 25 Hertz. However, the specific frequencies of such movement desynchronization may be unique for each patient and may lie anywhere within a range of about 13 Hertz to about 33 Hertz. In the example of FIG. 17, a first sub-band of frequencies centered around 25 Hertz and a second sub-band of frequencies centered around 15 Hertz may be suitable for use as control signals for controlling delivery of electrical stimulation. In the example of FIG. 17, IMD 106 may select the first sub-band of frequencies centered around 25 Hertz as the control signal for controlling the electrical stimulation or for use in defining a homeostatic window, because the first sub-band of frequencies centered around 25 Hertz depict a minimal amount of change due to movement by patient 112. In contrast, IMD 106 may not select the second sub-band of frequencies centered around 15 Hertz as a control signal for controlling electrical stimulation or for use in defining a homeostatic window, because the second sub-band of frequencies centered around 15 Hertz demonstrates a large amount of movement desynchronization.

However, the specific region of suppression due to movement desynchronization may be different from patient to patient. Thus, if a sub-band of frequencies exhibiting a large amount of movement desynchronization is used as a control signal, when patient 112 moves, the control signal reduces due to movement desynchronization, causing IMD 106 to incorrectly reduce electrical stimulation when patient 112 still requires electrical stimulation. Accordingly, by selecting a sub-band of frequencies that demonstrates minimal movement desynchronization for use as a control signal for controlling electrical stimulation or for use in defining a homeostatic window, system 100 ensures that the control signal more accurately relates to the severity of the symptoms of patient 112. Additionally, system 100 may further ensure the control signal accurately relates to the severity of the symptoms of patient 112 by selecting threshold settings for the homeostatic window, as described above, that take into account suppressed neurological signals due to movement by the patient associated with desynchronization. Furthermore, system 100 may further ensure the control signal accurately relates to the severity of the symptoms of patient 112 by selecting a ramp rate (e.g., a rate of change) of the one or more parameters of the electrical stimulation that are less susceptible to changes in the neurological signal caused by short-term movements associated with desynchronization.

While the example of FIG. 17 depicts only two peak magnitudes within the beta frequency band, it is recognized that other patients may have three or more peak magnitudes, and therefore three or more sub-bands of frequencies that may be selected as a control signal for controlling one or more parameters defining the electrical stimulation or to define the homeostatic window. In such an example, the sub-band of the three or more sub-bands of frequencies exhibits the least amount of movement desynchronization may be selected as the control signal for controlling the electrical stimulation therapy.

Alternatively, or in addition, upon determining a change in magnitude of neurological signals within a frequency band, system 100 may adjust the ramp time (e.g., the rate of change) of one or more parameters of the electrical stimulation therapy. For example, in a fast-ramping system (e.g., a system where one or more parameters of the electrical stimulation are adjusted at time steps less than one second), upon determining that a Beta frequency band of patient 112 is susceptible to movement desynchronization, IMD 106 may decrease a rate of change of the one or more parameters of the electrical stimulation therapy. In alternate examples, upon detecting a movement of patient 112 related to a Beta frequency band desynchronization, such as walking, IMD 106 may decrease the rate of change of the one or more parameters of the electrical stimulation therapy while the movement is detected. In further examples, a rate of change of the one or more parameters of the electrical stimulation therapy is selected such that the one or more parameters of the electrical stimulation remains constant for a duration of the movement of patient 112. Further, when defining the bounds of a homeostatic window as described above, the lower limit of the at least one parameter is defined such that IMD 106 ramps up the one or more parameters of the electrical stimulation, even when a movement of patient 112 causes Beta frequency band desynchronization. As one example, in a current-controlled system, a current amplitude is increased from zero to a maximum current selected from a range of about 1.3 milliamps to about 2.0 milliamps over a time period selected from about 250 milliseconds to about 1 second. As another example, in a voltage-controlled system, a voltage amplitude is increased from zero to a maximum voltage selected from a range of about 2 volts to about 3 volts over a time period selected from about 250 milliseconds to about 1 second.

In further examples, upon detecting movement associated with desynchronization, IMD 106 may switch from a fast-ramping system to a slow-ramping system (e.g., a system where one or more parameters of the electrical stimulation are adjusted at time steps greater than one second). In other words, during normal operation, IMD 106 may adjust the one or more parameters of the electrical stimulation at a rate greater than once per second. Upon detecting movement associated with desynchronization, IMD 106 decreases the ramp rate such that IMD 106 adjusts the one or more parameters of the electrical stimulation at a rate less than once per second.

As a further example, in a slow-ramping system, IMD 106 may deliver adaptive electrical stimulation therapy that tracks on- and off-phases of medication administered to patient 112 to reduce one or more symptoms of patient 112. For example, patient 112 may suffer from Parkinson's disease and take medication administered to suppress dyskinesia and improve longevity. Such medication may both suppress the symptoms of dyskinesia in patient 112, and also suppress neurological signals within a Beta frequency band of brain 120 of patient 112. The effects of such medication on patient 1112 may not show effects for about 30 minutes after dosage, and the medication may gradually reach its full strength over a wash-in period of about 10 minutes. Similarly, as the medication wears off, the effects of the medication in suppressing dyskinesia may also gradually diminish.

Accordingly, system 100 may adjust the rate of change of the one or more parameters of the electrical stimulation therapy more slowly such that the one or more parameters of the electrical stimulation is increased at approximately the same rate as the medication wash-in period (e.g., the period of time between when the patient takes the medication and the medication reaches full strength). As one example, in a current-controlled system, a current amplitude is increased from zero to a maximum current selected from a range of about 1.3 milliamps to about 2.0 milliamps over a time period selected from about 10 minutes to about 30 minutes. Such a time period may be set by the clinician and based on the wash-in period of a specific medication taken by the patient. As another example, in a voltage-controlled system, a voltage amplitude is increased from zero to a maximum voltage selected from a range of about 2 volts to about 3 volts over a time period selected from about 10 minutes to about 30 minutes. Such a time period may also be set by the clinician and based on the wash-in period of a specific medication taken by the patient. Such a ramp rate may allow IMD 106 to track changes in a beta frequency band of patient 112 due to medication. Further, such a ramp rate may allow IMD 106 to avoid periods of desynchronization in the Beta frequency band due to movements of patient 112 that are expected to be less than 10 minutes in duration.

Furthermore, while in the example of FIG. 17, examples are provided wherein a ramp rate of one of current amplitude or voltage amplitude is adjusted, the techniques of the disclosure recognize that other types of parameters defining the electrical stimulation may be adjusted as a function of the amount of movement desynchronization displayed by the sensed neurological signal. For example, a ramp rate of one or more of: a selection of one or more electrodes for delivery of the electrical stimulation, a polarity of the one or more selected electrodes, a current amplitude (for a current-controlled system), an electrical stimulation pulse width, an electrical stimulation pulse frequency, or any combination of the above may be adjusted.

Figure 18:
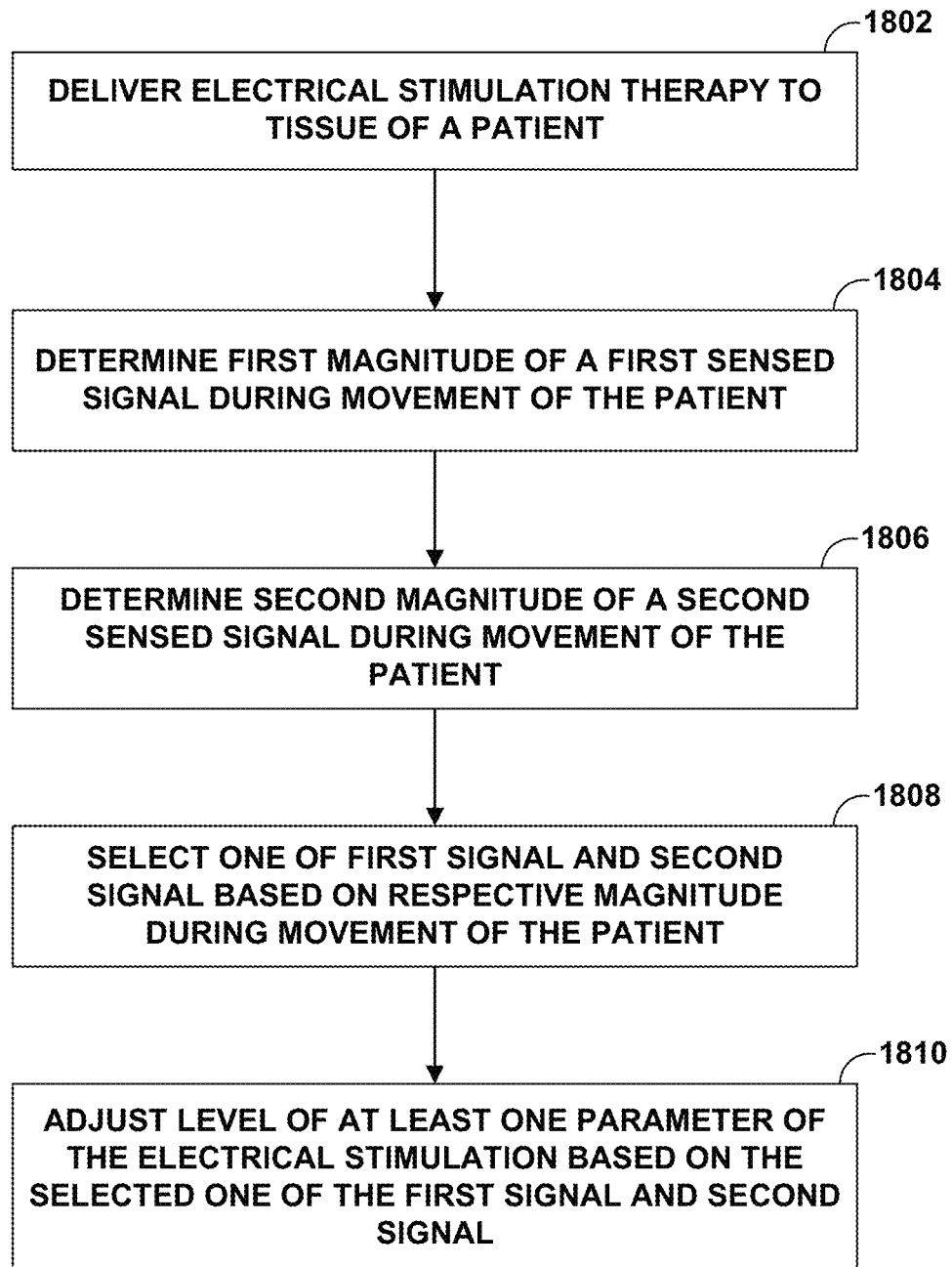
FIG. 18 is a flowchart illustrating an example operation for delivering adaptive deep brain stimulation according to an example of the techniques of the disclosure.

FIG. 18 is a flowchart illustrating an example operation for delivering adaptive deep brain stimulation according to the techniques of the disclosure. Specifically, FIG. 18 depicts an example operation for selecting a neurological signal within a sub-band of frequencies for use as a control signal for controlling electrical stimulation or to define the bounds of a homeostatic window. FIG. 18 is described with respect to FIG. 1 for convenience. As described above, in some examples, neurological signals of brain 120 of patient 112 demonstrate multiple peak magnitudes within a frequency band of sensed neurological signals. Each of these peak magnitudes may be located within a different sub-band of the frequency band. Further, each of these sub-bands may express differing amounts of desynchronization during movement of patient 112.

IMD 106 delivers, via electrodes 116, 118 disposed along leads 114, electrical stimulation to brain 120 of patient 112 (1802). Further, IMD 106 senses, via electrodes 116, 118 disposed along leads 114, a magnitude of neurological signals located within a frequency band of brain 120 of patient 112. In one example, the frequency band is a Beta frequency band of about 13 Hertz to about 30 Hertz.

While delivering the electrical stimulation, IMD 106 determines a first magnitude of a first sensed neurological signal during movement by the patient (1804). Further, IMD 106 senses a second magnitude of a second sensed neurological signal during the movement by the patient (1806). In some examples, the first sensed neurological signal is within a first sub-band of frequencies of the frequency band of brain 120 of patient 112. In one example, the first sensed neurological signal is within a first sub-band of Beta-band frequencies of about 13 Hertz to about 30 Hertz, the first sub-band comprising frequencies of about 13 Hertz to about 22 Hertz. In some examples, the first sensed neurological signal comprises neurological signals within the first sub-band at about 15 Hertz. In some examples, the second sensed neurological signal is within a second sub-band of frequencies of the frequency band of brain 120 of patient 112, and comprises frequencies that are different from the first sub-band of frequencies. In one example, the second sensed neurological signal is within a second sub-band of Beta-band frequencies, the second sub-band comprising frequencies of about 23 Hertz to about 28 Hertz. In some examples, the second sensed neurological signal comprises neurological signals is in the second sub-band at about 25 Hertz.

IMD 106 selects, based on the respective magnitude during the movement of the patient, the one of the first sensed signal and the second sensed signal for use as a control signal for controlling the electrical stimulation, or to define bounds of a homeostatic window, such as described above (1808). For example, IMD 106 determines a first magnitude of suppression of a first magnitude of the first sensed signal during the movement of the patient. Further, IMD 106 determines a second magnitude of suppression of a second magnitude of the second sensed signal during the movement of the patient. In this example, IMD 106 compares the first magnitude with the second magnitude to determine which, of the first sensed signal and the second sensed signal, demonstrates a lesser change, e.g., lesser change in magnitude during the movement of the patient. IMD 106 selects the one of the first sensed signal and the second sensed signal that demonstrates the least change during the movement of the patient for use as a control signal for controlling the electrical stimulation, or to define bounds of a homeostatic window. As discussed above, by using the sensed signal that demonstrates the least suppression during movement of the patient, system 100 may mitigate circumstances where system 100 detects a suppression of the neurological signal caused by movement, incorrectly interpreting the suppression as a reduced need by patient 112 for the electrical stimulation therapy, and responding by reducing the one or more parameters of the electrical stimulation.

Subsequently, IMD 106 adjusts at least one parameter of the electrical stimulation therapy based on the selected signal (e.g., the first sensed signal in the above example) (1810). For example, as magnitude of the first sensed signal increases, IMD 106 increases at least one parameter defining the electrical stimulation therapy, such as a voltage amplitude (for a voltage-controlled system) or a current amplitude (for a current-controlled system). As another example, as magnitude of the first sensed signal decreases, IMD 106 decreases at least one parameter defining the electrical stimulation therapy. Alternatively, IMD 106 may adjust a rate of change of the at least one parameter defining the electrical stimulation therapy, as described above. In this fashion, IMD 106 may provide adaptive DBS to patient 112 based on the first sensed signal to suppress one or more symptoms of patient 112 in proportion to the severity of the one or more systems while ensuring that a neurological signal selected as a control signal for the electrical stimulation is selected such that the control signal is robust to movement desynchronization.

As an example, IMD 106 may use the first sensed signal to define the bounds of a homeostatic window as described above. For example, as described above, while the patient is not taking medication selected to reduce one or more symptoms, a clinician determines a minimum magnitude of one or more parameters defining the electrical stimulation therapy, such as a minimum voltage amplitude or minimum current amplitude, sufficient to reduce the one or more symptoms. The clinician defines the upper bound of the homeostatic window as a magnitude of the first sensed signal of the patient at this magnitude of the electrical stimulation therapy. Further, the clinician may determine a minimum magnitude of one or more parameters defining the electrical stimulation therapy, such as a minimum voltage amplitude or minimum current amplitude, sufficient to reduce or maintain reduction of one or more symptoms when the patient is taking medication selected to reduce the symptoms. The clinician defines a lower bound of the homeostatic window as a magnitude of the first sensed signal of the patient at this magnitude of stimulation. Subsequently, IMD 106 delivers electrical stimulation to the patient, and may adjust one or more parameters defining the electrical stimulation within a parameter range defined by the lower and upper bounds of the therapeutic window based on the activity of the first sensed signal within the homeostatic window.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method for delivering electrical stimulation therapy to a patient, the method comprising:
   delivering the electrical stimulation therapy to a tissue of a patient via electrodes;
   selecting between a first sensed signal or a second sensed signal based upon a comparison of changes in each of the first sensed signal and the second sensed signal, the changes in each of the first sensed signal and the second sensed signal being indicative of movement desynchronization in each of the first sensed signal and the second sensed signal resulting from a movement by the patient; and
   adjusting, based on the selected one of the first sensed signal or the second sensed signal, a level of at least one parameter of the electrical stimulation therapy.

2. The method of claim 1, wherein the method further comprises comparing a magnitude of a first change of the first sensed signal to a magnitude of a second change of the second sensed signal, wherein the first change is indicative of first movement desynchronization in the first sensed signal and the second change is indicative of second movement desynchronization in the second sensed signal.

3. The method of claim 1, further comprising correlating the movement by the patient to the changes in each of the first sensed signal and the second sensed signal.

4. The method of claim 1,
wherein the first sensed signal is a first signal of a brain of a patient having a first frequency within a frequency band, and
wherein the second sensed signal is a second signal of a brain of a patient having a second frequency within the frequency band and different from the first frequency.

5. The method of claim 4, wherein the frequency band is a Beta band of frequencies from about 13 Hertz to about 30 Hertz, the first frequency is in a first sub-band of the Beta band including a frequency of about 15 Hertz, and the second frequency is in a second sub-band of the Beta band different than the first sub-band and including a frequency of about 25 Hertz.

6. The method of claim 1, wherein adjusting the level of the at least one parameter of the electrical stimulation therapy comprises adjusting a rate of change of the at least one parameter of the electrical stimulation therapy.

7. The method of claim 6, wherein adjusting the rate of change of the at least one parameter of the electrical stimulation therapy comprises:
switching, from adjusting, in less than approximately 1 second, the at least one parameter of the electrical stimulation therapy from a first value to a second value, to adjusting, in greater than approximately 1 second, the at least one parameter of the electrical stimulation therapy from the first value to the second value.

8. The method of claim 1, wherein adjusting the level of the at least one parameter of the electrical stimulation therapy comprises increasing a length of a delay prior to adjusting the level of the at least one parameter of the electrical stimulation therapy, wherein the length of the delay is based on the selected one of the first sensed signal or the second sensed signal.

9. The method of claim 1, wherein the method further comprises:
determining the changes in each of the first sensed signal and the second sensed signal; and
comparing the changes in each of the first sensed signal and the second sensed signal.

10. The method of claim 1, wherein delivering the electrical stimulation therapy to the tissue of the patient via electrodes comprises selecting one or more parameters defining the electrical stimulation therapy to suppress a symptom of Parkinson's disease.

11. The method of claim 1, further comprising adjusting the level of the at least one parameter of the electrical stimulation therapy such that the selected one of the first sensed signal of the patient or the second sensed signal is not less than a lower bound and not greater than an upper bound of a range.

12. A medical device system comprising:
a medical device comprising:
stimulation generation circuitry configured to deliver electrical stimulation therapy to tissue of a patient via electrodes; and
processing circuitry configured to:
select between a first sensed signal or a second sensed signal based upon a comparison of changes in each of the first sensed signal and the second sensed signal, the changes in each of the first sensed signal and the second sensed signal being indicative of movement desynchronization in each of the first sensed signal and the second sensed signal resulting from a movement by the patient; and
adjust, based on the selected one of the first sensed signal or the second sensed signal, a level of at least one parameter of the electrical stimulation therapy.

13. The medical device system of claim 12,
wherein the first sensed signal is a first signal of a brain of a patient having a first frequency within a frequency band, and
wherein the second sensed signal is a second signal of a brain of a patient having a second frequency within the frequency band and different from the first frequency.

14. The medical device system of claim 13, wherein the frequency band is a Beta band of frequencies from about 13 Hertz to about 30 Hertz, the first frequency is in a first sub-band of the Beta band including 15 Hertz, and the second frequency is in a second sub-band of the Beta band different from the first sub-band and including 25 Hertz.

15. The medical device system of claim 12, wherein, to adjust the level of the at least one parameter of the electrical stimulation therapy, the processing circuitry is further configured to adjust a rate of change of the at least one parameter of the electrical stimulation therapy.

16. The medical device system of claim 12, wherein, to adjust the level of the at least one parameter of the electrical stimulation therapy, the processing circuitry is configured to switch, from adjusting, in less than approximately 1 second, the at least one parameter of the electrical stimulation therapy from a first value to a second value, to adjusting, in greater than approximately 1 second, the at least one parameter of the electrical stimulation therapy from the first value to the second value.

17. The medical device system of claim 12, wherein, to adjust the level of the at least one parameter of the electrical stimulation therapy, the processing circuitry is further configured to increase a length of a delay prior to adjusting the level of the at least one parameter of the electrical stimulation therapy, wherein the length of the delay is based on the selected one of the first sensed signal or the second sensed signal.

18. The medical device system of claim 12, wherein the processing circuitry is further configured to:
determine the changes in each of the first sensed signal and the second sensed signal; and
compare the changes in each of the first sensed signal and the second sensed signal.

19. The medical device system of claim 12, further comprising an external programmer is configured to:
determine the changes in each of the first sensed signal and the second sensed signal; and
compare the changes in each of the first sensed signal and the second sensed signal.

20. The medical device system of claim 12, wherein, to deliver the electrical stimulation therapy to the tissue of the patient via electrodes, the processing circuitry is configured to select one or more parameters defining the electrical stimulation therapy to suppress a symptom of Parkinson's disease.

21. A medical device system comprising:
means for delivering the electrical stimulation therapy to a tissue of a patient via electrodes;
means for selecting between a first sensed signal or a second sensed signal based upon a comparison of changes in each of the first sensed signal and the second sensed signal, the changes in each of the first sensed signal and the second sensed signal being indicative of movement desynchronization in each of the first sensed signal and the second sensed signal resulting from a movement by the patient; and
means for adjusting, based on the selected one of the first sensed signal or the second sensed signal, a level of at least one parameter of the electrical stimulation therapy.

* * * * *